US010870807B2

United States Patent
Al-Ghamdi et al.

(10) Patent No.: US 10,870,807 B2
(45) Date of Patent: Dec. 22, 2020

(54) PROCESS AND SYSTEM FOR CONVERSION OF CRUDE OIL TO PETROCHEMICALS AND FUEL PRODUCTS INTEGRATING STEAM CRACKING, FLUID CATALYTIC CRACKING, AND CONVERSION OF NAPHTHA INTO CHEMICAL RICH REFORMATE

(71) Applicant: Saudi Arabian Oil Company, Dhahran (SA)

(72) Inventors: Mohammed Saeed Al-Ghamdi, Dammam (SA); Bader BaHammam, Dammam (SA); Naif Al Osaimi, Dammam (SA); Sami Barnawi, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 142 days.

(21) Appl. No.: 15/817,148

(22) Filed: Nov. 17, 2017

(65) Prior Publication Data
US 2018/0155642 A1    Jun. 7, 2018

Related U.S. Application Data

(63) Continuation-in-part of application No. 15/710,799, filed on Sep. 20, 2017, now abandoned.
(Continued)

(51) Int. Cl.
*C10G 69/08* (2006.01)
*C10G 11/02* (2006.01)
(Continued)

(52) U.S. Cl.
CPC .............. *C10G 69/08* (2013.01); *C07C 29/04* (2013.01); *C07C 31/12* (2013.01); *C10G 11/02* (2013.01);
(Continued)

(58) Field of Classification Search
CPC ........ C10G 65/18; C10G 47/02; C10G 47/24; C10G 7/06; C10G 2400/08;
(Continued)

(56) References Cited

U.S. PATENT DOCUMENTS 3,472,909 A    10/1969  Raymond et al.
3,702,292 A    11/1972  Burich
(Continued)

FOREIGN PATENT DOCUMENTS

CA    2674212 C    4/2015
CN    103374395 B    7/2015
(Continued)

OTHER PUBLICATIONS

PCT/US2017/062614, International Search Report and Written Opinion dated Apr. 4, 2018, 12 pages.

*Primary Examiner* — Randy Boyer
*Assistant Examiner* — Juan C Valencia
(74) *Attorney, Agent, or Firm* — Abelman, Frayne and Schwab

(57) ABSTRACT

Process scheme configurations are disclosed that enable conversion of crude oil feeds with several processing units in an integrated manner into petrochemicals. The designs utilize minimum capital expenditures to prepare suitable feedstocks for the steam cracker complex. The integrated process for converting crude oil to petrochemical products including olefins and aromatics, and fuel products, includes mixed feed steam cracking, fluid catalytic cracking and conversion of naphtha to chemical rich reformate. Feeds to the mixed feed steam cracker include light products from hydroprocessing zones within the battery limits, recycle streams from the C3 and C4 olefins recovery steps, and raffinate from a pyrolysis gasoline and FCC naphtha aromatics extraction zone within the battery limits. Chemical (Continued)

reformate from straight run naphtha streams is used as an additional feed to the aromatics extraction zone and or the mixed feed steam cracker.

32 Claims, 22 Drawing Sheets

Related U.S. Application Data

(60) Provisional application No. 62/424,883, filed on Nov. 21, 2016, provisional application No. 62/450,018, filed on Jan. 24, 2017, provisional application No. 62/450,060, filed on Jan. 24, 2017, provisional application No. 62/450,058, filed on Jan. 24, 2017.

(51) Int. Cl.
| | |
|---|---|
| *C07C 29/04* | (2006.01) |
| *C07C 31/12* | (2006.01) |
| *C10G 7/06* | (2006.01) |
| *B01D 3/14* | (2006.01) |

(52) U.S. Cl.
CPC .......... *B01D 3/143* (2013.01); *C10G 7/06* (2013.01); *C10G 2300/107* (2013.01); *C10G 2300/1048* (2013.01); *C10G 2300/1077* (2013.01); *C10G 2400/02* (2013.01); *C10G 2400/30* (2013.01)

(58) Field of Classification Search
CPC ........ C10G 2300/1048; C10G 2400/28; C10G 2400/20; C10G 2400/16; C10G 2400/04; C10G 2300/1074; B01D 3/143; B01D 3/10; B01D 3/009; B01D 3/007
See application file for complete search history.

(56) References Cited

U.S. PATENT DOCUMENTS

| | | | |
|---|---|---|---|
| 3,842,138 | A | 10/1974 | Chahvekilian et al. |
| 3,855,113 | A | 12/1974 | Gould |
| 3,898,299 | A | 8/1975 | Jones |
| 4,065,379 | A | 12/1977 | Soonawala et al. |
| 4,115,467 | A | 9/1978 | Fowler |
| 4,180,453 | A | 12/1979 | Franck et al. |
| 5,906,728 | A | 5/1999 | Iaccino et al. |
| 5,980,732 | A | 11/1999 | Gillis |
| 5,981,818 | A | 11/1999 | Purvis et al. |
| 6,106,697 | A | 8/2000 | Swan et al. |
| 6,166,279 | A | 12/2000 | Schwab et al. |
| 6,210,561 | B1 | 4/2001 | Bradow et al. |
| 6,538,168 | B1 | 3/2003 | Schwab et al. |
| 7,550,642 | B2 | 6/2009 | Powers |
| 7,938,952 | B2 | 5/2011 | Coylar et al. |
| 8,394,900 | B2 | 3/2013 | Abhari |
| 8,529,753 | B2 | 9/2013 | Niu et al. |
| 8,540,870 | B2 | 9/2013 | McGehee et al. |
| 8,722,950 | B2 | 5/2014 | Hal et al. |
| 8,754,277 | B2 | 6/2014 | Vijayakumari et al. |
| 8,936,716 | B2 | 1/2015 | Hoehn et al. |
| 8,940,950 | B2 | 1/2015 | Ellrich et al. |
| 9,273,256 | B2 | 3/2016 | Gillis et al. |
| 9,452,955 | B2 | 9/2016 | Sieli et al. |
| 9,464,240 | B2 | 10/2016 | Bridges et al. |
| 9,550,707 | B2 | 1/2017 | Schrod et al. |
| 9,650,580 | B2 | 5/2017 | Merdrignac et al. |
| 9,856,425 | B2 | 1/2018 | Ward et al. |
| 9,862,898 | B2 | 1/2018 | Ward et al. |
| 9,920,263 | B2 | 3/2018 | Klein et al. |
| 2004/0054247 | A1 | 3/2004 | Powers |
| 2007/0090018 | A1 | 4/2007 | Keusenkothen et al. |
| 2007/0232846 | A1 | 10/2007 | Baumgartner et al. |
| 2008/0194900 | A1 | 8/2008 | Bhirud |
| 2010/0056839 | A1 | 3/2010 | Ramachandran et al. |
| 2010/0087692 | A1 | 4/2010 | Yoshimura et al. |
| 2010/0168487 | A1 | 7/2010 | Sawyer et al. |
| 2010/0285950 | A1 | 11/2010 | Mao |
| 2011/0042269 | A1 | 2/2011 | Keuchler et al. |
| 2011/0119994 | A1 | 5/2011 | Hogendoorn et al. |
| 2011/0174682 | A1 | 7/2011 | Iaccino |
| 2012/0261308 | A1* | 10/2012 | Klein ................ C10G 7/12 208/92 |
| 2013/0237714 | A1 | 9/2013 | Vijayakumari et al. |
| 2013/0245295 | A1 | 9/2013 | Westrenen |
| 2013/0248419 | A1 | 9/2013 | Abba et al. |
| 2014/0081061 | A1 | 3/2014 | Stanley et al. |
| 2016/0115400 | A1 | 4/2016 | Sun et al. |
| 2016/0137933 | A1 | 5/2016 | Ward et al. |
| 2016/0368838 | A1 | 12/2016 | Ward et al. |
| 2016/0369180 | A1 | 12/2016 | Ward et al. |
| 2016/0369188 | A1 | 12/2016 | Housmans et al. |
| 2017/0009155 | A1 | 1/2017 | Oprins |

FOREIGN PATENT DOCUMENTS

| | | |
|---|---|---|
| FR | 3014894 A1 | 6/2015 |
| GB | 1301019 A | 12/1972 |
| WO | 2014177424 A2 | 11/2014 |
| WO | 2016071776 A2 | 5/2016 |
| WO | 2017014976 A1 | 1/2017 |

\* cited by examiner

PROCESS AND SYSTEM FOR CONVERSION OF CRUDE OIL TO PETROCHEMICALS AND FUEL PRODUCTS INTEGRATING STEAM CRACKING, FLUID CATALYTIC CRACKING, AND CONVERSION OF NAPHTHA INTO CHEMICAL RICH REFORMATE

RELATED APPLICATIONS

This application claims priority to U.S. Provisional Patent Application No. 62/450,060 filed Jan. 24, 2017, and is a Continuation-In-Part of U.S. patent application Ser. No. 15/710,799 filed Sep. 20, 2017, which claims priority to U.S. Provisional Patent Application No. 62/424,883 filed Nov. 21, 2016, U.S. Provisional Patent Application No. 62/450,018 filed Jan. 24, 2017, and U.S. Provisional Patent Application No. 62/450,058 filed Jan. 24, 2017, the contents of which are all incorporated herein by reference in their entireties.

BACKGROUND OF THE INVENTION

Field of the Invention

The inventions disclosed herein relate to an integrated process and system for converting crude oil to petrochemicals and fuel products.

Description of Related Art

The lower olefins (i.e., ethylene, propylene, butylene and butadiene) and aromatics (i.e., benzene, toluene and xylene) are basic intermediates which are widely used in the petrochemical and chemical industries. Thermal cracking, or steam pyrolysis, is a major type of process for forming these materials, typically in the presence of steam, and in the absence of oxygen. Typical feedstocks for steam pyrolysis can include petroleum gases, such as ethane, and distillates such as naphtha, kerosene and gas oil. The availability of these feedstocks is usually limited and requires costly and energy-intensive process steps in a crude oil refinery.

A very significant portion of ethylene production relies on naphtha as the feedstock. However, heavy naphtha has a lower paraffin and higher aromatics content than light naphtha, making it less suitable as feedstock in the production of ethylene without upgrading. Heavy naphtha can vary in the amount of total paraffins and aromatics based on its source. Paraffins content can range between about 27-70%, naphthenes content can range between about 15-60%, and the aromatics content can range between about 10-36% (volume basis).

Many chemicals producers are limited by the supply and quality of feed from nearby refiners due to reliance on oil refinery by-products as feed. Chemicals producers are also limited by the high cost of oil refining and its associated fuels markets, which may negatively influence the economic value of refinery sourced feeds. Higher global fuel efficiency standards for automobiles and trucks will reduce fuels demand and narrow refinery margins, and may complicate the economics of fuels and chemicals supply and/or markets.

A need remains in the art for improved processes for converting crude oil to basic chemical intermediates such as lower olefins and aromatics. In addition, a need remains in the art for new approaches that offer higher value chemical production opportunities with greater leverage on economies of scale.

SUMMARY

In accordance with one or more embodiments, the invention relates to an integrated process for producing petrochemicals and fuel product from a crude oil feed. The integrated process includes an initial separation step to separate from a crude oil feed in an atmospheric distillation zone at least a fraction comprising straight run naphtha and lighter components, one or more middle distillate fractions, fractions, and an atmospheric residue fraction. A vacuum gas oil fraction is separated from the atmospheric residue fraction in a vacuum distillation zone. In a distillate hydroprocessing ("DHP") zone, such as a diesel hydrotreater, at least a portion of the middle distillates are processed to produce at least a naphtha fraction and a diesel fuel fraction. The vacuum gas oil fraction is processed in a fluid catalytic cracking zone to produce at least a light olefins FCC fraction that is recovered as petrochemicals, an FCC naphtha fraction and a cycle oil fraction.

The light components such as LPG from the atmospheric distillation zone, and an aromatics extraction zone raffinate, are processed in a mixed feed steam cracking zone. All or a portion of the straight run naphtha is passed to a catalytic reforming zone to produce chemical rich reformate as additional feed to the aromatics extraction zone. The products from the mixed feed steam cracking zone include a mixed product stream comprising $H_2$, methane, ethane, ethylene, mixed C3s and mixed C4s; a pyrolysis gasoline stream; and a pyrolysis oil stream.

From the mixed product stream C3s and the mixed C4s, petrochemicals ethylene, propylene and butylenes are recovered. Ethane and non-olefinic C3s are recycled to the mixed feed steam cracking zone, and non-olefinic C4s are recycled to the mixed feed steam cracking zone or to a separate processing zone for production of additional petrochemicals. Pyrolysis gasoline is treated in a py-gas hydroprocessing zone to produce hydrotreated pyrolysis gasoline. The hydrotreated pyrolysis gasoline is routed to the aromatics extraction zone to recover aromatic products and the aromatics extraction zone raffinate that is recycled to the mixed feed steam cracking zone.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF THE DRAWINGS

The invention will be described in further detail below and with reference to the attached drawings in which the same or similar elements are referred to by the same number, and where.

DESCRIPTION

Figure 1:
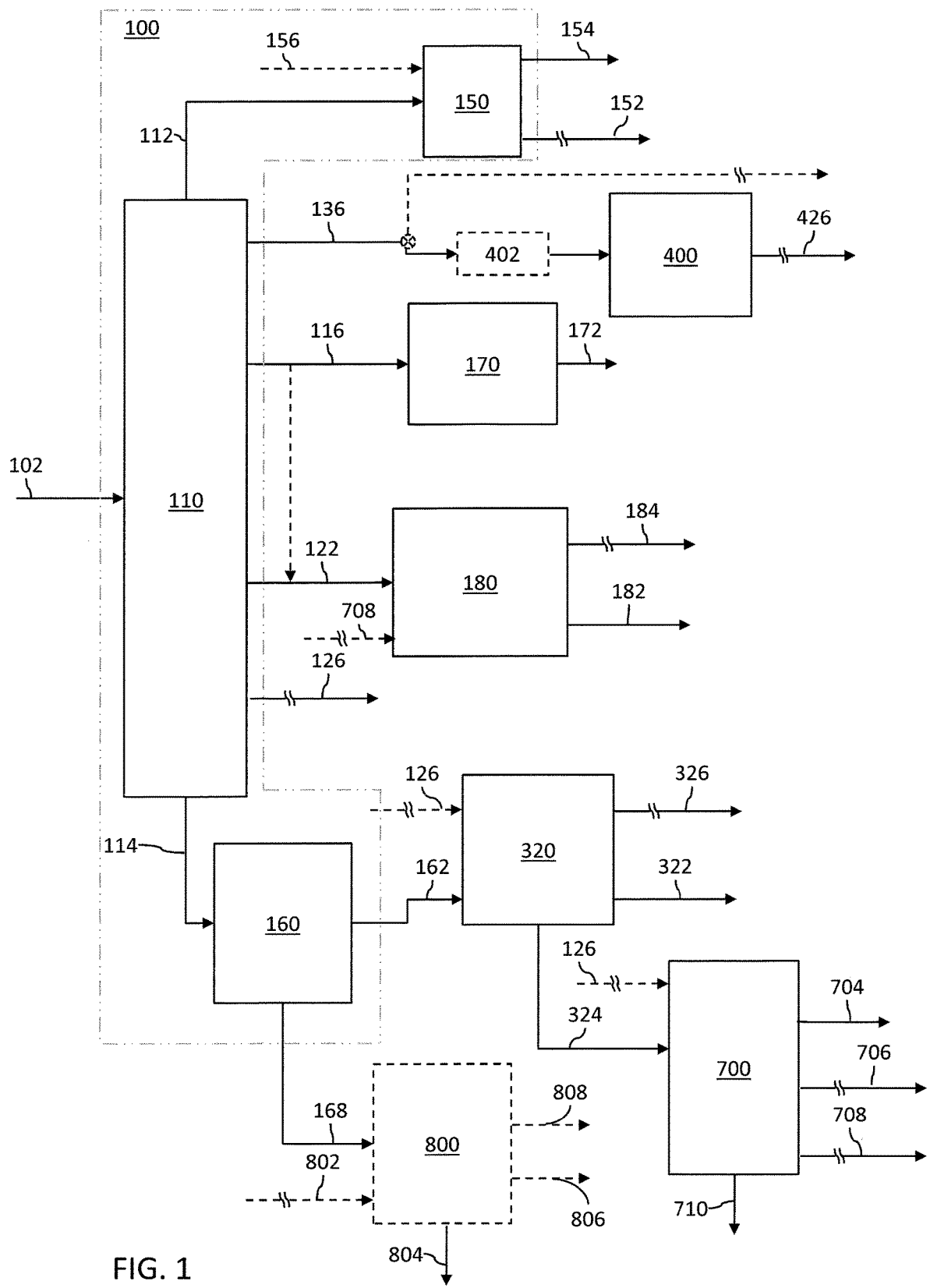
FIG. 1 schematically depicts operations upstream of a steam cracker complex in embodiments of processes for producing petrochemicals and fuel products integrating fluid catalytic cracking and steam cracking.

Process scheme configurations are disclosed that enable conversion of crude oil feeds with several processing units in an integrated manner into petrochemicals. The designs utilize minimum capital expenditures to prepare suitable feedstocks for the steam cracker complex. The integrated process for converting crude oil to petrochemical products including olefins and aromatics, and fuel products, includes mixed feed steam cracking, fluid catalytic cracking and conversion of naphtha to chemical rich reformate. Feeds to the mixed feed steam cracker include light products from hydroprocessing zones within the battery limits, recycle streams from the C3 and C4 olefins recovery steps, and raffinate from a pyrolysis gasoline and FCC naphtha aromatics extraction zone within the battery limits. Chemical reformate from straight run naphtha streams is used as an additional feed to the aromatics extraction zone and or the mixed feed steam cracker.

The phrase "a major portion" with respect to a particular stream or plural streams means at least about 50 wt % and up to 100 wt %, or the same values of another specified unit.

The phrase "a significant portion" with respect to a particular stream or plural streams means at least about 75 wt % and up to 100 wt %, or the same values of another specified unit.

The phrase "a substantial portion" with respect to a particular stream or plural streams means at least about 90, 95, 98 or 99 wt % and up to 100 wt %, or the same values of another specified unit.

The phrase "a minor portion" with respect to a particular stream or plural streams means from about 1, 2, 4 or 10 wt %, up to about 20, 30, 40 or 50 wt %, or the same values of another specified unit.

The term "crude oil" as used herein refers to petroleum extracted from geologic formations in its unrefined form. Crude oil suitable as the source material for the processes herein include Arabian Heavy, Arabian Light, Arabian Extra Light, other Gulf crudes, Brent, North Sea crudes, North and West African crudes, Indonesian, Chinese crudes, or mixtures thereof. The crude petroleum mixtures can be whole range crude oil or topped crude oil. As used herein, "crude oil" also refers to such mixtures that have undergone some pre-treatment such as water-oil separation; and/or gas-oil separation; and/or desalting; and/or stabilization. In certain embodiments, crude oil refers to any of such mixtures having an API gravity (ASTM D287 standard), of greater than or equal to about 20°, 30°, 32°, 34°, 36°, 38°, 40°, 42° or 44°.

The acronym "AXL" as used herein refers to Arab Extra Light crude oil, characterized by an API gravity of greater than or equal to about 38°, 40°, 42° or 44°, and in certain embodiments in the range of about 38°-46°, 38°-44°, 38°-42°, 38°-40.5°, 39°-46°, 39°-44°, 39°-42° or 39°-40.5°.

The acronym "AL" as used herein refers to Arab Light crude oil, characterized by an API gravity of greater than or equal to about 30°, 32°, 34°, 36° or 38°, and in certain embodiments in the range of about 30°-38°, 30°-36°, 30°-35°, 32°-38°, 32°-36°, 32°-35°, 33°-38°, 33°-36° or 33°-35°.

The acronym "LPG" as used herein refers to the well-known acronym for the term "liquefied petroleum gas," and generally is a mixture of C3-C4 hydrocarbons. In certain embodiments, these are also referred to as "light ends."

The term "naphtha" as used herein refers to hydrocarbons boiling in the range of about 20-205, 20-193, 20-190, 20-180, 20-170, 32-205, 32-193, 32-190, 32-180, 32-170, 36-205, 36-193, 36-190, 36-180 or 36-170° C.

The term "light naphtha" as used herein refers to hydrocarbons boiling in the range of about 20-110, 20-100, 20-90, 20-88, 32-110, 32-100, 32-90, 32-88, 36-110, 36-100, 36-90 or 36-88° C.

The term "heavy naphtha" as used herein refers to hydrocarbons boiling in the range of about 90-205, 90-193, 90-190, 90-180, 90-170, 93-205, 93-193, 93-190, 93-180, 93-170, 100-205, 100-193, 100-190, 100-180, 100-170, 110-205, 110-193, 110-190, 110-180 or 110-170° C.

In certain embodiments naphtha, light naphtha and/or heavy naphtha refer to such petroleum fractions obtained by crude oil distillation, or distillation of intermediate refinery processes as described herein.

The modifying term "straight run" is used herein having its well-known meaning, that is, describing fractions derived directly from the atmospheric distillation unit, optionally subjected to steam stripping, without other refinery treatment such as hydroprocessing, fluid catalytic cracking or steam cracking. An example of this is "straight run naphtha" and its acronym "SRN" which accordingly refers to "naphtha" defined above that is derived directly from the atmospheric distillation unit, optionally subjected to steam stripping, as is well known.

The term "kerosene" as used herein refers to hydrocarbons boiling in the range of about 170-280, 170-270, 170-260, 180-280, 180-270, 180-260, 190-280, 190-270, 190-260, 193-280, 193-270 or 193-260° C.

The term "light kerosene" as used herein refers to hydrocarbons boiling in the range of about 170-250, 170-235, 170-230, 170-225, 180-250, 180-235, 180-230, 180-225, 190-250, 190-235, 190-230 or 190-225° C.

The term "heavy kerosene" as used herein refers to hydrocarbons boiling in the range of about 225-280, 225-270, 225-260, 230-280, 230-270, 230-260, 235-280, 235-270, 235-260 or 250-280° C.

The term "atmospheric gas oil" and its acronym "AGO" as used herein refer to hydrocarbons boiling in the range of about 250-370, 250-360, 250-340, 250-320, 260-370, 260-360, 260-340, 260-320, 270-370, 270-360, 270-340 or 270-320° C.

The term "heavy atmospheric gas oil" and its acronym "H-AGO" as used herein in certain embodiments refer to the heaviest cut of hydrocarbons in the AGO boiling range including the upper 3-30° C. range (e.g., for AGO having a range of about 250-360° C., the range of H-AGO includes an initial boiling point from about 330-357° C. and an end boiling point of about 360° C.).

The term "medium atmospheric gas oil" and its acronym "M-AGO" as used herein in certain embodiments in conjunction with H-AGO to refer to the remaining AGO after H-AGO is removed, that is, hydrocarbons in the AGO boiling range excluding the upper about 3-30° C. range (e.g., for AGO having a range of about 250-360° C., the range of M-AGO includes an initial boiling point of about 250° C. and an end boiling point of from about 330-357° C.).

In certain embodiments, the term "diesel" is used with reference to a straight run fraction from the atmospheric distillation unit. In embodiments in which this terminology is used, the diesel fraction refers to medium AGO range hydrocarbons and in certain embodiments also in combination with heavy kerosene range hydrocarbons.

The term "atmospheric residue" and its acronym "AR" as used herein refer to the bottom hydrocarbons having an initial boiling point corresponding to the end point of the AGO range hydrocarbons, and having an end point based on the characteristics of the crude oil feed.

The term "vacuum gas oil" and its acronym "VGO" as used herein refer to hydrocarbons boiling in the range of about 370-550, 370-540, 370-530, 370-510, 400-550, 400-540, 400-530, 400-510, 420-550, 420-540, 420-530 or 420-510° C.

The term "light vacuum gas oil" and its acronym "LVGO" as used herein refer to hydrocarbons boiling in the range of about 370-425, 370-415, 370-405, 370-395, 380-425, 390-425 or 400-425° C.

The term "heavy vacuum gas oil" and its acronym "HVGO" as used herein refer to hydrocarbons boiling in the range of about 425-550, 425-540, 425-530, 425-510, 450-550, 450-540, 450-530 or 450-510° C.

The term "vacuum residue" and its acronym "VR" as used herein refer to the bottom hydrocarbons having an initial boiling point corresponding to the end point of the VGO range hydrocarbons, and having an end point based on the characteristics of the crude oil feed.

The term "fuels" refers to crude oil-derived products used as energy carriers. Fuels commonly produced by oil refineries include, but are not limited to, gasoline, jet fuel, diesel fuel, fuel oil and petroleum coke. Unlike petrochemicals, which are a collection of well-defined compounds, fuels typically are complex mixtures of different hydrocarbon compounds.

The terms "kerosene fuel" or "kerosene fuel products" refer to fuel products used as energy carriers, such as jet fuel or other kerosene range fuel products (and precursors for producing such jet fuel or other kerosene range fuel products). Kerosene fuel includes but is not limited to kerosene fuel products meeting Jet A or Jet A-1 jet fuel specifications.

The terms "diesel fuel" and "diesel fuel products" refer to fuel products used as energy carriers suitable for compression-ignition engines (and precursors for producing such fuel products). Diesel fuel includes but is not limited to ultra-low sulfur diesel compliant with Euro V diesel standards.

The term "aromatic hydrocarbons" or "aromatics" is very well known in the art. Accordingly, the term "aromatic hydrocarbon" relates to cyclically conjugated hydrocarbons with a stability (due to delocalization) that is significantly greater than that of a hypothetical localized structure (e.g., Kekule structure). The most common method for determining aromaticity of a given hydrocarbon is the observation of diatropicity in its 1H NMR spectrum, for example the presence of chemical shifts in the range of from 7.2 to 7.3 ppm for benzene ring protons.

The terms "naphthenic hydrocarbons" or "naphthenes" or "cycloalkanes" are used herein having their established meanings and accordingly relates to types of alkanes that have one or more rings of carbon atoms in the chemical structure of their molecules.

The term "wild naphtha" is used herein to refer to naphtha products derived from hydroprocessing units such as distillate hydroprocessing units, diesel hydroprocessing units and/or gas oil hydroprocessing units.

The term "unconverted oil" and its acronym "UCO," is used herein having its known meaning, and refers to a highly paraffinic fraction from a hydrocracker with a low nitrogen, sulfur and nickel content and including hydrocarbons having an initial boiling point corresponding to the end point of the AGO range hydrocarbons, in certain embodiments the initial boiling point in the range of about 340-370° C., for instance about 340, 360 or 370° C., and an end point in the range of about 510-560° C., for instance about 540, 550 or 560° C. UCO is also known in the industry by other synonyms including "hydrowax."

The terms "reformate" or "chemical reformate" as used herein refer to a mixture of hydrocarbons that are rich in aromatics, and are intermediate products in the production of chemicals and/or gasoline, and include hydrocarbons boiling in the range of about 30-200, 40-200, 30-185, 40-185, 30-170 or 40-170° C.

The term "C# hydrocarbons" or "C#", is used herein having its well-known meaning, that is, wherein "#" is an integer value, and means hydrocarbons having that value of carbon atoms. The term "C#+ hydrocarbons" or "C#+" refers to hydrocarbons having that value or more carbon atoms. The term "C#-hydrocarbons" or "C#-" refers to hydrocarbons having that value or less carbon atoms. Similarly, ranges are also set forth, for instance, C1-C3 means a mixture comprising C1, C2 and C3.

The term "petrochemicals" or "petrochemical products" refers to chemical products derived from crude oil that are not used as fuels. Petrochemical products include olefins and aromatics that are used as a basic feedstock for producing chemicals and polymers. Typical olefinic petrochemical products include, but are not limited to, ethylene, propylene, butadiene, butylene-1, isobutylene, isoprene, cyclopentadiene and styrene. Typical aromatic petrochemical products include, but are not limited to, benzene, toluene, xylene, and ethyl benzene.

The term "olefin" is used herein having its well-known meaning, that is, unsaturated hydrocarbons containing at least one carbon-carbon double bond. In plural, the term "olefins" means a mixture comprising two or more unsaturated hydrocarbons containing at least one carbon-carbon double bond. In certain embodiments, the term "olefins" relates to a mixture comprising two or more of ethylene, propylene, butadiene, butylene-1, isobutylene, isoprene and cyclopentadiene.

The term "BTX" as used herein refers to the well-known acronym for benzene, toluene and xylenes.

The term "make-up hydrogen" is used herein with reference to hydroprocessing zones to refer to hydrogen requirements of the zone that exceed recycle from conventionally integrated separation vessels; in certain embodiments as used herein all or a portion of the make-up hydrogen in any given hydroprocessing zone or reactor within a zone is from gases derived from the steam cracking zone(s) and the reforming zone(s) in the integrated processes and systems.

The term "crude to chemicals conversion" as used herein refers to conversion of crude oil into petrochemicals including but not limited to lower olefins such as ethylene, propylene, butylenes (including isobutylene), butadiene, MTBE, butanols, benzene, ethylbenzene, toluene, xylenes, and derivatives of the foregoing.

The term "crude to chemicals conversion ratio" as used herein refers to the ratio, on a mass basis, of the influent crude oil before desalting, to petrochemicals.

The term "crude C4" refers to the mixed C4 effluent from a steam cracking zone.

The term "C4 Raffinate 1" or "C4 Raff-1" refers to the mixed C4s stream leaving the butadiene extraction unit, that is, mixed C4s from the crude C4 except butadiene.

The term "C4 Raffinate 2" or "C4 Raff-2" refers to the mixed C4s stream leaving the MTBE unit, that is, mixed C4s from the crude C4 except butadiene and isobutene.

The term "C4 Raffinate 3" or "C4 Raff-3" refers to the mixed C4s stream leaving the C4 distillation unit, that is, mixed C4s from the crude C4 except butadiene, isobutene, and butane-1.

The terms "pyrolysis gasoline" and its abbreviated form "py-gas" are used herein having their well-known meaning, that is, thermal cracking products in the range of C5 to C9, for instance having an end boiling point of about 204.4° C. (400° F.), in certain embodiments up to about 148.9° C. (300° F.).

The terms "pyrolysis oil" and its abbreviated form "py-oil" are used herein having their well-known meaning, that is, a heavy oil fraction, C10+, that is derived from steam cracking.

The terms "light pyrolysis oil" and its acronym "LPO" as used herein in certain embodiments refer to pyrolysis oil having an end boiling point of about 440, 450, 460 or 470° C.

The terms "heavy pyrolysis oil" and its acronym "HPO" as used herein in certain embodiments refer to pyrolysis oil having an initial boiling point of about 440, 450, 460 or 470° C.

The term "light cycle oil" and its acronym "LCO" as used herein refers to the light cycle oil produced by fluid catalytic cracking units. The distillation cut for this stream is, for example, in the range of about 220-330° C. LCO is used sometimes in the diesel blends depending on the diesel specifications, or it can be utilized as a cutter to the fuel oil tanks for a reduction in the viscosity and sulfur contents.

The term "heavy cycle oil" and its acronym "HCO" as used herein refer to the heavy cycle oil which is produced by fluid catalytic cracking units. The distillation cut for this stream is, for example, in the range of about 330-510° C. HCO is used sometimes in an oil flushing system within the process. Additionally, HCO is used to partially vaporize the debutanizer bottoms and then is recycled back as a circulating reflux to the main fractionator in the fluid catalytic cracking unit.

The term "cycle oil" is used herein to refer to a mixture of LCO and HCO.

In general, the integrated process for producing petrochemicals and fuel products from a crude oil feed includes an initial separation step to separate from a crude oil feed in an atmospheric distillation zone at least a first atmospheric distillation zone fraction comprising straight run naphtha; a second atmospheric distillation zone fraction comprising at least a portion of the middle distillates, and a third atmospheric distillation zone fraction comprising atmospheric residue. A first vacuum distillation zone fraction comprising vacuum gas oil is separated from the third atmospheric distillation zone fraction in a vacuum distillation zone. In a distillate hydroprocessing ("DHP") zone, such as a diesel hydrotreater, at least a portion of the second atmospheric distillation zone fraction is processed to produce at least a first DHP fraction and a second DHP fraction, wherein the first DHP fraction comprises naphtha and the second DHP fraction is used for diesel fuel production The first vacuum distillation zone fraction is processed in a fluid catalytic cracking zone to produce at least a first fluid catalytic cracking fraction corresponding to light olefins, a portion of which are recovered as petrochemicals, a second fluid catalytic cracking fraction corresponding to fluid catalytic cracking naphtha and a third fluid catalytic cracking fraction corresponding to cycle oil.

The light components such as LPG from the atmospheric distillation zone, and an aromatics extraction zone raffinate, are processed in a mixed feed steam cracking zone. All or a portion of the straight run naphtha is passed to a catalytic reforming zone to produce chemical rich reformate as additional feed to the aromatics extraction zone. The products from the mixed feed steam cracking zone include a mixed product stream containing $H_2$, methane, ethane, ethylene, mixed C3s, and mixed C4s, a pyrolysis gasoline stream and a pyrolysis oil stream.

From the mixed product stream, hydrogen gas, fuel gas, and petrochemicals ethylene, propylene and butylenes are recovered. Ethane and non-olefinic C3s and C4s are recovered, with ethane and non-olefinic C3s recycled to the steam cracking complex, and non-olefinic C4s are recycled to the steam cracking complex or passed to a separate processing zone for production of additional petrochemicals such as propylene and/or mixed butanol liquids. Pyrolysis gasoline is treated in a py-gas hydroprocessing zone to produce hydrotreated pyrolysis gasoline that is routed to an aromatics extraction complex to recover aromatic petrochemicals and a raffinate, including pyrolysis gasoline raffinate that is recycled to the steam cracking complex. In certain embodiments, fluid catalytic cracking naphtha is also hydroprocessed and passed to the aromatics extraction complex to produce additional aromatic petrochemicals and additional raffinate that is routed to the steam cracking complex.

Figure 2:
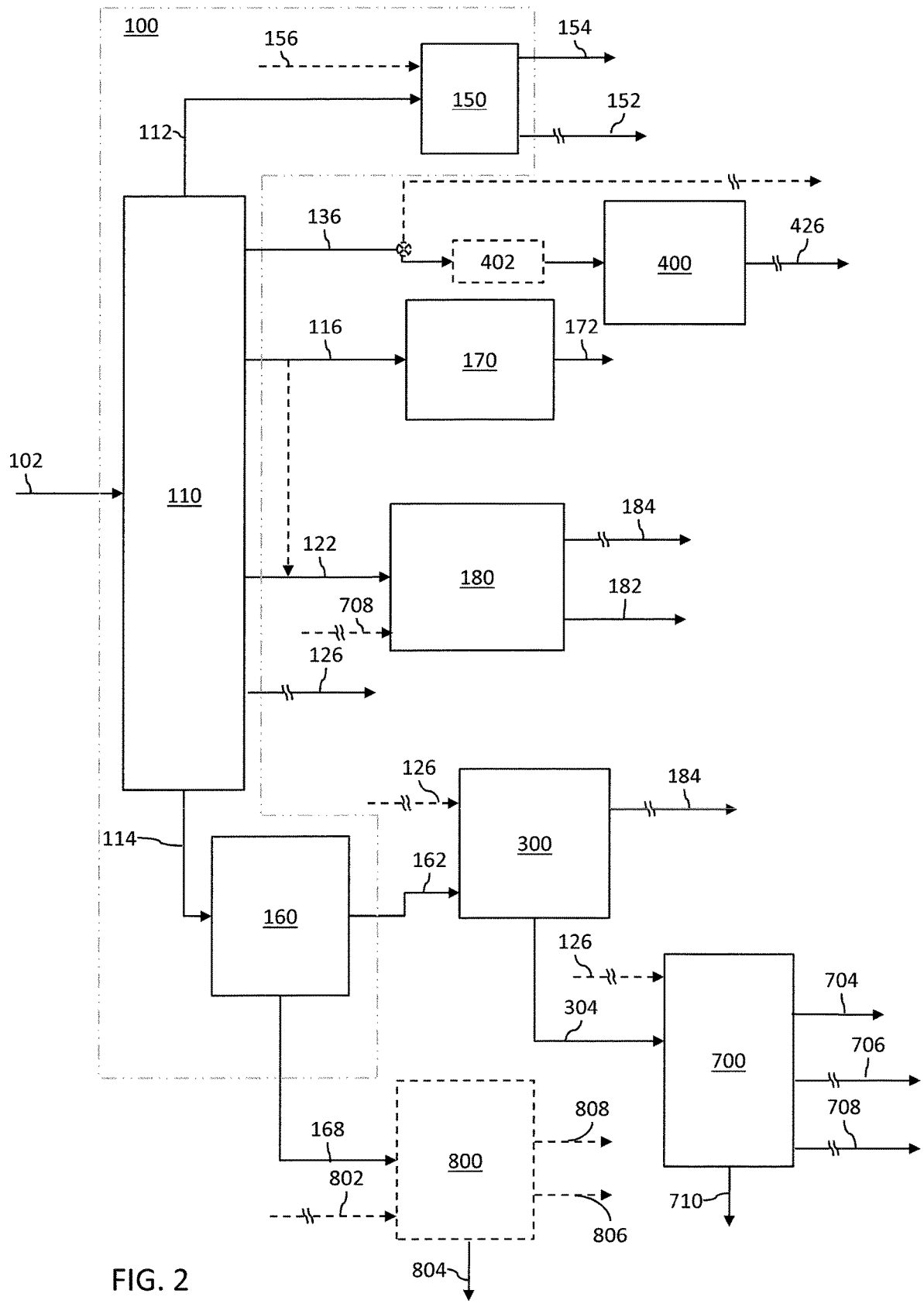
FIG. 2 schematically depicts operations upstream of a steam cracker complex in further embodiments of processes for producing petrochemicals and fuel products integrating fluid catalytic cracking and steam cracking.
Figure 3:
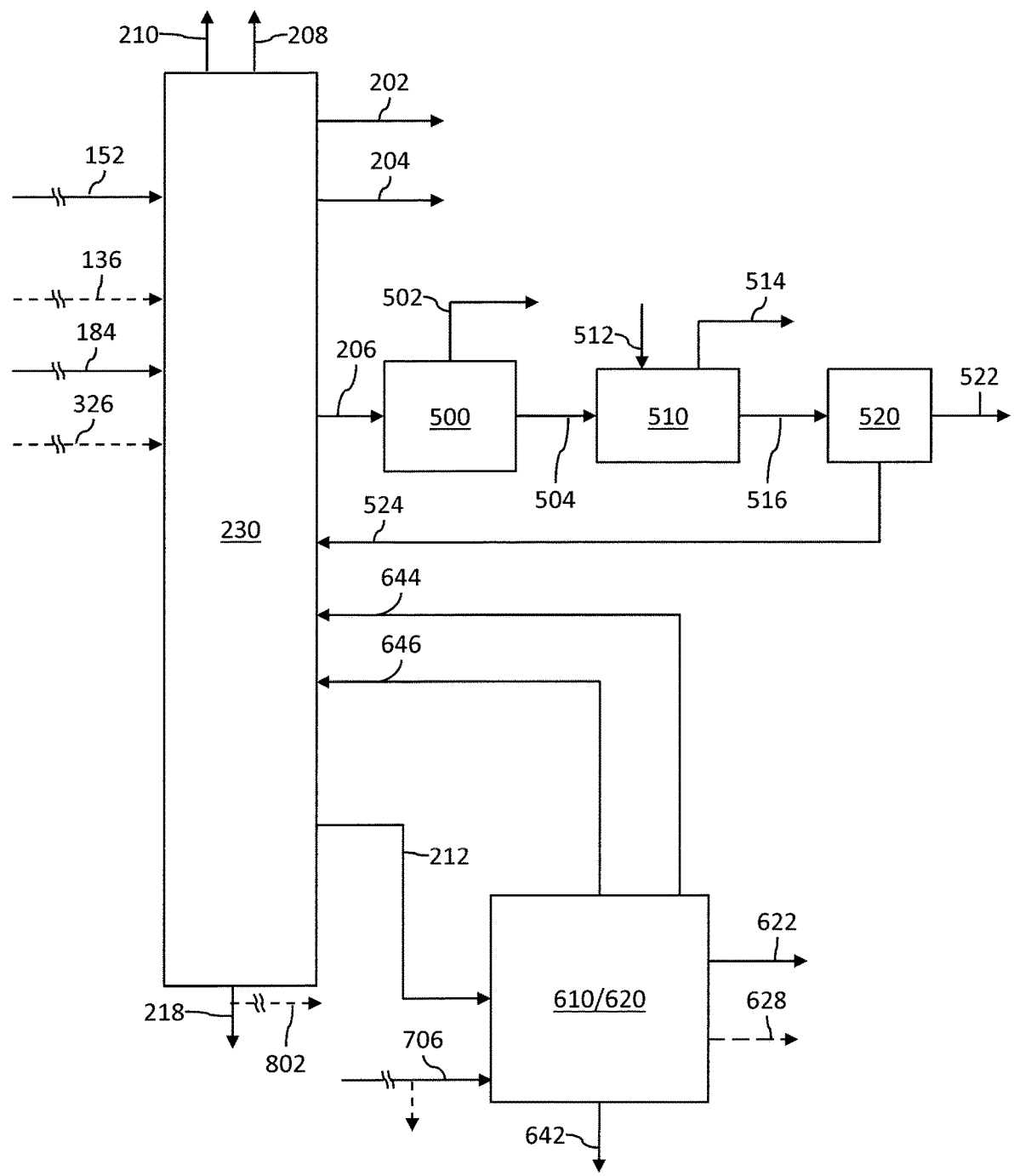
FIG. 3 schematically depicts operations downstream of and including a steam cracker complex in embodiments of processes for producing petrochemicals and fuel products integrating fluid catalytic cracking and steam cracking.

FIGS. 1, 2 and 3 schematically depict embodiments of processes and systems for conversion of crude oil to petrochemicals and fuel products, including a mixed feed steam cracking zone, a chemical reforming zone and a high olefinic fluid catalytic cracking (HOFCC) zone 700. Generally, FIGS. 1 and 2 show operations upstream of a mixed feed steam cracking zone (MFSC) 230 while FIG. 3 shows operations downstream of the crude oil conversion zone and including the mixed feed steam cracking zone 230. The integrated processes and systems include a vacuum gas oil hydroprocessing zone, which can operate as a vacuum gas oil hydrocracker 320 as shown in FIG. 1 or as a vacuum gas oil hydrotreater 300 as shown in FIG. 2.

With reference to FIGS. 1 and 2, a crude oil feed 102, in certain embodiments AXL or AL, is separated into fractions in a crude complex 100 typically including an atmospheric distillation zone (CDU) 110, a saturated gas plant 150 and a vacuum distillation zone 160. The crude oil feed 102, in certain embodiments having LPG and light naphtha removed, is separated into fractions the atmospheric distillation zone 110. As shown in FIG. 1, light products, for instance, light hydrocarbons with fewer than six carbons, are passed to the mixed feed steam cracking zone 230. In particular, C2-C4 hydrocarbons 152 including ethane, propane and butanes are separated from the light ends and LPG 112 from the atmospheric distillation zone 110 via the saturated gas plant 150. Optionally, other light products are routed to the saturated gas plant 150 shown in dashed lines as stream 156, such as light gases from refinery units within the integrated system and in certain embodiments, light gases from outside of the battery limits. Off-gases from the fluid catalytic cracking unit, after passing through an unsaturated gas plant, can be integrated with off-gases from the saturated gas plant 150 for common handling of the fuel gases.

The separated C2-C4 hydrocarbons 152 are routed to the mixed feed steam cracking zone 230. Off-gases 154 from the saturated gas plant 150 and off-gases 208 from the mixed feed steam cracking zone 230 are removed and recovered as is typically known, for instance to contribute to a fuel gas ("FG") system.

Straight run naphtha 136 from the atmospheric distillation zone 110 is passed to a catalytic reforming zone 400 to produce chemical rich reformate 426. In certain embodiments, all, a substantial portion or a significant portion of the straight run naphtha 136 is routed to the catalytic reforming zone 400. Remaining naphtha (if any) can be routed to the mixed feed steam cracking zone 230 (as shown in dashed lines) and/or added to a gasoline pool. In addition, in certain embodiments the straight run naphtha stream 136 contains naphtha from other sources as described herein and sometimes referred to as wild naphtha, for instance, naphtha range hydrocarbons from one or more of the integrated distillate, gas oil and/or residue hydroprocessing units.

Furthermore, in certain embodiments, an optional diverter, shown as a valve and a stream indicated in dashed lines, is used to bypass the catalytic reforming zone 400 and route all or a portion of the straight run naphtha (full range, light naphtha, or heavy naphtha) directly the mixed feed steam cracking zone 230. In this manner, a producer can vary the quantity of feed to tailor the desired outputs. Accordingly, all or a portion of the straight run naphtha can be routed to the catalytic reforming zone 400, and the remainder (if any) is directed to the mixed feed steam cracking zone 230. The quantity can be determined, for instance, based upon demand for olefinic petrochemicals, demand for aromatic petrochemicals, demand for gasoline, and/or minimum ranges for which the unit is operated depending on design capacity.

Middle distillates are used to produce diesel and/or kerosene, and additional feed to the mixed feed steam cracking zone 230. In the embodiments shown in FIGS. 1 and 2, at least three different middle distillate cuts are processed for production of fuel products and petrochemicals (via the steam cracker). In one example using the arrangements shown in FIGS. 1 and 2, a first atmospheric distillation zone middle distillate fraction 116, in certain embodiments referred to a kerosene fraction, contains light kerosene range hydrocarbons, a second atmospheric distillation zone middle distillate fraction 122, in certain embodiments referred as a diesel fraction, contains heavy kerosene range hydrocarbons and medium AGO range hydrocarbons, and a third atmospheric distillation zone middle distillate fraction 126, in certain embodiments referred to as an atmospheric gas oil fraction, contains heavy AGO range hydrocarbons. In another example using the arrangements shown in FIGS. 1 and 2, a first middle distillate fraction 116 contains kerosene range hydrocarbons, a second middle distillate fraction 122 contains medium AGO range hydrocarbons and a third middle distillate fraction 126 contains heavy AGO range hydrocarbons. In another example using the arrangements shown in FIGS. 1 and 2, a first middle distillate fraction 116 contains light kerosene range hydrocarbons and a portion of heavy kerosene range hydrocarbons, a second middle distillate fraction 122 contains a portion of heavy kerosene range hydrocarbons and a portion of medium AGO range hydrocarbons and a third middle distillate fraction 126 contains a portion of medium AGO range hydrocarbons and heavy AGO range hydrocarbons.

For example, a first middle distillate fraction 116 can be processed in a kerosene sweetening process 170 to produce kerosene fuel product 172, for instance, jet fuel compliant with Jet A or Jet A-1 specifications, and optionally other fuel products (not shown). In certain embodiments herein, all or a portion of the first middle distillate fraction 116 is not used for fuel production, but rather is used as a feed for distillate hydroprocessing so as to produce additional feed for the mixed feed steam cracking zone 230.

A second middle distillate fraction 122 is processed in a distillate hydroprocessing zone such as a diesel hydrotreating zone 180, to produce wild naphtha 184 and a diesel fuel fraction 182, for instance, compliant with Euro V diesel standards. In additional embodiments, all or a portion of the first middle distillate fraction 116 can be treated with the second middle distillate fraction 122, as denoted by dashed lines.

In certain embodiments, all, a substantial portion, a significant portion or a major portion of the wild naphtha 184 is routed to the mixed feed steam cracking zone 230 alone, or in combination with other wild naphtha fractions from within the integrated process; any portion that is not passed to the mixed feed steam cracking zone 230 can be routed to the crude complex 100 and/or directly to the catalytic reforming zone 400 and/or to a gasoline pool. In further embodiments, all, a substantial portion, a significant portion or a major portion of the wild naphtha 184 is passed to the crude complex 100, alone, or in combination with other wild naphtha fractions from within the integrated process; any portion that is not passed to the crude complex 100 can be routed to the mixed feed steam cracking zone 230 and/or directly to the catalytic reforming zone 400 and/or to a gasoline pool. In additional embodiments, all, a substantial portion, a significant portion or a major portion of the wild naphtha 184 is passed to the catalytic reforming zone 400, alone, or in combination with other wild naphtha fractions from within the integrated process; any portion that is not passed to the catalytic reforming zone 400 can be routed to the mixed feed steam cracking zone 230 and/or to the crude complex 100 and/or to a gasoline pool. In embodiments in which wild naphtha 184 is routed through the crude complex 100, all or a portion of the liquefied petroleum gas produced in the vacuum gas oil hydroprocessing zone can be passed with the wild naphtha.

In certain embodiments (as denoted by dashed lines), all, a substantial portion, a significant portion or a major portion of the third middle distillate fraction 126 is routed to the vacuum gas oil hydroprocessing zone in combination with the vacuum gas oil stream 162; any portion that is not passed to the vacuum gas oil hydroprocessing zone can be routed to the high olefinic fluid catalytic cracking zone 700, bypassing the vacuum gas oil hydroprocessing zone. In further embodiments (as denoted by dashed lines), all, a substantial portion, a significant portion or a major portion of the third middle distillate fraction 126 is routed to the high olefinic fluid catalytic cracking zone 700, bypassing the vacuum gas oil hydroprocessing zone; any portion that is not passed to the high olefinic fluid catalytic cracking zone 700 can be routed to the vacuum gas oil hydroprocessing zone.

An atmospheric residue fraction 114 from the atmospheric distillation zone 110 is further separated in the vacuum distillation zone 160. Vacuum gas oil 162 from the vacuum distillation zone 160 is routed to the vacuum gas oil hydroprocessing zone. The heaviest fraction 168 from the vacuum distillation zone 160, vacuum residue, can be sent to a fuel oil ("FO") pool or optionally processed in a residue treatment zone 800, shown in dashed lines. In certain embodiments, a minor portion of the atmospheric residue fraction 114 can bypass the vacuum distillation zone 160 (not shown) and is routed to the optional residue treating zone 800.

In certain embodiments, all, a substantial portion, a significant portion or a major portion of the vacuum gas oil 162 is routed to the vacuum gas oil hydroprocessing zone. Any portion that is not hydroprocessed can be routed to the high olefinic fluid catalytic cracking zone 700. As shown in FIG. 1, vacuum gas oil hydroprocessing is in a vacuum gas oil hydrocracking zone 320 that can operate under mild, moderate or severe hydrocracking conditions, and generally produces a hydrocracked naphtha fraction 326, a diesel fuel fraction 322, and an unconverted oil fraction 324. The diesel fuel fraction 322 is recovered as fuel, for instance, compliant with Euro V diesel standards, and can be combined with the diesel fuel fraction 182 from the diesel hydrotreating zone 180. As shown in FIG. 2, vacuum gas oil hydroprocessing is in a vacuum gas oil hydrotreating zone 300 that can operate under mild, moderate or severe hydrotreating conditions, and generally produces a hydrotreated gas oil fraction 304, naphtha and some middle distillates. Naphtha range products can be separated from products within the vacuum gas oil hydrotreating zone 300 as a hydrotreated naphtha stream 306. Alternatively, or in conjunction with the hydrotreated naphtha stream 306, a cracked distillates stream 308 containing hydrotreated distillates (and in certain embodiments naphtha range products) are routed to diesel hydrotreating zone 180 for further hydroprocessing and/or separation into diesel hydrotreating zone 180 products.

In certain embodiments, all, a substantial portion, a significant portion or a major portion of the wild naphtha fraction from the vacuum gas oil hydroprocessing zone, streams 326 or 306, is routed to the mixed feed steam cracking zone 230, alone, or in combination with other wild naphtha fractions from within the integrated process; any portion that is not passed to the mixed feed steam cracking zone 230 can be routed to the crude complex 100 and/or directly to the catalytic reforming zone 400 and/or to the gasoline pool. In further embodiments, all, a substantial portion, a significant portion or a major portion of the wild naphtha fraction from the vacuum gas oil hydroprocessing zone is passed to the crude complex 100, alone, or in combination with other wild naphtha fractions from within the integrated process; any portion that is not passed to the crude complex 100 can be routed to the mixed feed steam cracking zone 230 and/directly to the catalytic reforming zone 400 and/or to the gasoline pool. In additional embodiments, all, a substantial portion, a significant portion or a major portion of the wild naphtha fraction from the vacuum gas oil hydroprocessing zone is passed to the catalytic reforming zone 400, alone, or in combination with other wild naphtha fractions from within the integrated process; any portion that is not passed to the catalytic reforming zone 400 can be routed to the mixed feed steam cracking zone 230 and/or to the crude complex 100 and/or to the gasoline pool. In embodiments in which wild naphtha from the vacuum gas oil hydroprocessing zone is routed through the crude complex 100, all or a portion of the liquefied petroleum gas produced in the vacuum gas oil hydroprocessing zone can be passed with the wild naphtha.

Heavy product from the vacuum gas oil hydroprocessing zone is routed to the high olefinic fluid catalytic cracking zone 700. In the embodiments with the vacuum gas oil hydrotreating zone 300, heavy product is the hydrotreated gas oil fraction 304 that contains the portion of the vacuum gas oil hydrotreater 300 effluent that is at or above the AGO, H-AGO or VGO boiling range. In the embodiments with the vacuum gas oil hydrocracking zone 320, heavy product is the unconverted oil fraction 324. All, a substantial portion, a significant portion or a major portion of heavy product from the vacuum gas oil hydroprocessing zone is routed to high olefinic fluid catalytic cracking zone 700. The remainder (if any) can be passed to the optional vacuum residue treating zone 800 and/or passed to the mixed feed steam cracking zone 230. Alternatively, any remainder can be recycled and further processed (cracked to extinction in VGO hydrocracking) and/or bled from the system and/or passed to the optional residue treating zone 800.

The high olefinic fluid catalytic cracking zone 700 is configured to produce light olefin product 704 and high olefinic fluid catalytic cracking naphtha 706. It should be appreciated that the light olefin product 704 can be recovered from the high olefinic fluid catalytic cracking zone 700 as is known, or recovered in combination with the olefins recovery zone 270 and/or the mixed feed steam cracking zone 230 as described herein. Off-gases from the high olefinic fluid catalytic cracking zone 700 can be integrated with the fuel gas system. In certain embodiments (not shown in FIG. 1), certain gases, after treatment in an unsaturated gas plant, can be routed to the separation units associated with the mixed feed steam cracking zone 230, and/or LPGs can be routed to the mixed feed steam cracking zone 230. All, a substantial portion, a significant portion or a major portion of the gases containing light olefins (a C2− stream and a C3+ stream) are routed through the unsaturated gas plant. The remainder, if any, can be routed to the mixed feed steam cracking zone 230 and/or the olefins recovery train 270.

In certain embodiments, all or a portion of the high olefinic fluid catalytic cracking naphtha 706 can be processed as described below (and in conjunction with FIG. 3) in a naphtha hydrotreatment and recovery center 610/620, to increase the quantity of raffinate as additional feed to the mixed feed steam cracking zone 230. Any portion of the high olefinic fluid catalytic cracking naphtha 706 that is not routed to the naphtha hydrotreatment and recovery center 610/620, shown in dashed lines, is hydrotreated and recovered for fuel production (not shown). For instance, in modalities in which the objective is maximum petrochemical production, all, a substantial portion, a significant portion or a major portion of the fluid catalytic cracking naphtha 706 is routed to the naphtha hydrotreatment and recovery center 610/620; the remainder, if any, is recovered for fuel production and incorporation into a gasoline pool.

Figure 4:
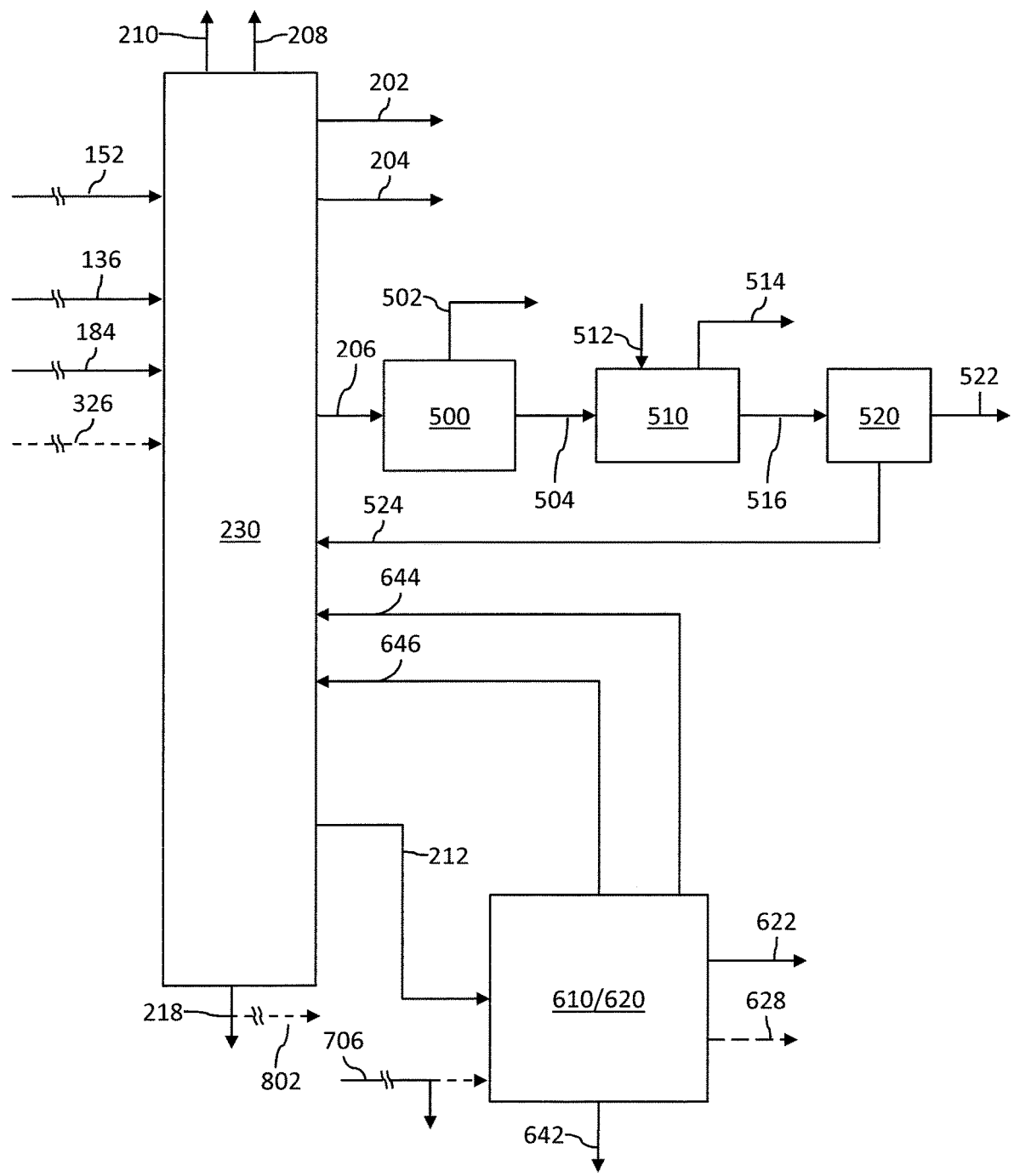
FIG. 4 schematically depicts operations downstream of and including a steam cracker complex in further embodiments of processes for producing petrochemicals and fuel products integrating fluid catalytic cracking and steam cracking.

In additional embodiments, as shown in FIG. 4, all or a portion of the high olefinic fluid catalytic cracking naphtha 706 is hydrotreated and recovered for fuel production and incorporation into a gasoline pool (not shown). Optionally, a portion of the high olefinic fluid catalytic cracking naphtha 706 that is not recovered for fuel production can be processed in the naphtha hydrotreatment and recovery center 610/620, as shown in dashed lines, to increase the quantity of raffinate as additional feed to the mixed feed steam cracking zone 230.

Figure 5:
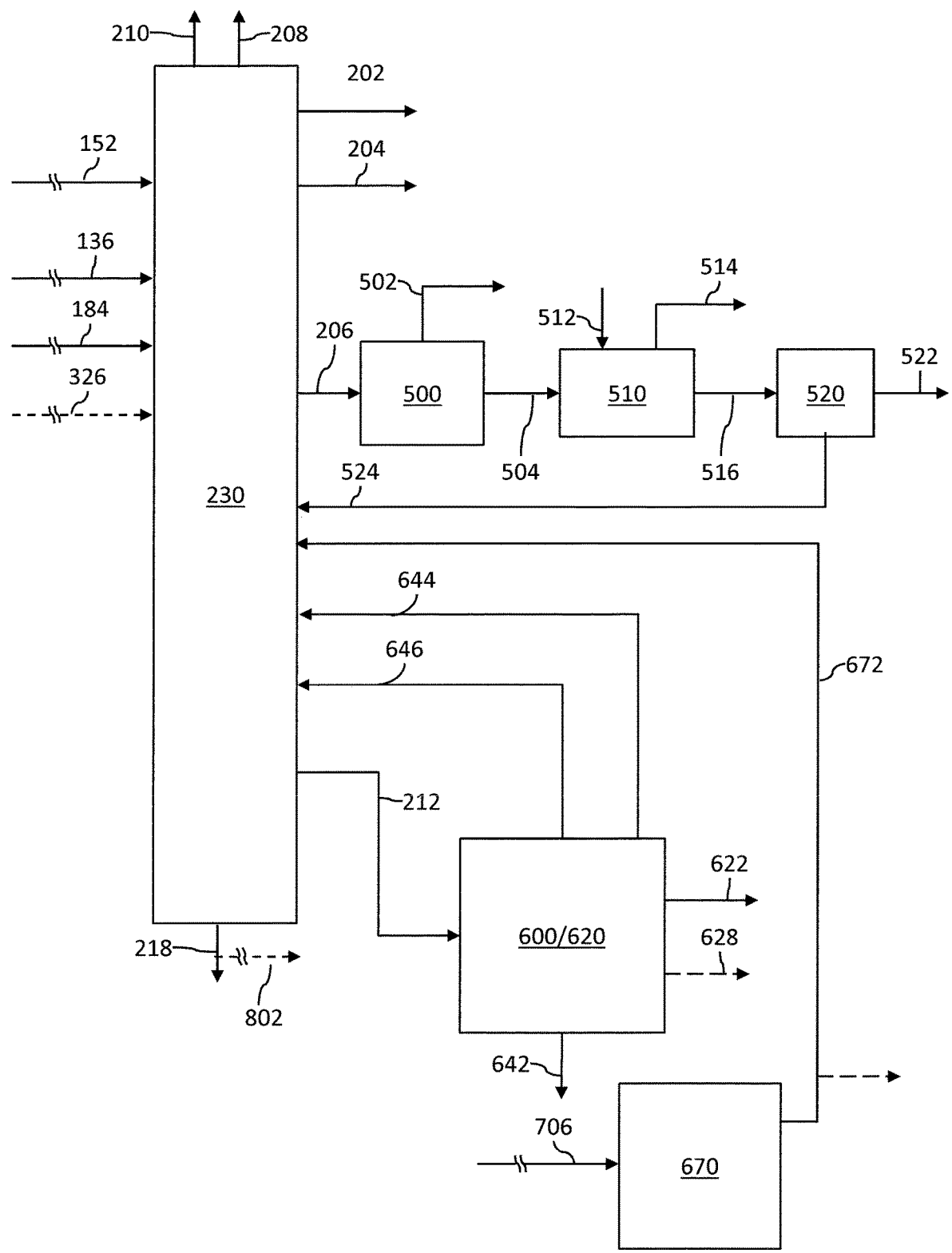
FIG. 5 schematically depicts operations downstream of and including a steam cracker complex in further embodiments of processes for producing petrochemicals and fuel products integrating fluid catalytic cracking and steam cracking.

In additional embodiments, as shown in FIG. 5, all or a portion of the high olefinic fluid catalytic cracking naphtha 706 is hydrotreated in a fluid catalytic cracking naphtha hydrotreating zone 670, and the hydrotreated fluid catalytic cracking naphtha stream 672 is directly routed to the mixed feed steam cracking zone 230. Any portion of the high olefinic fluid catalytic cracking naphtha 706 that is not routed to the to the mixed feed steam cracking zone 230, shown in dashed lines, is recovered for fuel production (not shown). In this manner, components of the hydrotreated fluid catalytic cracking naphtha stream 672, that are not cracked in the mixed feed steam cracking zone 230, including aromatics, increase the pyrolysis gasoline 212 from the mixed feed steam cracking zone 230, which are routed to the py-gas hydrotreatment and recovery center 600/620. In certain embodiments using the fluid catalytic cracking naphtha hydrotreating zone 670, all, a substantial portion, a significant portion or a major portion of the hydrotreated fluid catalytic cracking naphtha stream 672 is routed to the mixed feed steam cracking zone 230; the remainder, if any, can be routed to aromatics extraction 620 and/or recovered for fuel production and incorporation into a gasoline pool and/or passed to the chemical reforming zone 400. In additional embodiments using the fluid catalytic cracking naphtha hydrotreating zone 670, all, a substantial portion, a significant portion or a major portion of the hydrotreated fluid catalytic cracking naphtha stream 672 is routed to the chemical reforming zone 400, the remainder, if any, can be routed to aromatics extraction 620 and/or recovered for fuel production and incorporation into a gasoline pool and/or passed to the mixed feed steam cracking zone 230.

Other products from the high olefinic fluid catalytic cracking zone 700 include cycle oil, such as light cycle oil 708 and heavy cycle oil 710. In certain optional embodiments, all or a portion of the light cycle oil 708 is routed to the distillate hydroprocessing zone 180, thereby increasing the yield of the diesel fuel fraction 182 and wild naphtha 184 that is passed to the mixed feed steam cracking zone 230. In certain embodiments, all, a substantial portion, a significant portion or a major portion of the light cycle oil 708 is passed to the distillate hydroprocessing zone 180, and any remaining portion can be routed to the vacuum gas oil processing zone. Heavy cycle oil stream 710 can be routed to a fuel oil pool or used as feedstock for production of carbon black.

With reference to FIG. 3, the mixed feed steam cracking zone 230, which operates as a high severity or low severity thermal cracking process, converts its feed primarily into ethylene 202, propylene 204, mixed C4s 206, pyrolysis gasoline 212, pyrolysis oil 218, and off-gases 208 that can be passed to an integrated fuel gas system. Further, hydrogen 210 is recovered from the cracked products and can be recycled to hydrogen users within the complex limits. Not shown are the ethane and propane recycle, which are typical in steam cracking operations, although it is appreciated that in certain embodiments all or a portion of the ethane and propane can be diverted. In certain embodiments, all, a substantial portion, a significant portion or a major portion of ethane is recycled to the mixed feed steam cracking zone 230, and all, a substantial portion, a significant portion or a major portion of propane is mixed feed steam cracking zone 230. In certain embodiments hydrogen for all hydrogen users in the integrated process and system is derived from hydrogen 210 recovered from the cracked products, and no outside hydrogen is required once the process has completed start-up and reached equilibrium. In further embodiments excess hydrogen can be recovered.

For simplicity, operations in an olefins recovery train are not shown, but are well known and are considered part of the mixed feed steam cracking zone 230 as described herein with respect to FIGS. 3, 4, 5, 6, 7, 8 and 11.

The mixed C4s stream 206 containing a mixture of C4s from the mixed feed steam cracking zone 230, known as crude C4s, is routed to a butadiene extraction unit 500 to recover a high purity 1,3-butadiene product 502. A first raffinate 504 ("C4-Raff-1") containing butanes and butenes is passed to a selective hydrogenation unit (SHU) and methyl tertiary butyl ether ("MTBE") unit, SHU and MTBE zone 510, where it is mixed with high purity fresh methanol 512 from outside battery limits to produce MTBE 514.

A second raffinate 516 ("C4 Raff-2") from the SHU and MTBE zone 510 is routed to a C4 distillation unit 520 for separation into a 1-butene product stream 522 and an alkane stream 524 (a third raffinate "C4-Raff-3") containing residual C4s, all, a substantial portion, a significant portion or a major portion of which is recycled to the mixed feed steam cracking zone 230 although it is appreciated that in certain embodiments all or a portion of the residual C4s can be diverted. Separation of the ethylene 202, propylene 204 and the mixed C4s stream 206 occurs in a suitable arrangement of known separation steps for separating steam cracking zone effluents, including compression stage(s), depropanizer, debutanizer, demethanizer and deethanizer.

Pyrolysis gasoline 212 from the steam cracking zone 230 is fed to the naphtha hydrotreatment and recovery center 610/620. In certain embodiments, select hydrocarbons having 5-12 carbons are recovered from untreated pyrolysis gasoline and high olefinic fluid catalytic cracking naphtha ("FCCN") 706, and the remainder is subsequently hydrotreated for aromatics recovery. In the naphtha hydrotreating unit 610, diolefins and olefins in the pyrolysis gasoline are saturated. All, a substantial portion or a significant portion of the pyrolysis gasoline 212 from the steam cracking zone 230 is passed to the naphtha hydrotreatment and recovery center 610/620.

As noted above, in certain embodiments, all or a portion of the fluid catalytic cracking naphtha 706 is used as additional feed to the mixed feed steam cracking zone 230 without the hydrotreating and aromatic separation steps, without the aromatic separation step, or without the hydrotreating step. In further embodiments, all or a portion of the fluid catalytic cracking naphtha 706 is recovered and used for fuel production.

Hydrotreated pyrolysis gasoline and fluid catalytic cracking naphtha (in certain embodiments having C5s removed and recycled to the mixed feed steam cracking zone 230 instead of or in conjunction with C5s from the aromatics extraction zone 620) are routed to the aromatics extraction zone 620. The naphtha hydrotreating zone 610 and the aromatics extraction zone 620 high olefinic fluid catalytic are shown for simplicity in a single schematic block 610/620 in FIGS. 3, 4, 5, 6, 7, 8 and 11. The naphtha hydrotreating zone 610 operates to hydrotreat pyrolysis gasoline 212 prior to aromatics recovery. In certain optional embodiments, fluid catalytic cracking naphtha 706 can also be hydrotreated in a separate hydrotreating zone (shown, for instance, in FIGS. 5, 21 and 24), and routed to the aromatics extraction zone 620 with the hydrotreated pyrolysis gasoline.

In an embodiment herein, chemical rich reformate 426 is to be routed as additional feed to the aromatics extraction zone 620. The chemical rich reformate 426 can bypass naphtha hydrotreating, since it has been treated in the catalytic reforming zone 400, although in certain embodiments the chemical rich reformate 426 can pass with the pyrolysis gasoline and/or the FCC naphtha. In further embodiments, modes of operation are provided in which the chemical rich reformate 426 can serve as feed to the aromatics extraction zone 620 and/or as gasoline blending components. In this manner, a producer can vary the quantity of feed to tailor the desired outputs. Accordingly, 0-100% of the chemical rich reformate 426 can be routed to the aromatics extraction zone 620, and the remainder (if any) is directed to a gasoline blending pool (not shown). The quantity can be determined, for instance, based upon demand for aromatic petrochemicals, demand for gasoline, and/or minimum ranges for which the unit is operated depending on design capacity.

The aromatics extraction zone 620 includes, for instance, one or more extractive distillation units, and operates to separate the hydrotreated pyrolysis gasoline and fluid catalytic cracking naphtha into an aromatics stream 622 containing high-purity benzene, toluene, xylenes and C9 aromatics, which are recovered for chemical markets. C5 raffinate 644 and non-aromatics 646 (for instance, C6-C9) are recycled to the mixed feed steam cracking zone 230. In certain embodiments, all, a substantial portion or a significant portion of the C5 raffinate 644 and non-aromatics 646 are passed to the mixed feed steam cracking zone 230. A heavy aromatics stream 642 (for instance, C10-C12) can be used as an aromatic solvent, an octane boosting additive or as a cutter stock into a fuel oil pool. In certain embodiments ethylbenzene 628 can be recovered.

In certain embodiments, pyrolysis oil 218 can be blended into the fuel oil pool. In additional embodiments, pyrolysis oil 218 can be fractioned (not shown) into light pyrolysis oil and heavy pyrolysis oil. For instance, light pyrolysis oil can be blended with the first middle distillate stream 116 and/or the second middle distillate stream 122, for processing to produce diesel fuel product and/or additional feed to the mixed feed steam cracking zone 230. In further embodiments light pyrolysis oil derived from pyrolysis oil 218 can be processed in the vacuum gas oil hydroprocessing zone. In additional embodiments, light pyrolysis oil derived from pyrolysis oil 218 can be blended into the fuel oil pool. In further embodiments, light pyrolysis derived from pyrolysis oil 218 can be processed in the residue treating zone 800. In certain embodiments, all, a substantial portion, a significant portion or a major portion of light pyrolysis oil can be passed to the diesel hydrotreating zone 180 and/or the vacuum gas oil hydroprocessing zone; any remainder can be blended into the fuel oil pool. Heavy pyrolysis oil can be blended into the fuel oil pool, used as a carbon black feedstock and/or processed in the optional residue treating zone 800. In certain embodiments, all, a substantial portion, a significant portion or a major portion of the pyrolysis oil 218 (light and heavy) can be processed in the optional residue treating zone 800.

Figure 6:
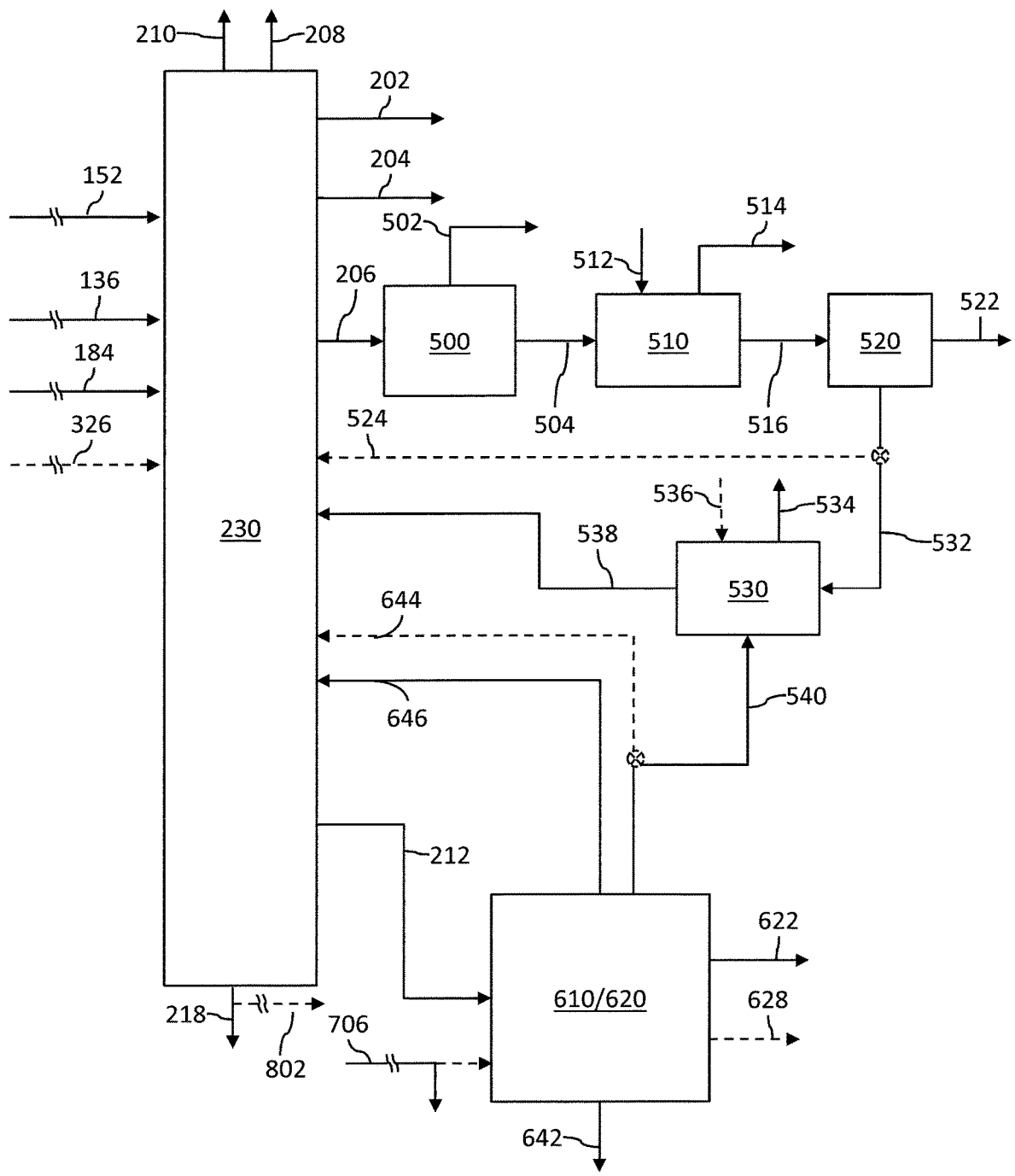
FIG. 6 schematically depicts operations downstream of and including a steam cracker complex in embodiments of processes for producing petrochemicals and fuel products integrating fluid catalytic cracking, steam cracking and metathesis.

FIG. 6 schematically depicts further embodiments of processes and systems for conversion of crude oil to petrochemicals and fuel products, with metathesis conversion of C4 and C5 olefins to produce additional propylene. The process operates as described with respect to any of FIG. 1, 2, 4 or 5 upstream of the steam cracking operations and with respect to the fluid catalytic cracking operations.

Downstream of the steam cracking operations, the butadiene extraction train can optionally operate in a manner similar to that in FIG. 3 shown as the stream 524 from a diverter (in dashed lines) from the C4 distillation unit 520 directly to the mixed feed steam cracking zone 230.

In a metathesis mode of operation, mixed C4 raffinate stream 532 ("C4 Raff 3") from the C4 distillation unit 520 and C5 raffinate 540 from the naphtha hydrotreatment and recovery center 610/620 are routed to the metathesis unit 530 for metathesis conversion to additional propylene 534. In certain embodiments, all, a substantial portion, a significant portion or a major portion of the cracked C5s from the py-gas hydrotreater can be routed to the metathesis unit 530 prior to aromatics extraction. As indicated, a portion 536 of the ethylene mixed feed steam cracking product 202 can be routed to the metathesis unit 530. In additional embodiments, ethylene for the metathesis unit 530 is supplied from outside the complex limits, instead of or in addition to the portion 536 of the ethylene mixed feed steam cracking product.

Selective recovery of various alkene and diene pyrolysis chemicals having four carbons, and metathesis conversion to produce additional propylene, is achieved using a metathesis unit 530. A stream 538 containing a mixture of mostly saturated C4/C5 from the metathesis unit 530 is recycled to the mixed feed steam cracking zone 230.

As in FIG. 3, in the configuration of FIG. 6, pyrolysis gasoline 212 from the steam cracking zone 230 is routed to the naphtha hydrotreatment and recovery center 610/620 where select hydrocarbons having 5-12 carbons can be recovered from untreated pyrolysis gasoline and fluid catalytic cracking naphtha, and the remainder is subsequently hydrotreated for aromatics recovery. In a py-gas hydrotreating unit ("HTU"), diolefins and olefins in the pyrolysis gasoline are saturated. In the aromatics extraction step, aromatics are separated from hydrotreated pyrolysis gasoline and fluid catalytic cracking naphtha. For instance, aromatic extraction can separate the hydrotreated pyrolysis gasoline and fluid catalytic cracking naphtha into high-purity benzene, toluene, xylenes and C9 aromatics. C6-C9 aromatics stream 622, BTX, is recovered for chemical markets, C6-C9 non-aromatics stream 646 is recycled to the mixed feed steam cracking zone 230, and C10-C12 products stream 642 may be used as an aromatic solvent or as an octane boosting additive. In certain embodiments ethylbenzene 628 can be recovered. C5 raffinate is routed to the metathesis unit 530 as shown as stream 540, and/or recycled to the mixed feed steam cracking zone 230 (as in the embodiment of FIG. 3) via stream 644, shown in dashed lines in FIG. 6.

In the configuration depicted in FIG. 6, an optional diverter is shown, indicated as a diverter and stream in dashed lines, to bypass the metathesis conversion process, to therefore divert all, a substantial portion, a significant portion or a major portion of the C4 Raff-3 524 to the mixed feed steam cracking zone 230. In a metathesis mode, flow can be directed to the metathesis conversion unit 530. In further alternative modes, flow of the C4 Raff-3 524 can be directed to the mixed feed steam cracking zone 230 and the metathesis conversion unit 530. In this manner, a producer can vary the quantity of feed to tailor the desired outputs. Accordingly, 0-100% of the third C4 raffinate stream 524 can be routed to the metathesis conversion unit 530, and the remainder (if any) is directed to the mixed feed steam cracking zone 230. The quantity can be determined, for instance, based upon demand for ethylene, demand for propylene, and/or minimum ranges for which the unit is operated depending on design capacity.

Figure 7:
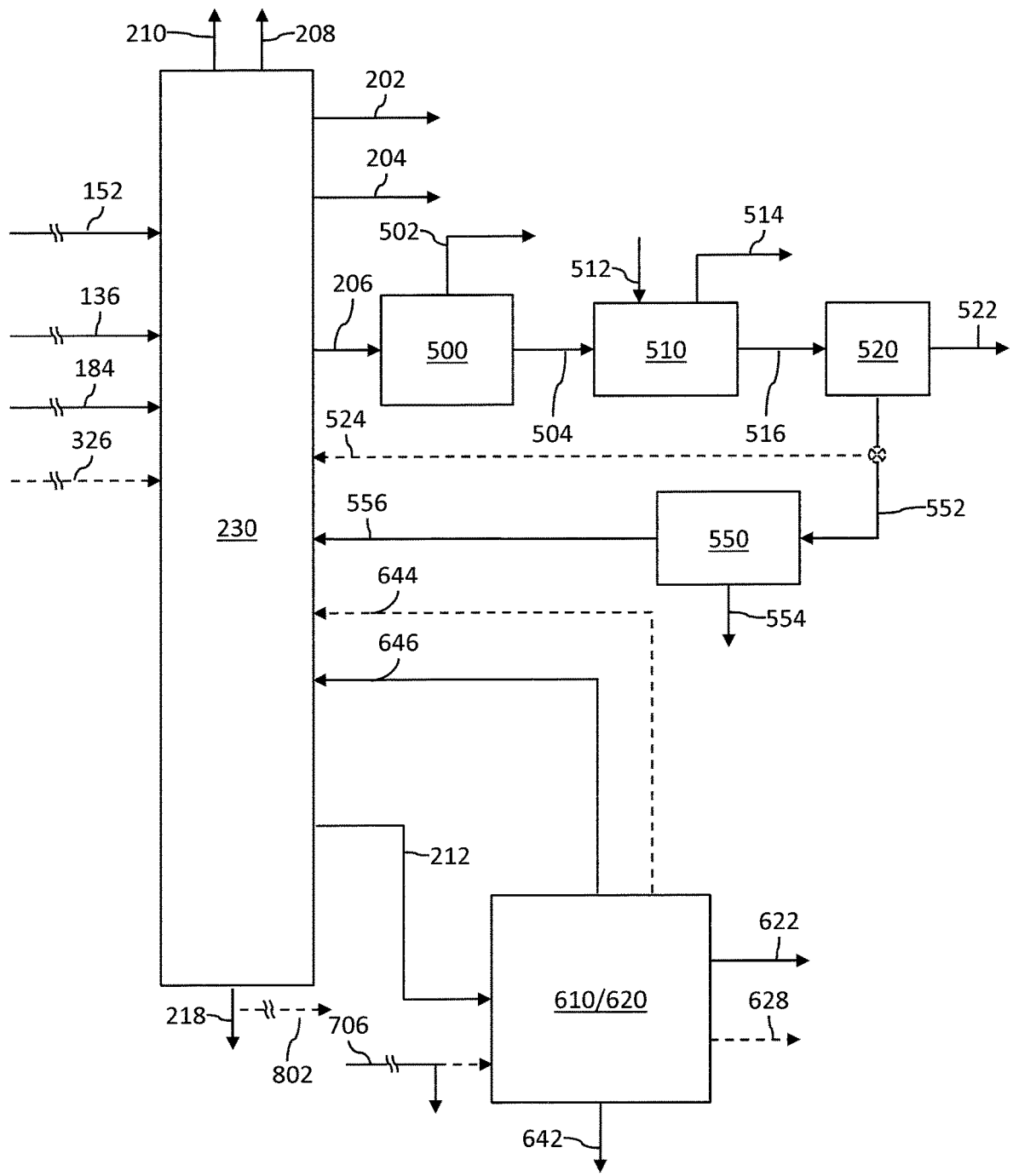
FIG. 7 schematically depicts operations downstream of and including a steam cracker complex in embodiments of processes for producing petrochemicals and fuel products integrating fluid catalytic cracking, steam cracking and mixed butanol production.

FIG. 7 schematically depicts further embodiments of processes and systems for conversion of crude oil to petrochemicals and fuel products. The process operates as described with respect to FIG. 1, 2, 4 or 5 upstream of the steam cracking operations and with respect to the fluid catalytic cracking operations. In this embodiment, an additional step is provided to convert a mixture of butenes into mixed butanols suitable as a gasoline blending oxygenate and for octane enhancement. Suitable processes to convert a mixture of butenes into mixed butanols are described in one or more commonly owned patent publications US20160115107A1, US20150225320A1, US20150148572A1, US20130104449A1, US20120245397A1 and commonly owned U.S. Pat. No. 9,447,346B2, U.S. Pat. No. 9,393,540B2, U.S. Pat. No. 9,187,388B2, U.S. Pat. No. 8,558,036B2, all of which are incorporated by reference herein in their entireties. In certain embodiments, a particularly effective conversion process known as "SuperButol™" technology is integrated, which is a one-step process that converts a mixture of butenes into mixed butanol liquids.

Downstream of the steam cracking operations, the butadiene extraction train can optionally operate in a manner similar to that in FIG. 3 shown as the stream 524 from a diverter (in dashed lines) from the C4 distillation unit 520 directly to the mixed feed steam cracking zone 230. A crude C4 processing center 550 is integrated for selective recovery of various alkene and diene pyrolysis chemicals having four carbons, and in certain processing arrangements hydrating a portion of those C4's in a butanol production unit (such as a "SuperButol™" unit) to produce high value fuel additives.

For instance, the mixed butanols production zone 550 operates to convert butenes to butanols from undervalued refinery/petrochemical mixed olefin streams. The butanols provide an alternative option for oxygenates in gasoline blends. The crude C4 processing center 550 includes the conversion reaction of butenes to butanols, for instance, in one or more high pressure catalytic reactors followed by gravity separation of butenes and butanols from water, and subsequent separation of the butanols product from butenes by distillation. Process stages include butenes and water make-up and recycle, butanol reaction, high pressure separation, low pressure separation, debutenizer distillation (product column) and an aqueous distillation column.

FIG. 7 depicts a stream 552 containing butenes from the C4 distillation step routed to a crude C4 processing zone such as a butanol production unit 550 to convert the mixture of butenes into mixed butanol liquids 554. In certain embodiments, all, a substantial portion, a significant portion or a major portion of stream 552 is routed to the butanol production unit 550. Alkanes 556 are recycled to the mixed feed steam cracking zone 230.

As in FIGS. 1 and 3, in the configuration of FIG. 7, pyrolysis gasoline 212 from the steam cracking zone 230 is routed to the naphtha hydrotreatment and recovery center 610/620 where select hydrocarbons having 5-12 carbons can be recovered from untreated pyrolysis gasoline and fluid catalytic cracking naphtha, and the remainder is subsequently hydrotreated for aromatics recovery. C5s are recycled to the mixed feed steam cracking zone 230. In a py-gas hydrotreating unit, diolefins and olefins in the pyrolysis gasoline are saturated. Hydrotreated pyrolysis gasoline from the py-gas hydrotreating unit is routed to aromatics extraction. In the aromatics extraction step, aromatics are separated from hydrotreated pyrolysis gasoline and fluid catalytic cracking naphtha. For instance, aromatic extraction can separate the hydrotreated pyrolysis gasoline and fluid catalytic cracking naphtha into high-purity benzene, toluene, xylenes and C9 aromatics. C6-C9 aromatics stream 622 can be recovered for chemical markets, C5 raffinate 644 and non-aromatics 646 (for instance, C6-C9) can be recycled to the mixed feed steam cracking zone 230, and heavy aromatic 642 (for instance, C10-C12) products can be used as an aromatic solvent or as an octane boosting additive. In certain embodiments ethylbenzene 628 can be recovered.

Figure 8:
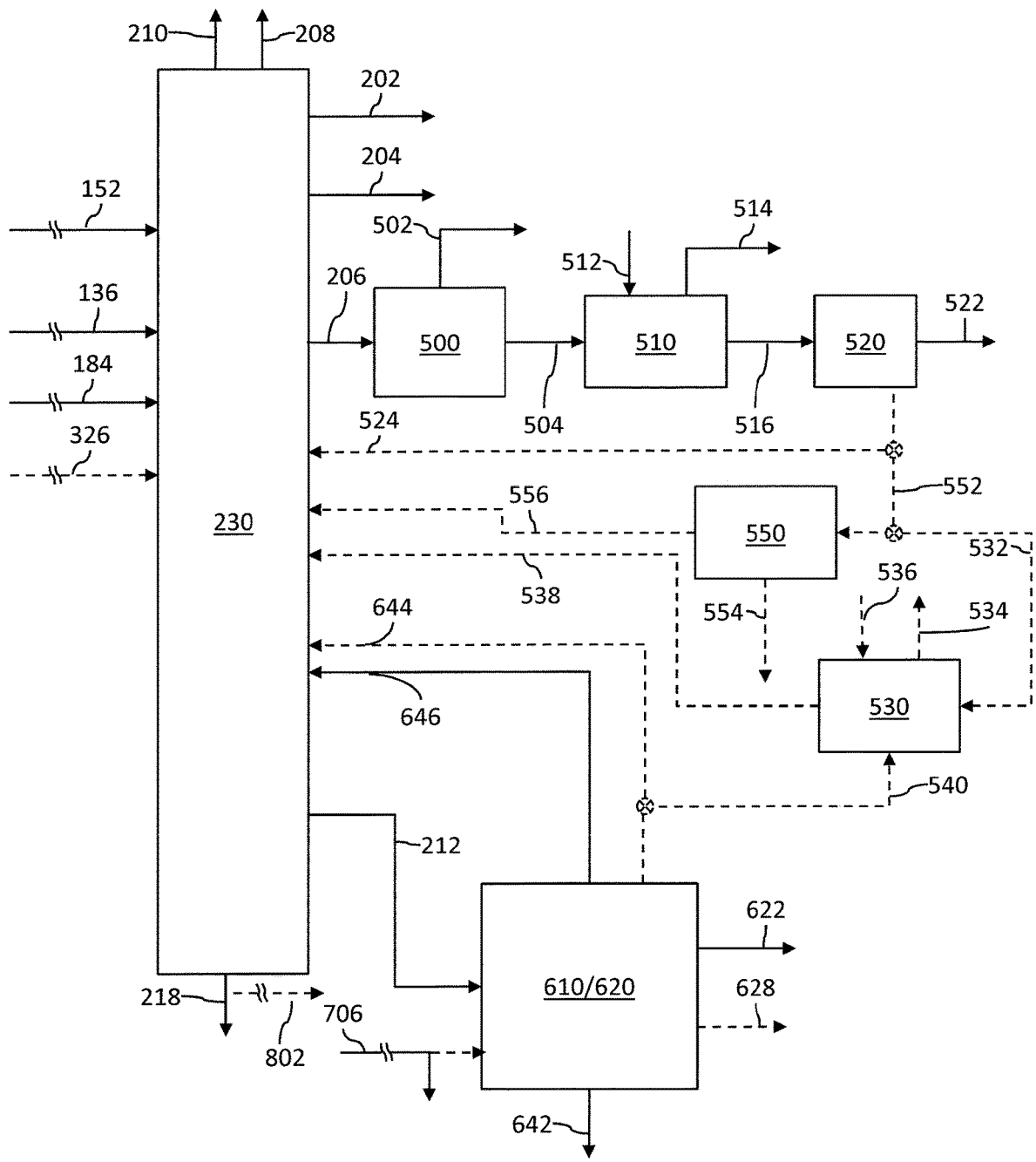
FIG. 8 schematically depicts operations downstream of and including a steam cracker complex in embodiments of processes for producing petrochemicals and fuel products integrating fluid catalytic cracking, steam cracking, metathesis and mixed butanol production.

In the configuration depicted in FIG. 7, an optional diverter is shown, indicated as a diverter and stream in dashed lines, to bypass the process for conversion of a mixture of butenes into mixed butanols, to therefore divert all, a substantial portion, a significant portion or a major portion of the C4 Raff-3 524 to the mixed feed steam cracking zone 230. In alternative modes, flow can be directed to the mixed butanols production zone 550 for conversion of a mixture of butenes into mixed butanols. In further alternative modes, flow of the C4 Raff-3 524 can be directed to the mixed feed steam cracking zone 230 and the mixed butanols production zone 550. In this manner, a producer can vary the quantity of feed to tailor the desired outputs. Accordingly, 0-100% of the third C4 raffinate stream 524 can be routed to mixed butanols production zone 550, and the remainder (if any) is directed to the mixed feed steam cracking zone 230. The quantity can be determined, for instance, based upon demand for ethylene, demand for mixed butanols, and/or minimum ranges for which the unit is operated depending on design capacity FIG. 8 schematically depicts further embodiments of processes and systems for conversion of crude oil to petrochemicals and fuel products. In this embodiment, additional step(s) of metathesis conversion of C4 and C5 olefins to produce additional propylene, and/or conversion of a mixture of butenes into mixed butanols suitable as a gasoline blending oxygenate and for octane enhancement, are integrated. The process operates as described with respect to any of FIG. 1, 2, 4 or 5 upstream of the steam cracking operations and with respect to the fluid catalytic cracking operations.

Downstream of the steam cracking operations, the butadiene extraction train can optionally operate in a manner similar to that in FIG. 3 shown as the stream 524 from a diverter (in dashed lines) from the C4 distillation unit 520 directly to the mixed feed steam cracking zone 230 as an optional mode of operation. The configuration in FIG. 8 integrates selective recovery of various alkene and diene pyrolysis chemicals having four carbons, metathesis conversion to produce additional propylene, and/or conversion of a mixture of butenes into mixed butanols suitable as a gasoline blending oxygenate and for octane enhancement.

FIG. 8 depicts a stream 552 containing butenes from the C4 distillation step ("C4 Raff-3") routed to a crude C4 processing zone such as a butanol production unit 550 for conversion of the mixture of butenes into mixed butanol liquids 554. Alkanes 556 are recycled to the mixed feed steam cracking zone 230. In addition, a portion 532 of the 2-butene rich raffinate-3 from the C4 distillation unit 520 is passed to a metathesis unit 530 for metathesis conversion to additional propylene 534. As indicated, a portion 536 of the ethylene mixed feed steam cracking product can be routed to the metathesis unit 530. In additional embodiments, ethylene for the metathesis unit 530 is supplied from outside the complex limits, instead of or in addition to the portion 536 of the ethylene product 202. A stream 538, having a mixture of mostly saturated C4/C5 from metathesis unit, is recycled to the mixed feed steam cracking zone.

As in FIG. 3, in the configuration of FIG. 8, pyrolysis gasoline 212 from the steam cracking zone 230 is routed to the naphtha hydrotreatment and recovery center 610/620 where select hydrocarbons having 5-12 carbons can be recovered from untreated pyrolysis gasoline and fluid catalytic cracking naphtha, and the remainder is subsequently hydrotreated for aromatics recovery. In a py-gas hydrotreating unit, diolefins and olefins in the pyrolysis gasoline are saturated. Hydrotreated pyrolysis gasoline from the py-gas hydrotreating unit is routed to aromatics extraction. In the aromatics extraction step, aromatics are separated from hydrotreated pyrolysis gasoline and fluid catalytic cracking naphtha. For instance, aromatic extraction can separate the hydrotreated pyrolysis gasoline and fluid catalytic cracking naphtha into high-purity benzene, toluene, xylenes and C9 aromatics. C6-C9 aromatics stream 622, BTX, can be recovered for chemical markets, non-aromatics 646 (for instance, C6-C9) can be recycled to the mixed feed steam cracking zone 230, and heavy aromatics 642 (for instance, C10-C12) products can be used as an aromatic solvent or as an octane boosting additive. In certain embodiments ethylbenzene 628 can be recovered. 540 can be routed to the metathesis unit 530 as shown, and/or optionally recycled to the mixed feed steam cracking as shown in dashed lines, stream 644. In certain embodiments (not shown), all or a portion of the cracked C5s from the py-gas hydrotreater can be routed to the metathesis unit 530 prior to aromatics extraction.

In the configuration depicted in FIG. 8, an optional diverter is shown, indicated as a diverter and stream in dashed lines, to bypass the metathesis conversion process and the process for conversion of a mixture of butenes into mixed butanols, to therefore divert all, a substantial portion, a significant portion or a major portion of the C4 Raff-3 524 to the mixed feed steam cracking zone 230. An optional valve also can be provided to direct flow of the C4 Raff-3 to one or both of the metathesis conversion unit 530 and/or the mixed butanols production zone 550 for conversion of a mixture of butenes into mixed butanols. In further alternative modes, flow of the C4 Raff-3 524 can be directed to each of the mixed feed steam cracking zone 230, the metathesis conversion unit 530 (as stream 532), and the mixed butanols production zone 550 (as stream 552). In this manner, a producer can vary the quantity of feed to tailor the desired outputs. Accordingly, all, a substantial portion, a significant portion or a major portion of the third C4 raffinate stream can be routed to the metathesis conversion unit 530, and the remainder (if any) is directed to the mixed feed steam cracking zone 230 and/or the mixed butanols production zone 550. In certain embodiments, all, a substantial portion, a significant portion or a major portion of the third C4 raffinate stream is routed to the metathesis conversion unit 530, and the remainder (if any) is directed to the mixed feed steam cracking zone 230. In further embodiments, all, a substantial portion, a significant portion or a major portion of the third C4 raffinate stream is routed to the metathesis conversion unit 530, and the remainder (if any) is directed to the mixed butanols production zone 550 for production of mixed butanols. In further embodiments, all, a substantial portion, a significant portion or a major portion of the third C4 raffinate stream is routed to the mixed butanols production zone 550 for production of mixed butanols, and the remainder (if any) is directed to both the mixed feed steam cracking zone 230 and the metathesis conversion unit 530. In further embodiments, all, a substantial portion, a significant portion or a major portion of the third C4 raffinate stream is routed to the mixed butanols production zone 550 for production of mixed butanols, and the remainder (if any) is directed to the mixed feed steam cracking zone 230. In further embodiments, all, a substantial portion, a significant portion or a major portion of the third C4 raffinate stream is routed to the mixed butanols production zone 550 for production of mixed butanols, and the remainder (if any) is directed to the metathesis conversion unit 530. The quantity can be determined, for instance, based upon demand for ethylene, demand for propylene, demand for mixed butanols, and/or minimum ranges for which the unit is operated depending on design capacity.

Figure 9:
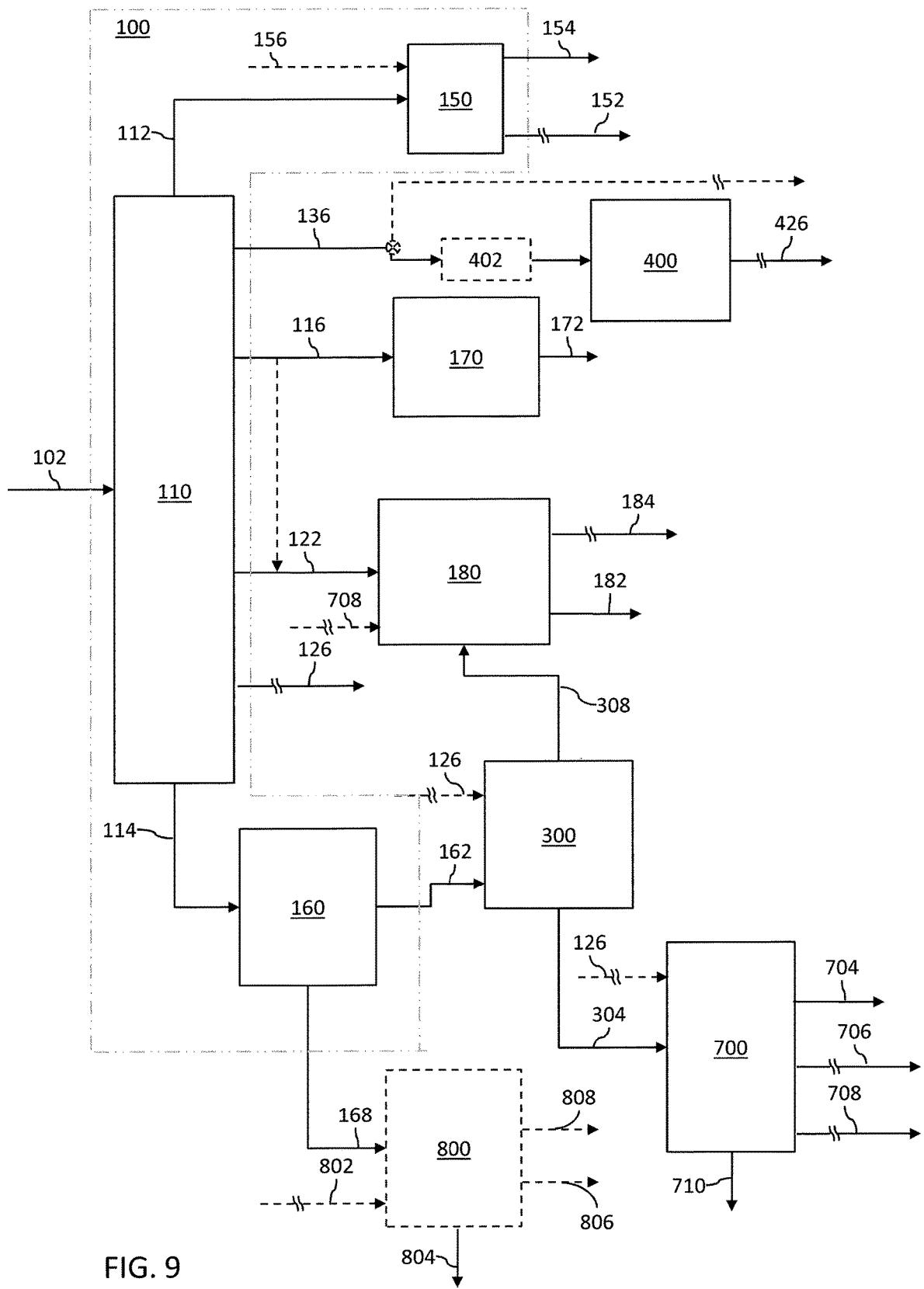
FIGS. 9 and 10 schematically depict operations upstream of a steam cracker complex in further embodiments of processes for producing petrochemicals and fuel products integrating fluid catalytic cracking and steam cracking.
Figure 10:
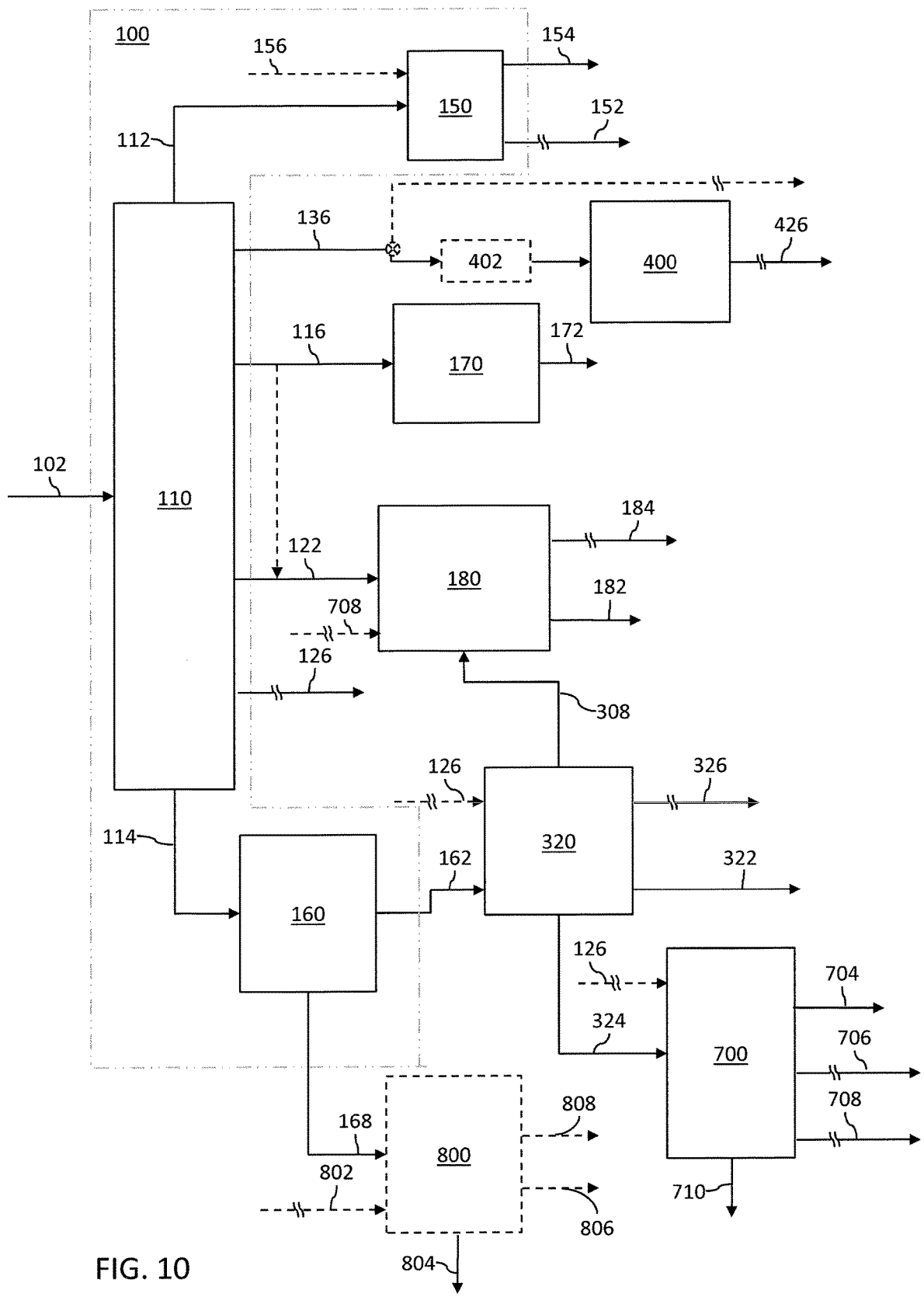
Figure 11:
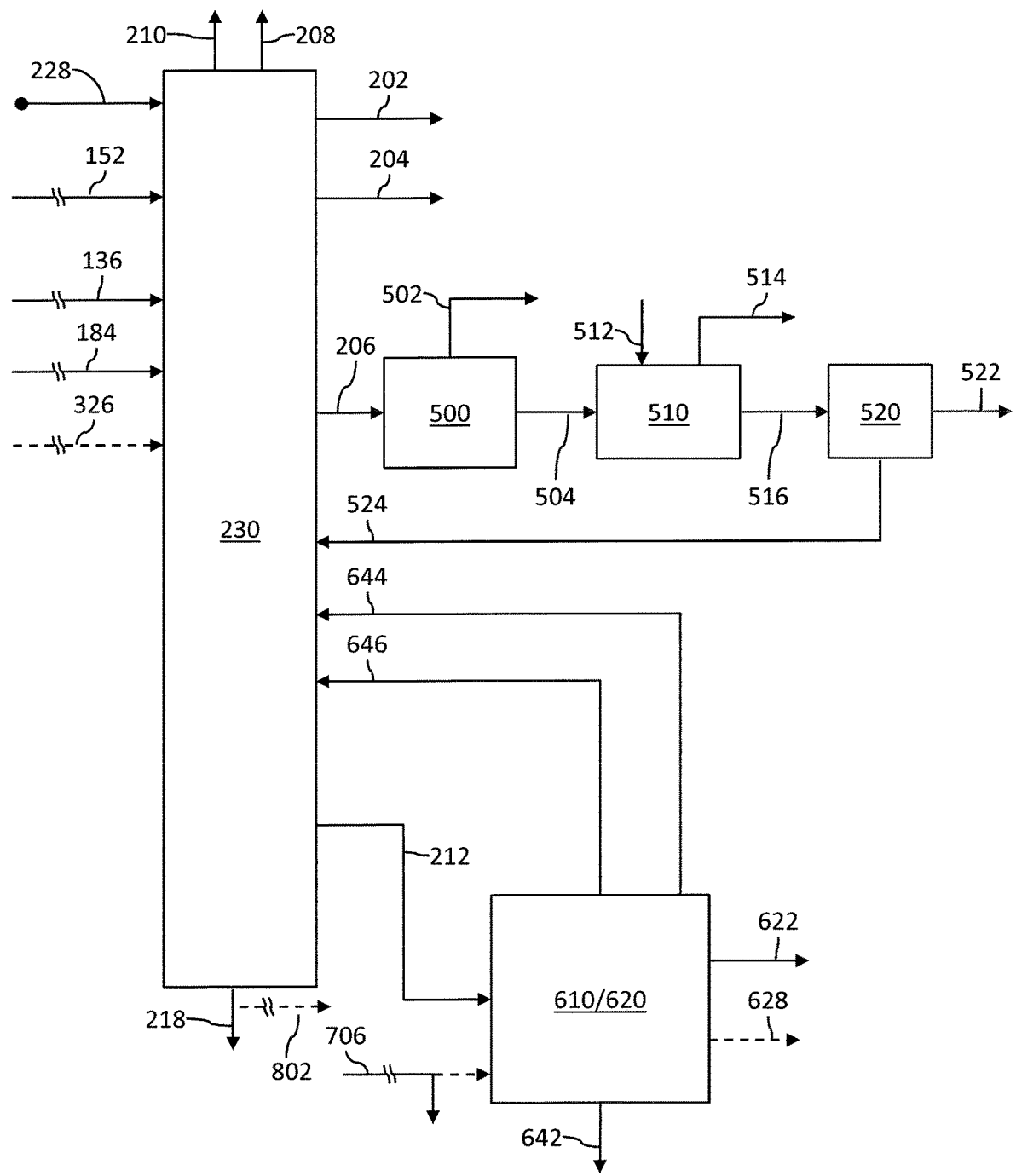
FIG. 11 schematically depicts operations downstream of and including a steam cracker complex in further embodiments of processes for producing petrochemicals and fuel products integrating fluid catalytic cracking and steam cracking.

FIGS. 9 and 11 schematically depict further embodiments of processes and systems for conversion of crude oil to petrochemicals and fuel products. In the arrangement of FIGS. 9 and 11, a crude oil feed 102, in certain embodiments AXL or AL, is fed to an atmospheric distillation zone 110 of a crude complex 100. All or a portion of straight run naphtha 136 is passed to a catalytic reforming zone 400 to produce chemical rich reformate 426. Lighter products 152 are routed to a mixed feed steam cracking zone 230. Middle distillate fractions 116 and 122 are used to produce kerosene and diesel, and wild naphtha 184 as additional feed to the mixed feed steam cracking zone 230. In certain embodiments (as denoted by dashed lines), all or a portion of a third middle distillate fraction 126 is routed to a vacuum gas oil hydroprocessing zone, which can operate as a vacuum gas oil hydrocracker as shown in FIG. 9 or as a vacuum gas oil hydrotreater as shown in FIG. 10. In certain embodiments (as denoted by dashed lines), all or a portion of the third middle distillate fraction 126 is routed to the high olefinic fluid catalytic cracking zone 700, bypassing the vacuum gas oil hydroprocessing zone. In additional embodiments the third middle distillate fraction 126 can be divided between the vacuum gas oil hydroprocessing zone and the high olefinic fluid catalytic cracking zone 700.

The atmospheric residue fraction 114 is further distilled in a vacuum distillation zone 160. VGO 162 from the vacuum distillation zone 160 is routed to a vacuum gas oil hydroprocessing zone, which can operate as a high severity vacuum gas oil hydrotreater or a mild vacuum gas oil hydrocracker. The heaviest fraction 168 from the vacuum distillation zone 160, vacuum residue, can be sent to a fuel oil ("FO") pool or optionally processed in a residue treatment zone 800, shown in dashed lines.

As shown in FIG. 9, a vacuum gas oil hydrotreater 300 can operate under mild, moderate or severe hydrotreating conditions, and generally produces cracked products 308 and hydrotreated gas oil 304. Cracked products 308 from the vacuum gas oil hydrotreater 300 are routed to the diesel hydrotreating zone 180. Hydrotreated gas oil 304 from the vacuum gas oil hydrotreater 300 is routed to a high olefinic fluid catalytic cracking zone 700 configured to produce maximum light olefin product 704. It should be appreciated that the light olefin product 704 can be recovered from the high olefinic fluid catalytic cracking zone 700 as is known, or recovered in combination with the olefins recovery zone 270 and/or the mixed feed steam cracking zone 230 as described herein. The hydrotreated gas oil fraction 304 generally contains the portion of the vacuum gas oil hydrotreater 300 effluent that is at or above the AGO, H-AGO or VGO range.

In certain embodiments, as shown in FIG. 10, a vacuum gas oil hydrocracker 320 can operate under mild, moderate or severe hydrocracking conditions, and generally produces a hydrocracked naphtha product 326, a diesel fuel fraction 322, and an unconverted oil fraction 324. Hydrocracked naphtha 326 from the vacuum gas oil hydrocracker 320 is routed to the mixed feed steam cracking zone 230. The unconverted oil fraction 324 is routed to the high olefinic fluid catalytic cracking zone 700. The diesel fuel fraction 322 is recovered as fuel, for instance, compliant with Euro V diesel standards, and can be combined with the diesel fuel fraction 182 from the diesel hydrotreating zone 180.

Further, an aromatics recovery center 620 is included, in which aromatics are separated from pyrolysis gasoline 212 and hydrotreated pyrolysis gasoline can be obtained. C6-C9 aromatics 622 are recovered for chemical markets, C6-C9 non-aromatics 646 are recycled to the mixed feed steam cracking zone 230, and C10-C12 products 642 can be used as an aromatic solvent or used as gasoline blenders as an octane boosting additive.

In certain embodiments, as shown in dashed lines, high olefinic fluid catalytic cracking naphtha 706 is hydrotreated and fed to the aromatics extraction, the light naphtha and middle naphtha are fed to the mixed feed steam cracking zone 230. The C5 and C9 streams from the high olefinic fluid catalytic cracker can be recycled to the mixed feed steam cracking zone 230.

In a further embodiment, all or a portion of the high olefinic fluid catalytic cracking naphtha 706 is used as a gasoline blendstock, rather being used in its entirety as feed to the mixed feed steam cracking zone; any remainder of the of the high olefinic fluid catalytic cracking naphtha 706 can be used as feed to the mixed feed steam cracking zone 230.

In additional embodiments, all or a portion of pyrolysis oil 218 from the steam cracking zone 230 can be passed to a catalytic hydrogen addition process, such as a residue hydrocracking or conditioning process In additional embodiments, pyrolysis oil 218 is split into light and heavy fractions, whereby the light fraction is fed to the gas oil hydroprocessing zone and the heavy fraction is fed to the catalytic hydrogen addition process, such as a residue hydrocracking or conditioning process.

In still further embodiments, all or a portion of the hydrotreated gas oil fraction or unconverted oil fraction from the gas oil hydroprocessing zone is passed to an isodewaxing unit and a hydrofinishing unit, for instance, to enable production of group III lube oils or lube oil feedstocks.

Figure 12:
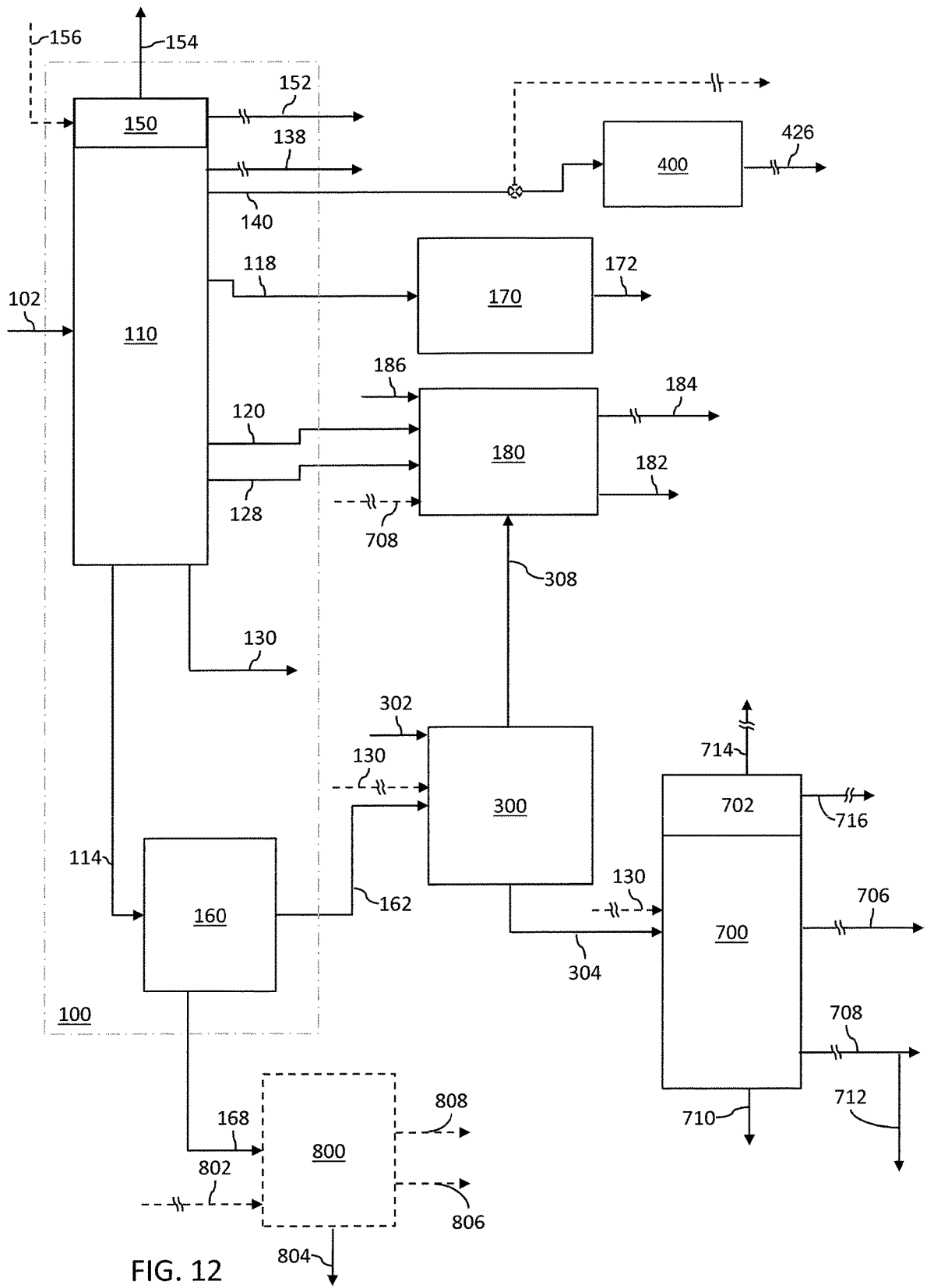
FIGS. 12 and 13 schematically depict operations upstream of a steam cracker complex in additional embodiments of processes for producing petrochemicals and fuel products integrating fluid catalytic cracking and steam cracking.
Figure 13:
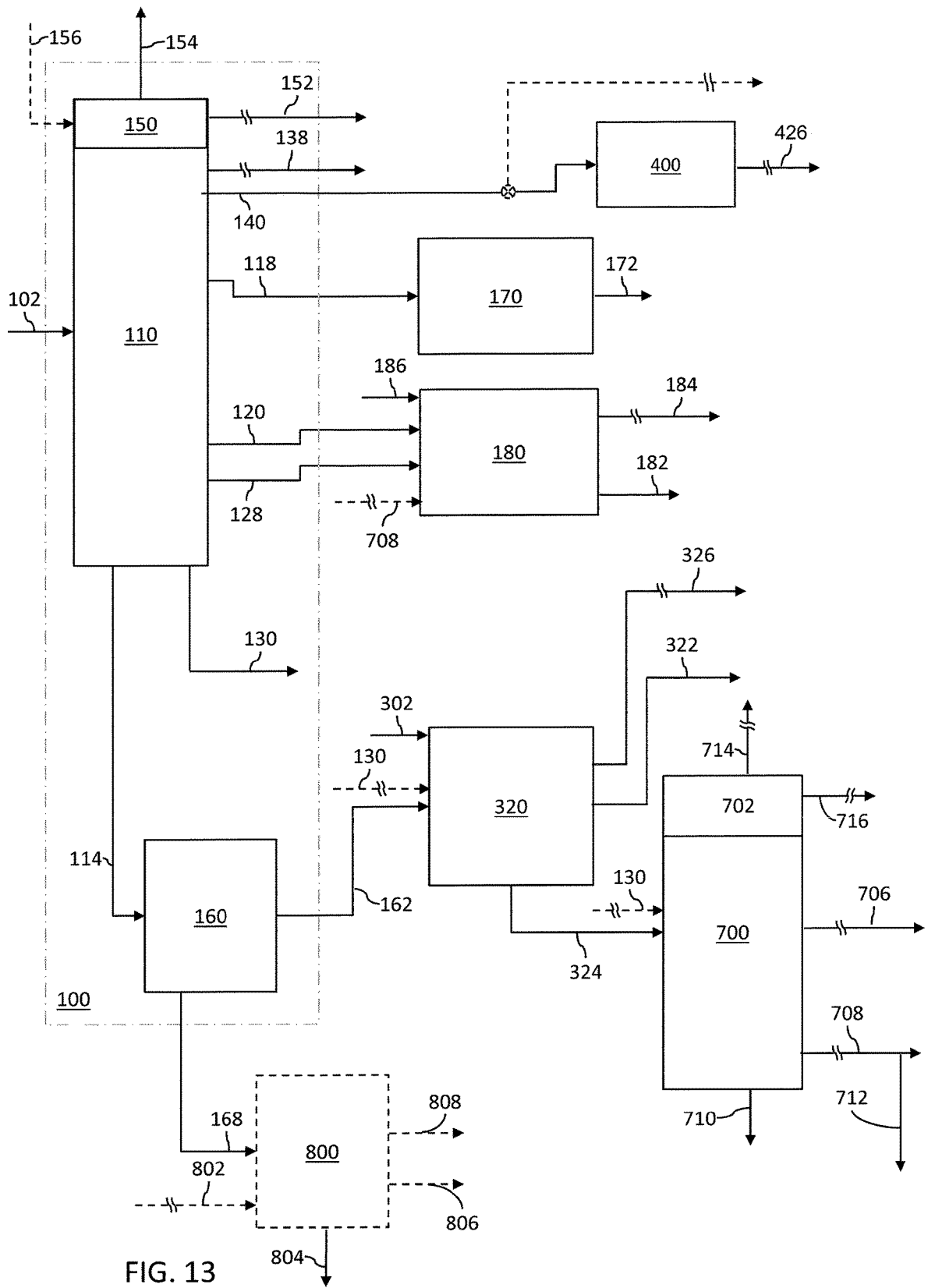
Figure 21:
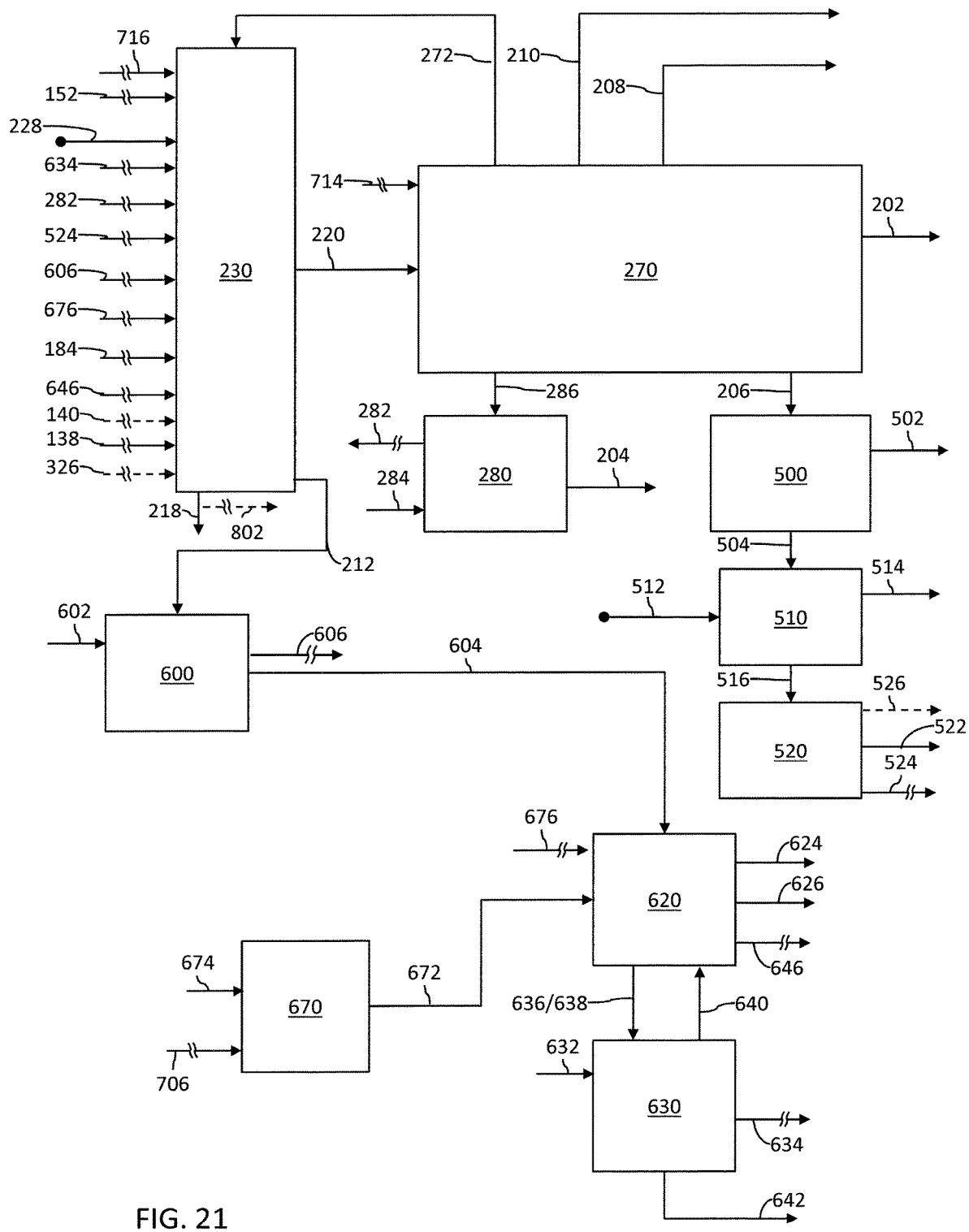
FIG. 21 schematically depicts operations downstream of and including a steam cracker complex in additional embodiments of processes for producing petrochemicals and fuel products integrating fluid catalytic cracking and steam cracking.

FIGS. 12, 13 and 21 schematically depict embodiments of processes and systems for conversion of crude oil to petrochemicals and fuel products including a mixed feed steam cracking zone and a high olefinic fluid catalytic cracking zone 700. Generally, FIGS. 12 and 13 show operations upstream of the mixed feed steam cracking zone 230 while FIG. 21 shows operations downstream of and including the mixed feed steam cracking zone 230.

A crude oil feed 102 is passed to a crude complex 100. In the embodiment of FIGS. 12, 13 and 21, the crude complex 100 generally includes an atmospheric distillation zone 110, a saturated gas plant 150 and a vacuum distillation zone 160. The atmospheric distillation unit is used in well-known arrangements.

Intermediate streams obtained from the feed 102 via separation in the crude complex 100 include: off-gas 154, obtained within the crude complex 100 via the saturated gas plant 150, and which is passed to a fuel gas system; a light ends stream 152, obtained within the crude complex 100 via the saturated gas plant 150, and which is passed to the mixed feed steam cracking zone 230; one or more straight run naphtha stream(s), in this embodiment a light naphtha stream 138 and a heavy naphtha stream 140, with all or a portion of the light naphtha stream 138 being passed to the mixed feed steam cracking zone 230, and all or a portion of the heavy naphtha stream 140 passed to a catalytic reforming zone 400 to produce chemical rich reformate 426; a first middle distillate stream 118, such as a light kerosene stream, that is passed to a kerosene sweetening zone 170, such as a mercaptan oxidation zone; a second middle distillate stream 120, such as a heavy kerosene stream, that is passed to a diesel hydrotreating zone 180; a third middle distillate stream 128, such as a medium atmospheric gas oil stream, that is passed to the diesel hydrotreating zone 180; a fourth middle distillate stream 130, such as a heavy atmospheric gas oil stream, that is passed to a high olefinic fluid catalytic cracking zone 700 (directly, or optionally through the vacuum gas oil hydrotreating zone 300, as indicated by dashed lines); an atmospheric residue fraction 114 that is passed to the vacuum distillation zone 160 of the crude complex 100; a vacuum gas oil stream 162 from the vacuum distillation zone 160 that is passed to the vacuum gas oil hydroprocessing zone; and a vacuum residue 168 from the vacuum distillation zone 160, all or a portion of which can optionally be passed to a residue treating zone 800, and/or to a fuel oil pool.

The intermediate streams from the crude complex 100 are used in an efficient manner in the integrated process and system herein. The light ends stream 152, and a portion of the straight run naphtha stream(s), in this embodiment light naphtha 138, are routed to the mixed feed steam cracking zone 230 as feed for conversion into light olefins and other valuable petrochemicals. In certain embodiments, all, a substantial portion or a significant portion of the light naphtha 138 is routed to the mixed feed steam cracking zone 230, and the remainder (if any) passed to a catalytic reforming zone 400. All or a portion of the heavy naphtha 140 from the atmospheric distillation zone 110 is passed to the catalytic reforming zone 400 to produce chemical rich reformate 426, which can be routed as additional feed to the aromatics extraction zone 620 or used for gasoline blending. In certain embodiments, all, a substantial portion or a significant portion of the heavy naphtha 140 is routed to the catalytic reforming zone 400, and the remainder (if any) passed to the mixed feed steam cracking zone 230. Either or both of the straight run naphtha streams, light naphtha 138 and heavy naphtha 140, can optionally be steam-stripped in a side stripper prior to routing to the mixed feed steam cracking zone 230.

Components of the crude complex not shown but which are well-known can include feed/product and pump-around heat exchangers, crude charge heaters, crude tower(s), product strippers, cooling systems, hot and cold overhead drum systems including re-contactors and off-gas compressors, and units for water washing of overhead condensing systems. The atmospheric distillation zone 110 can include well-known design features. Furthermore, in certain embodiments, naphtha, kerosene and atmospheric gas oil products from the atmospheric distillation column are steam-stripped in side strippers, and atmospheric residue is steam-stripped in a reduced-size can section inside the bottom of the atmospheric distillation column.

The feed to the atmospheric distillation zone 110 is primarily the crude feed 102, although it shall be appreciated that wild naphtha, LPGs and off-gas streams from the diesel hydrotreating zone 180; and in certain embodiments from the vacuum gas oil hydroprocessing step and/or an optional residue treating zone, can be routed to the atmospheric distillation zone 110 where they are fractionated before being passed to the cracking complex. A desalting unit (not shown) is typically included upstream of the distillation zone 110. A substantial amount of the water required for desalting can be obtained from a sour water stripper within the integrated process and system.

The desalting unit refers to a well-known arrangement of vessels for desalting of crude oil, and as used herein is operated to reduce the salt content to a target level, for instance, to a level of less than or equal to about 10, 5, or 3 wppm. In certain embodiments two or more desalters are included to achieve a target salt content of less than or equal to about 3 wppm.

In one embodiment of a crude complex 100 herein, feed 102 is preheated before entering a desalting unit, for instance, to a temperature (° C.) in the range of about 105-165, 105-150, 105-145, 120-165, 120-150, 120-145, 125-165, 125-150, 125-145, and in certain embodiments about 135. Suitable desalters are designed to remove salt down to a typical level of about 0.00285 kg/m$^3$ (1 lb/1000 bbl) in a single stage. In certain embodiments, plural preheat and desalting trains are employed. The desalter operating pressure can be based on a pressure margin above crude and water mixture vapor pressure at desalter operating temperature to ensure liquid phase operation, for instance in the range of about 2.75-4.15, 2.75-3.80, 2.75-3.65, 3.10-4.15, 3.10-3.80, 3.10-3.65, 3.25-4.15, 3.25-3.80, 3.25-3.65 and in certain embodiments about 3.45 barg.

The atmospheric distillation zone 110 can employ fractionated products and pumparounds to provide enough heat for desalting. In certain embodiments, the desalter operating temperature can be controlled by a diesel pumparound swing heat exchanger. In certain embodiments, desalter brine preheats desalter make-up water in a spiral type heat exchanger to minimize fouling and achieve rundown cooling against cooling water before the brine is routed to the wastewater system.

In certain embodiments, desalted crude is preheated before entering a preflash tower, to a temperature (° C.) in the range of about 180-201, 185-196, or 189-192. The preflash tower removes LPG and light naphtha from the crude before it enters the final preheat exchangers. The preflash tower minimizes the operating pressure of the preheat train to maintain liquid phase operation at the crude furnace pass valves and also reduces the requisite size of the main crude column.

In one example of a suitable crude distillation system, a crude furnace vaporizes materials at or below a certain cut point, for instance, at a temperature (° C.) in the range of about 350-370, 355-365 or 360 (680° F.), before the crude enters the flash zone of the crude tower. The furnace is designed for a suitable outlet temperature, for instance, at a temperature (° C.) in the range of about 338-362, 344-354 or 348.9 (660° F.). Crude column flash zone conditions are at a temperature (° C.) in the range about 328-374, 328-355, 337-374, 327-355, or 346.1 (655° F.), and a pressure (barg) in the range of about 1.35-1.70, 1.35-1.60, 1.44-1.70, 1.44-1.60 or 1.52.

In certain embodiments the crude tower contains 59 trays and produces six cuts, with draw temperatures for each product as follows: light naphtha, 104.4° C. (220° F.) (overhead vapor); heavy naphtha, 160.6° C. (321° F.) (sidedraw); kerosene, 205° C. (401° F.) (sidedraw); diesel, 261.7° C. (503° F.) (sidedraw); AGO, 322.2° C. (612° F.) (sidedraw); atmospheric residue, 340.6° C. (645° F.) (bottoms). The heavy naphtha draw includes a reboiled side stripper against diesel pumparound, and is controlled to a 185° C. (365° F.) D86 end point. The kerosene draw includes a steam stripper at 14.54 kg/m$^3$ (5.1 lb steam per bbl); the draw rate is limited on the back end by freeze point. The diesel draw includes a steam stripper at 14.54 kg/m$^3$ (5.1 lb steam per bbl), and this draw is controlled to a 360° C. (680° F.) D86 95% point. The AGO draw includes a steam stripper at 14.82 kg/m$^3$ (5.2 lb steam per bbl), which sets the overflash at 2 vol % on crude. The crude tower also contains 3 pumparounds for top, diesel, and AGO. Diesel pumparound provides heat to the heavy naphtha stripper reboiler and debutanizer reboiler along with controlling desalter operating temperature via swing heat. The bottoms stream of the atmospheric column is steam stripped at 28.5 kg/m$^3$ (10 lb steam/bbl).

The atmospheric residue stream 114 from the atmospheric distillation zone 110 is further distilled in the vacuum distillation zone 160, which fractionates the atmospheric residue fraction 114 into light and heavy vacuum gas oil streams 162 which are fed to the VGO hydroprocessing zone, as well as a vacuum residue stream 168, 0-100 wt % of which can be optionally routed to a residue treating zone 800; any portion not subjected to processing in the residue treating zone 800 can be routed, for instance, to a fuel oil pool (such as a high sulfur fuel oil pool). The vacuum distillation zone 160 can include well-known design features, such as operation at reduced pressure levels (mm Hg absolute pressure), for instance, in the range of about 30-40, 32-36 or 34, which can be maintained by steam ejectors or mechanical vacuum pumps. Vacuum bottoms can be quenched to minimize coking, for instance, via exchange against crude at a temperature (° C.) in the range of about 334-352, 334-371, 338-352, 338-371 or 343.3 (650° F.). Vacuum distillation can be accomplished in a single stage or in plural stages. In certain embodiments, the atmospheric residue fraction 114 is heated in a direct fired furnace and charged to vacuum fractionator at a temperature (° C.) in the range of about 390-436, 390-446, 380-436, 380-446 or 400-425.

In one embodiment, the atmospheric residue is heated to a temperature (° C.) in the range of about 399-420, 399-430, 389-420, 389-430 or 409.4 (769° F.) in the vacuum furnace to achieve flash zone conditions of a temperature (° C.) in the range of about 392-412, 392-422, 382-412, 382-422 or 401.7 (755° F.) and pressure levels (mm Hg absolute pressure) in the range of about 30-40, 32-36 or 34. The vacuum column is designed for a theoretical cut point temperature (° C.) in the range of about 524-551, 524-565, 511-551, 511-565 or 537.8 (1000° F.), by removing light VGO and heavy VGO from the vacuum residue. The overhead vacuum system can include two parallel trains of jet ejectors each including three jets. A common vacuum pump is used at the final stage. In one embodiment, the vacuum tower is sized for a 0.35 C-Factor and about a 14.68 lpm/m² (0.3 gpm/ft²) wetting rate at the bottom of the wash zone. Wash zone slop wax is recycled to the vacuum furnace to minimize fuel oil production. Vacuum bottoms are quenched via exchange against crude to minimize coking at a temperature (° C.) in the range of about 334-352, 334-371, 338-352, 338-371 or 343.3° C. (650° F.).

The saturated gas plant 150 generally comprises a series of operations including fractionation and in certain systems absorption and fractionation, as is well known, with an objective to process light ends to separate fuel gas range components from LPG range components suitable as a steam cracker cracking zone feedstock. The saturated gas plant 150 includes off-gas compression and recontacting to maximize LPG recovery, LPG fractionation from light naphtha, and off-gas/LPG amine treatment. The light ends that are processed in one or more saturated gas plants within embodiments of the integrated system and process herein are derived from the crude distillation, such as light ends and LPG. In addition, other light products can optionally be routed to the saturated gas plant 150, shown in dashed lines as stream 156, such as light gases from refinery units within the integrated system, and in certain embodiments light gases from outside of the battery limits. For instance, stream 156 can contain off-gases and light ends from the diesel hydrotreating zone 180, the gas oil hydroprocessing zone, the py-gas hydrotreating zone 600 and/or the residue treating zone 800. The products from the saturated gas plant 150 include: an off-gas stream 154, containing C1-C2 alkanes, that is passed to the fuel gas system and/or the steam cracker complex; and a light ends stream 152, containing C2+, that is passed to the mixed feed steam cracking unit 230.

In certain embodiments, a suitable saturated gas plant 150 includes amine and caustic washing of liquid feed, and amine treatment of vapor feed, before subsequent steps. The crude tower overhead vapor is compressed and recontacted with naphtha before entering an amine scrubber for $H_2S$ removal and is then routed to the steam cracker complex. Recontact naphtha is debutanized to remove LPGs which are amine washed and routed to the steam cracker complex. The debutanized naphtha is routed separately from the heavy naphtha to the steam cracker complex. As is known, light naphtha absorbs C4 and heavier hydrocarbons from the vapor as it travels upward through an absorber/debutanizer. Off-gas from the absorber/debutanizer is compressed and sent to a refinery fuel gas system. A debutanizer bottoms stream is sent to the mixed feed steam cracker as an additional source of feed.

All, a substantial portion or a significant portion of the heavy naphtha 140 from the atmospheric distillation zone 110 (and in certain embodiments all or a portion of the heavy naphtha 138, not shown) is passed to a catalytic reforming zone 400 to produce chemical rich reformate 426, which can be routed as additional feed to the aromatics extraction zone 620 and/used for gasoline blending. The catalytic reforming zone 400 generally includes a naphtha hydrotreating zone and a catalytic reforming zone. In certain embodiments the catalytic reforming zone also includes a reformate splitter and/or a benzene saturation unit. Product from the naphtha hydrotreating zone includes LPG and gases, and hydrotreated naphtha product that is routed to a naphtha reformer. The naphtha reformer converts hydrotreated naphtha to chemical rich reformate, which is a significant source of aromatic bulk chemicals from the aromatics extraction zone downstream of the steam cracking operations. In certain embodiments, all or a portion of the chemical rich reformate can be used in a conventional manner, that is, as gasoline blending components; any remainder can be used as feed to the mixed feed steam cracker.

The reactions involved in catalytic reforming include hydrocracking, dehydrocyclization, dehydrogenation, isomerization, and to a lesser extent, demethylation and dealkylation. A particular hydrocarbon/naphtha feed molecule may undergo more than one category of reaction and/or may form more than one product. The hydrocarbon/naphtha feed composition, the impurities present therein, and the desired products will determine such process parameters as choice of catalyst(s), process type, and the like.

The reaction rate for conversion of naphthenes to aromatics favors low pressure, but so does coke formation which deactivates the catalyst. Thus with lower operating pressure the aromatics yield increases, but catalyst regeneration must be done more frequently. To maintain the desired lower operating pressure and also address coke formation, different methodologies are known. The general types of catalytic reforming process configurations differ in the manner in which the reforming catalyst is regenerated for removal of coke formed during reaction. Catalyst regeneration, which involves combusting the detrimental coke in the presence of oxygen, includes a semi-regenerative process, cyclic regeneration and continuous catalyst regeneration (CCR). Semi-regeneration is the simplest configuration, and the entire unit, including all reactors in the series is shutdown for catalyst regeneration in all reactors. Cyclic configurations utilize an additional "swing" reactor to permit one reactor at a time to be taken off-line for regeneration while the others remain in service. Continuous catalyst regeneration configurations, which are the most complex, provide for essentially uninterrupted operation by catalyst removal, regeneration and replacement. While continuous catalyst regeneration configurations include the ability to increase the severity of the operating conditions due to higher catalyst activity, the associated capital investment is necessarily higher.

In certain embodiments, the straight run naphtha, or the heavy naphtha, is separated into a normal paraffin (n-paraffin) rich stream and a non-normal rich stream containing branched paraffins. This is accomplished using a separation zone 402 (shown in dashed lines as optional), which can be, for instance, based on technology commercially available from Honeywell UOP, US (MaxEne™). The n-paraffin rich stream bypasses the catalytic reforming zone and is routed to the mixed feed steam cracking zone 230, enabling an increase in the combined yield of ethylene and propylene. Processing of the n-paraffin rich stream in the mixed feed steam cracking zone 230 can also reduce coking which can facilitate increases in throughput or extended run times between de-coking cycles. The stream rich in non-normal paraffins also has significant benefits when processed in the catalytic reformer, including improved selectivity and reduced coke formation on the catalyst, which can facilitate increases in throughput.

Figure 14:
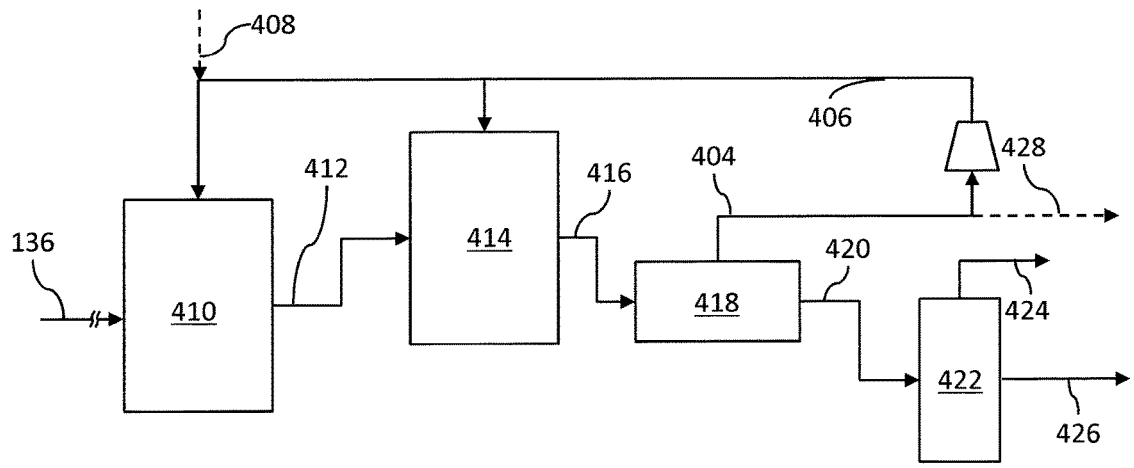
FIGS. 14, 15 and 16 schematically depict operation of a catalytic reforming zone for production of chemical rich reformate.
Figure 15:
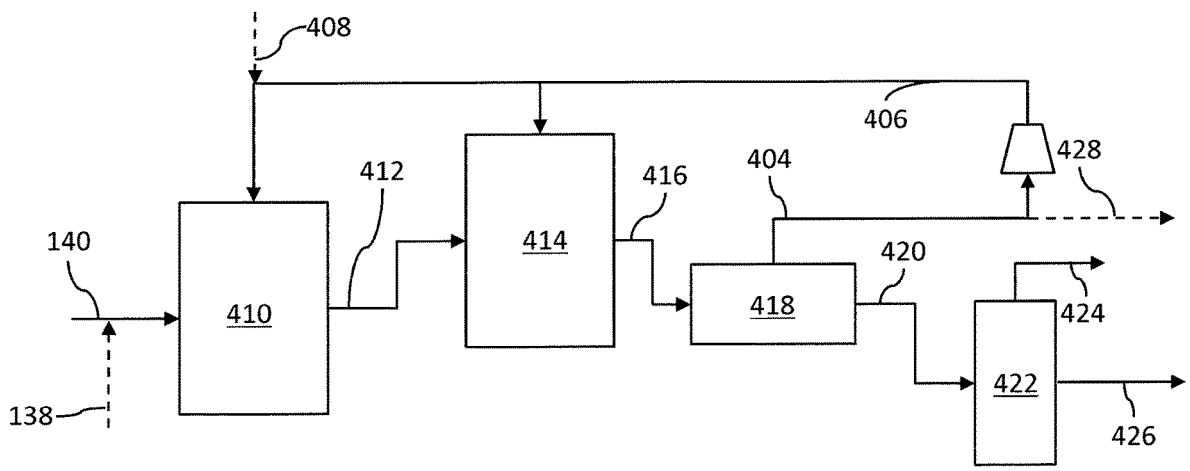
Figure 16:
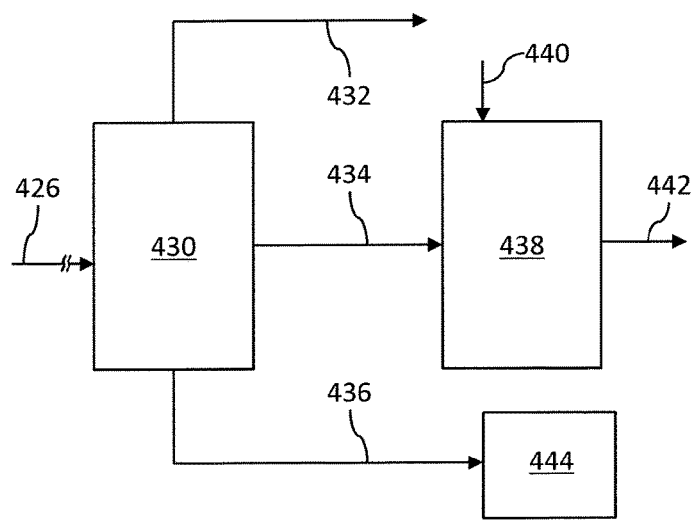

A schematic process flow diagram of a catalytic reforming zone 400 is shown in FIGS. 14 and 15, and in certain embodiments combined with the units of FIG. 16. A naphtha hydrotreating zone 410 is integrated with a catalytic reforming reaction zone 414 for the processing of a straight run naphtha stream 136 (FIG. 14) or a heavy naphtha stream 140 (FIG. 15), to produce chemical rich reformate 426 for chemical recovery, as a gasoline blend component, or both for chemical recovery and as a gasoline blend component. In certain embodiments, all, a substantial portion, a significant portion or a major portion of the chemical rich reformate 426 is passed to the aromatics extraction zone 620, and any remainder can be blended in a gasoline pool.

The naphtha feed 136 or 140 (or in certain embodiments the stream rich in non-normal paraffins from an optional separation zone 402) is hydrotreated in the naphtha hydrotreating zone 410 to produce a hydrotreated naphtha stream 412. In embodiments of FIG. 15 in which the feed to the naphtha hydrotreating zone 410 is heavy naphtha stream 140, light naphtha 138 can be routed to the mixed feed steam cracking unit 230. In further embodiments, the feed to the naphtha hydrotreating zone 410 can also be a full range naphtha including light naphtha (for instance, both the heavy naphtha stream 140 combined with which can be the light naphtha stream 138 described in other embodiments). Accordingly, depending on demand and/or the desired product slate, light naphtha 138 can be routed to the mixed feed steam cracking unit 230 to increase production of olefinic petrochemicals, or alternatively included with the feed to the catalytic reforming zone to increase production of aromatic petrochemicals and/or fuel blending components. In certain embodiments, all, a substantial portion or a significant portion of light naphtha 138 is routed to the mixed feed steam cracking unit 230 (with any remainder optionally passed to the catalytic reforming zone 400); and all, a substantial portion or a significant portion of heavy naphtha 140 is routed to the catalytic reforming zone 400 (with any remainder optionally passed to the mixed feed steam cracking unit 230).

Hydrotreating occurs in the presence of an effective amount of hydrogen obtained from recycle within the naphtha hydrotreating zone 410 (not shown), recycle reformer hydrogen 406, and if necessary make-up hydrogen 408 (shown in dashed lines). Effluent off-gases are recovered from the naphtha hydrotreating zone 410 and are passed the olefins recovery train, the saturated gas plant as part of the other gases stream 156, and/or directly to a fuel gas system. Liquefied petroleum gas is recovered from the naphtha hydrotreating zone 410 and is routed to the mixed feed steam cracking zone, the olefins recovery train and/or the saturated gas plant.

In certain embodiments, all or a portion of any necessary make-up hydrogen 408 is derived from the steam cracker hydrogen stream 210 from the olefins recovery train 270. In additional embodiments hydrogen gas recovered from the catalytic reforming reaction zone 414 provides sufficient hydrogen to maintain the hydrogen requirements of naphtha hydrotreating zone 410 when the reactions reach equilibrium. In further embodiments, there is a net hydrogen gain in the catalytic reforming zone so that hydrogen can be added, for instance, to the other hydrogen users in the integrated process, and/or to the fuel gas that is used to operate the various heating units within the integrated process. A suitable naphtha hydrotreating zone 410 can include, but is not limited to, systems based on technology commercially available from Honeywell UOP, US; Chevron Lummus Global LLC (CLG), US; Axens, IFP Group Technologies, FR; Shell Global Solutions, US, Haldor Topsoe A/S, DK; GTC Technology US, LLC, US; or Exxon Mobil Corporation, US.

The naphtha hydrotreating zone 410 is operated under conditions, and utilizes catalyst(s), effective for removal of a significant amount of the sulfur and other known contaminants. Accordingly, the naphtha hydrotreating zone 410 subjects feed to hydrotreating conditions to produce a hydrotreated straight run naphtha stream 412 effective as feed to the catalytic reforming reaction zone 414. The naphtha hydrotreating zone 410 operates under conditions of, e.g., temperature, pressure, hydrogen partial pressure, liquid hourly space velocity (LHSV), catalyst selection/loading that are effective to remove at least enough sulfur, nitrogen, olefins and other contaminants needed to meet requisite product specifications. For instance, hydrotreating in conventional naphtha reforming systems generally occurs under relatively mild conditions that are effective to remove sulfur and nitrogen to less than 0.5 ppmw levels.

In certain embodiments, the naphtha hydrotreating zone 410 operating conditions include:

a reactor inlet temperature (° C.) in the range of from about 355-400, 355-375, 355-385, 370-400 or 360-390;

a reactor outlet temperature (° C.) in the range of from about 400-450, 400-430, 410-450, 420-450 or 410-430;

a start of run (SOR) reaction temperature (° C.), as a weighted average bed temperature (WABT), in the range of from about 330-375, 330-360, 340-375, 355-375 or 330-350;

an end of run (EOR) reaction temperature (° C.), as a WABT, in the range of from about 390-435, 390-420, 390-410, 400-410 or 400-435;

a reaction inlet pressure (barg) in the range of from about 48-60, 48-52, 48-55, 50-55 or 50-60;

a reaction outlet pressure (barg) in the range of from about 40-51, 40-44, 40-48, 45-51 or 45-48;

a hydrogen partial pressure (barg) (outlet) in the range of from about 24-34, 24-30, 27-34 27-30 or 27-32;

a hydrogen treat gas feed rate (SLt/Lt) up to about 645, 620, 570, 500 or 530, in certain embodiments from about 413-640, 413-570, 413-542, 465-620, 465-570, 465-542, 491-620, 491-570 or 491-542;

a quench gas feed (SLt/Lt) up to about 99, 90, 85, 78 or 70, in certain embodiments from about 57-90, 57-78, 57-75, 64-85, 64-78, 64-75, 68-85, 68-78 or 68-75; and;

a make-up hydrogen feed rate (SLt/Lt) up to about 125, 110 or 102, in certain embodiments from about 78-120, 78-110, 78-102, 87-120, 87-110, 87-102, 92-120, 92-110, 92-102 or 95-100.

Effective straight run naphtha reactor catalyst include those possessing hydrotreating functionality and which generally contain one or more active metal component of metals or metal compounds (oxides or sulfides) selected from the Periodic Table of the Elements IUPAC Groups 6-10. In certain embodiments, the active metal component is one or more of cobalt, nickel, tungsten and molybdenum. The active metal component is typically deposited or otherwise incorporated on a support, such as amorphous alumina, amorphous silica alumina, zeolites, or combinations thereof. The catalyst used in the hydrotreating zone 410 can include one or more catalyst selected from cobalt/molybdenum, nickel/molybdenum, nickel/tungsten, and cobalt/nickel/molybdenum. Combinations of one or more of cobalt/molybdenum, nickel/molybdenum, nickel/tungsten and cobalt/nickel/molybdenum, can also be used. The combinations can be composed of different particles containing a single active metal species, or particles containing multiple active species. In certain embodiments, cobalt/molybdenum hydrodesulfurization catalyst is suitable. Effective liquid hourly space velocity values ($h^{-1}$), on a fresh feed basis relative to the hydrotreating catalysts, are in the range of from about 0.1-10.0, 0.1-5.0, 0.1-2.0, 0.3-10.0, 0.3-5.0, 0.3-2.0, 0.5-10.0, 0.5-5.0, 0.5-2.0 or 0.8-1.2. Suitable hydrotreating catalysts used in the hydrotreating zone 410 have an expected lifetime in the range of about 28-44, 34-44, 28-38 or 34-38 months.

The hydrotreated naphtha stream is treated in the catalytic reforming zone to produce a reformate. A suitable catalytic reforming zone can include, but is not limited to, systems based on technology commercially available from Honeywell UOP, US; Chevron Lummus Global LLC (CLG), US; Axens, IFP Group Technologies, FR; Haldor Topsoe A/S, DK; or Exxon Mobil Corporation, US.

The hydrotreated naphtha stream 412 is passed to a catalytic reforming reaction zone 414. In certain embodiments, all, a substantial portion or a significant portion of the hydrotreated naphtha stream 412 is passed to a catalytic reforming reaction zone 414, and any remainder can be blended in a gasoline pool. The reactor effluent 416, containing hot reformate and hydrogen, is cooled and passed to separator 418 for recovery of hydrogen stream 404 and a separator bottoms stream 420. The hydrogen stream 404 is split into a portion 406 which is compressed and recycled back to the reformer reactors, and in certain embodiments an excess hydrogen stream 428. The separator bottoms stream 420 is passed to a stabilizer column 422 to produce a light end stream 424 and a reformate stream 426. The light end stream 424 is recovered and can be routed to the mixed feed steam cracking zone, the olefins recovery train and/or the saturated gas plant.

The net hydrogen stream 428 can be recovered from the catalytic reforming reaction zone 414 (shown in dashed lines as optional), which comprises excess hydrogen passed to other hydrogen users including: those within the catalytic reforming zone 400 such as the naphtha hydrotreating zone 410 and in certain embodiments a benzene saturation unit 438 shown in FIG. 16; and/or those elsewhere in the integrated process, such as the hydroprocessing unit(s) for middle distillates, pyrolysis gasoline, vacuum gas oil and/or transalkylation A suitable benzene saturation system can include, but is not limited to, systems based on technology commercially available from Honeywell UOP, US; Axens, IFP Group Technologies, FR; or GTC Technology US, LLC, US.

In general, the operating conditions for the reactor(s) in the catalytic reforming reaction zone 414 include:

a reactor inlet temperature (° C.) in the range of from about 450-580, 450-530, 450-500, 490-530 or 490-570;

a reactor outlet temperature (° C.) in the range of from about 415-540, 415-490, 415-500, 440-500 or 450-530;

a start of run (SOR) reaction temperature (° C.), as a weighted average bed temperature (WABT), in the range of from about 445-520, 445-480, 445-500, 470-500 or 470-520;

an end of run (EOR) reaction temperature (° C.), as a WABT, in the range of from about 490-550, 490-510, 490-540; 500-550 or 520-540;

a reaction inlet pressure (barg) in the range of from about 1.5-50 or 1.5-20;

a reaction outlet pressure (barg) in the range of from about 1.0-49 or 1-20;

a hydrogen to hydrocarbon molar ratio in the range of from about 2:1-5:1.

Cyclic and CCR process designs include online catalyst regeneration or replacement, and accordingly the lower pressure ranges as indicated above are suitable. For instance, CCRs can operate in the range of about 5 bar, while semi regenerative systems operate at the higher end of the above ranges, with cyclic designs typically operating at a pressure higher than CCRs and lower than semi regenerative systems.

An effective quantity of reforming catalyst is provided. Such catalyst include mono-functional or bi-functional reforming catalyst which generally contain one or more active metal component of metals or metal compounds (oxides or sulfides) selected from the Periodic Table of the Elements IUPAC Groups 8-10. A bi-functional catalyst has both metal sites and acidic sites. In certain embodiments, the active metal component can include one or more of platinum, rhenium, gold, palladium, germanium, nickel, silver, tin, iridium or halides. The active metal component is typically deposited or otherwise incorporated on a support, such as amorphous alumina, amorphous silica alumina, zeolites, or combinations thereof. In certain embodiments, platinum or platinum alloy supported on alumina or silica or silica-alumina are the reforming catalyst. Effective liquid hourly space velocity values ($h^{-1}$), on a fresh feed basis relative to the hydrotreating catalysts, are in the range of from about 0.5-4, 0.5-2, 0.5-3, 1-3, 1-4, 1-2, 1.5-4 or 1.5-3. Suitable reforming catalysts used in the reforming reaction zone 414 have an expected lifetime in the range of about 6-18, 12-26, 18-54 or 24-72 months.

In certain embodiments, and with reference to FIG. 16, to increase production of gasoline fuel components, the reformate stream is passed to separation and hydrogenation steps to reduce the total benzene content. For instance, instead of passing all or a portion of the total reformate stream 426 to the aromatics extraction zone, it is passed to a reformate splitter 430 and separated into one or more relatively benzene-rich fractions 434 and one or more relatively benzene-lean fractions 432 and 436. Typically, the relatively benzene-rich middle fraction 434, known as a "benzene heart cut," comprises about 10-20 vol % of the total reformate and contains about 20-30 vol % benzene. In contrast, the relatively benzene-lean heavy reformate bottom fraction 436 comprises about 40-80 V % of the total reformate and has a benzene content generally in the range of from about 0.3-1 vol %, which is sufficiently low to be passed to a gasoline pool 444 without further processing. The light reformate top fraction 432 which includes about 10-25 vol % of the total reformate, contains about 5-30 vol % benzene and is recovered or blended with other product pools.

The heart cut fraction 434, which contains a majority of the benzene content of total reformate stream 426, can be passed to a hydrogenation unit 438, also referred to as a benzene saturation unit, or directly to the aromatics extraction unit. Hydrogenation reactions occur in the presence of a predetermined amount of hydrogen gas 440 for conversion reactions including conversion of benzene to cyclohexane, and for the production of a benzene-lean and in certain embodiments an essentially benzene-free, gasoline blending component 442.

All or a portion of the benzene-lean blending component 442 can be mixed with the remaining gasoline pool constituents including the benzene-lean heavy reformate bottom fraction 436. For instance, when blended with the heavy reformate fraction 432 which can contain up to 1 vol % benzene, a final gasoline product can be recovered which contains less than about 1 vol % benzene. Further, all or a portion of benzene-lean blending component 442 can be routed to the mixed feed steam cracking zone 230. All of a portion of the light benzene lean fraction 432 can be routed to a gasoline pool or to the mixed feed steam cracking zone 230. All or a portion of the heavy benzene lean fraction 436 can be routed to the aromatics extraction zone 620 or to a gasoline pool.

In certain embodiments to maximize production of petrochemicals: all, a substantial portion, a significant portion or a major portion of the benzene-lean heavy reformate bottom fraction 436 is passed to the aromatics extraction zone, and any remainder can be passed to the gasoline pool; all, a substantial portion, a significant portion or a major portion of light reformate top fraction 432 is passed to the mixed feed steam cracking zone 230, and any remainder can be passed to the gasoline pool; and all, a substantial portion, a significant portion or a major portion of the benzene-lean blending component 442 can be routed to the mixed feed steam cracking zone 230, and any remainder can be passed to the gasoline pool.

A typical gasoline blending pool includes $C_4$ and heavier hydrocarbons having boiling points of less than about 205° C. In the catalytic reforming process, paraffins and naphthenes are restructured to produce isomerized paraffins and aromatics of relatively higher octane numbers. The catalytic reforming converts low octane n-paraffins to i-paraffins and naphthenes. Naphthenes are converted to higher octane aromatics. The aromatics are left essentially unchanged or some may be hydrogenated to form naphthenes due to reverse reactions taking place in the presence of hydrogen.

In certain embodiments, the hydrogenation unit 438 operating conditions include a reaction temperature (° C.) in the range of from about 200-600, 225-600, 250-600, 400-600, 200-550, 225-550, 250-550 or 400-550; and a reaction pressure (barg) in the range of from about 5-50, 15-50, 20-50, 5-45, 15-45, 20-45, 30-50, 30-45 or 30-50. The hydrogenation unit 438 is known, and can include but is not limited to systems be based on technology commercially available from Honeywell UOP, US; Axens, IFP Group Technologies, FR; or GTC Technology US, LLC, US.

An effective quantity of catalyst having a suitable level of active materials possessing hydrogenation functionality is provided in the benzene saturation unit 438. Such catalyst generally contain one or more active metal component of metals or metal oxides, selected from the Periodic Table of the Elements IUPAC Groups 6-10. In certain embodiments, the active metal component is one or more of nickel and platinum. The active metal component is typically deposited or otherwise incorporated on a support, such as amorphous alumina, amorphous silica alumina, zeolites, or combinations thereof. Effective liquid hourly space velocity values ($h^{-1}$), on a fresh feed basis relative to the benzene saturation unit catalysts, are in the range of from about 0.1-10.0, 0.1-5.0, 0.1-2.0, 0.3-10.0, 0.3-5.0, 0.3-2.0, 0.5-10.0, 0.5-5.0, 0.5-2.0 or 0.8-1.2. Suitable hydrotreating catalysts used in the benzene saturation unit 438 have an expected lifetime in the range of about 28-44, 34-44, 28-38 or 34-38 months.

Figure 17:
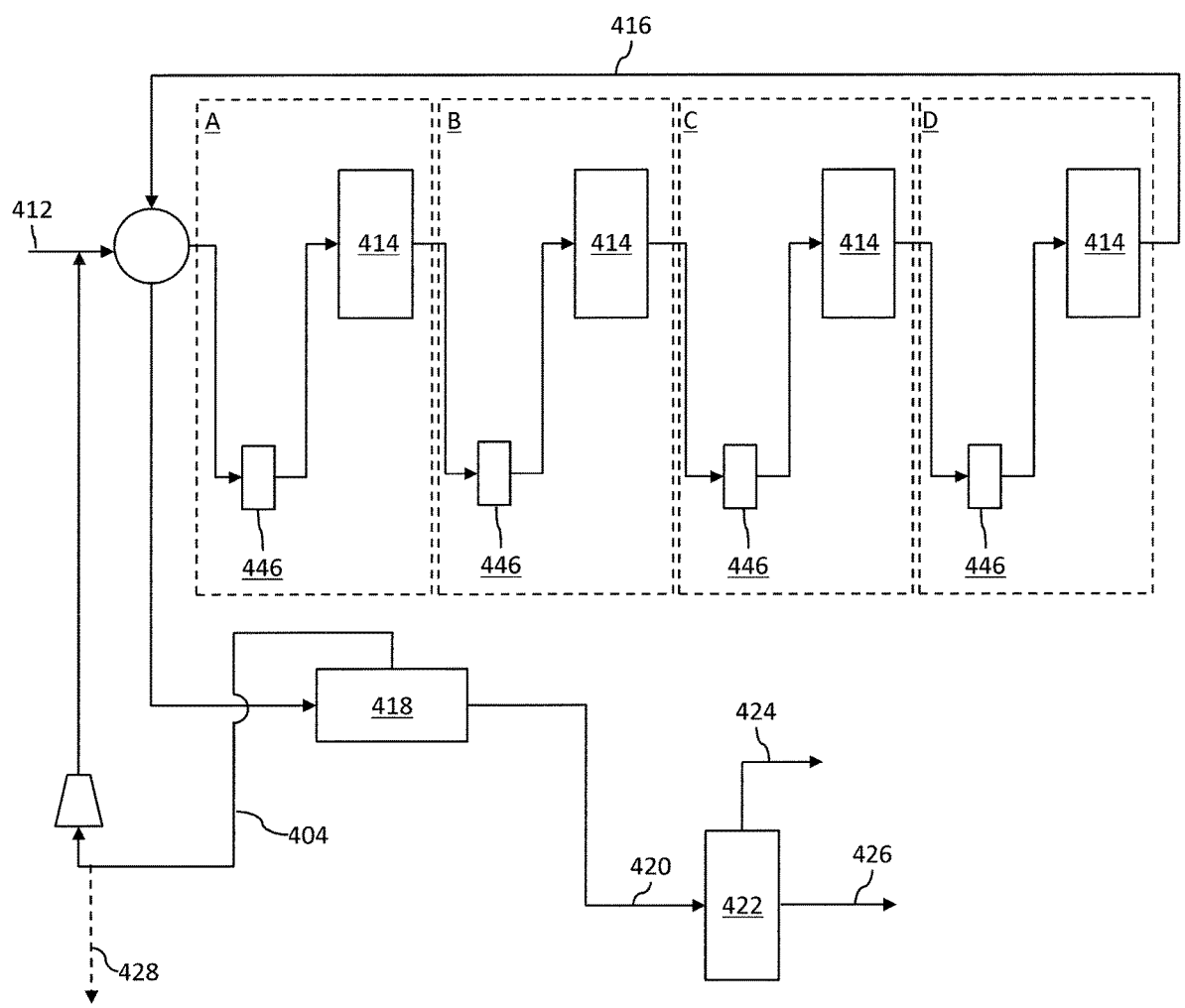
FIG. 17 schematically depicts operation of a catalytic reforming zone in another embodiment.

Referring to FIG. 17, another embodiment of a catalytic reforming system 414 is schematically depicted. A series of reactors 414 are provided. A feedstock, hydrotreated naphtha 412, is heat exchanged with a hot reformate stream 416 to increase the temperature of the feed. The heated feedstock is treated in a series of reaction zones containing reformer reactors 414, shown in the exemplary embodiment as zones A-D, although fewer or more zones can be used. The hot reformate stream 416 contains hot product hydrogen and reformate.

The reforming reactions are endothermic resulting in the cooling of reactants and products, requiring heating of effluent, typically by direct-fired furnaces 446, prior to charging as feed to a subsequent reforming reactor 414. As a result of the very high reaction temperatures, catalyst particles are deactivated by the formation of coke on the catalyst which reduces the available surface area and active sites for contacting the reactants.

Hot product hydrogen and reformate stream 416 passes through the heat exchanger and then to separator 418 for recovery of hydrogen stream 404 and a separator bottoms stream 420. Recovered hydrogen stream 404 is split with a portion compressed and recycled back to the reformer reactors, and excess hydrogen 428. The separator bottoms stream 420 is sent to a stabilizer column 422 to produce a light end stream 424 and a reformate stream 426.

As shown, the first middle distillate stream 118 is processed in a kerosene sweetening zone 170, to remove unwanted sulfur compounds, as is well-known. Treated kerosene is recovered as a kerosene fuel product 172, for instance, jet fuel compliant with Jet A or Jet A-1 specifications, and optionally other fuel products. In certain embodiments herein, all or a portion of the first middle distillate fraction 116 is not used for fuel production, but rather is used as a feed for distillate hydroprocessing so as to produce additional feed for the mixed feed steam cracking zone 230.

For instance, a suitable kerosene sweetening zone 170 can include, but is not limited to, systems based on Merox™ technology (Honeywell UOP, US), Sweetn'K technology (Axens, IFP Group Technologies, FR) or Thiolex™ technology (Merichem Company, US). Processes of these types are well-established commercially and appropriate operating conditions are well known to produce kerosene fuel product 172 and disulfide oils as by-product. In certain kerosene sweetening technologies impregnated carbon is utilized as catalyst to promote conversion to disulfide oil. In certain embodiments, common treatment of sour water from the kerosene sweetening zone 170 and other unit operations is employed to maximize process integration.

For example, one arrangement of a kerosene sweetening zone includes caustic wash of the kerosene feed for residual $H_2S$ removal, employing an electrostatic coalescer (for instance using 10 degrees Baumé). The reactor vessel containing an effective quantity of activated carbon catalyst utilizes air in conjunction with the caustic solution to affect the oxidation of mercaptan to disulfides. Caustic is separated from treated kerosene in the bottom section of the reactor.

After water washing, kerosene product passes upwards through one of two parallel salt filters to remove free water and some soluble water. The kerosene product passes downward through one of two parallel clay filters for removal of solids, moisture, emulsions and surfactants, to ensure that the kerosene product meets haze, color stability and water separation specifications, for instance, compliant with Jet A specifications.

The second middle distillate stream 120 and the third middle distillate stream 128 are processed in a diesel hydrotreating zone 180 in the presence of an effective amount of hydrogen obtained from recycle within the diesel hydrotreating zone 180 and make-up hydrogen 186. In certain embodiments, all or a portion of the make-up hydrogen 186 is derived from a steam cracker product hydrogen 210 stream from the olefins recovery train 270. A suitable hydrotreating zone 180 can include, but is not limited to, systems based on technology commercially available from Honeywell UOP, US; Chevron Lummus Global LLC (CLG), US; Axens, IFP Group Technologies, FR; Haldor Topsoe A/S, DK; or joint technology from KBR, Inc, US, and Shell Global Solutions, US.

The diesel hydrotreating zone 180 operates under conditions effective for removal of a significant amount of the sulfur and other known contaminants, for instance, to meet necessary sulfur specifications for a diesel fuel product 182, for instance, diesel fuel compliant with Euro V diesel standards. In addition, the hydrotreated naphtha fraction 184 (sometimes referred to as wild naphtha) is recovered from the diesel hydrotreating zone 180, which is routed to the mixed feed steam cracking zone 230 as one of plural steam cracking feed sources. Effluent off-gases are recovered from the diesel hydrotreating zone 180 and are passed to the olefins recovery train, the saturated gas plant as part of the other gases stream 156, and/or directly to a fuel gas system. Liquefied petroleum gas can be recovered from the diesel hydrotreating zone 180 and routed to the mixed feed steam cracking zone, the olefins recovery train and/or the saturated gas plant. In certain embodiments, the hydrotreated naphtha fraction 184 is routed through the crude complex 100, alone, or in combination with other wild naphtha fractions from within the integrated process. In embodiments in which hydrotreated naphtha fraction 184 is routed through the crude complex 100, all or a portion of the liquefied petroleum gas produced in the diesel hydrotreating zone 180 can be passed with the hydrotreated naphtha fraction 184. In certain embodiments, all, a substantial portion or a significant portion of the wild naphtha 184 is routed to the mixed feed steam cracking zone 230 (directly or through the crude complex 100).

The diesel hydrotreating zone 180 can optionally process other fractions from within the complex (not shown). In embodiments in which a kerosene sweetening zone 170 is used, all or a portion of the disulfide oil can be additional feed to the diesel hydrotreating zone 180. Further, all or a portion of the first middle distillate fraction 116 can be additional feed to the diesel hydrotreating zone 180. Additionally, all or a portion of distillates from the vacuum gas oil hydroprocessing zone, and/or all or a portion of distillates from the optional vacuum residue treatment zone, can be routed to the diesel hydrotreating zone 180. Any portion of distillates not routed to the diesel hydrotreating zone 180 can be passed to the crude complex 100 or routed to the mixed feed steam cracking zone 230. Further, all or a portion of light pyrolysis oil can be routed to the diesel hydrotreating zone 180.

In certain embodiments, the diesel hydrotreating zone 180 also processes at least a portion of the light cycle oil 708 from the high olefinic fluid catalytic cracking zone 700. Any portion of the light cycle oil 708 not routed to the diesel hydrotreating zone 180 can optionally be passed to a fuel oil pool and/or processed in the integrated gas oil hydroprocessing zone. For example, no more than 0-30, 0-25, 0-20, 5-30, 5-25, 5-20, 10-30, 10-25, or 10-20 wt % of the total light cycle oil 708 from the high olefinic fluid catalytic cracking zone 700 can be routed to the diesel hydrotreating zone 180.

The diesel hydrotreating zone 180 can contain one or more fixed-bed, ebullated-bed, slurry-bed, moving bed, continuous stirred tank (CSTR) or tubular reactors, in series and/or parallel arrangement. In certain embodiments, the diesel hydrotreating zone 180 contains a layered bed reactor with three catalyst beds and having inter-bed quench gas, and employs a layered catalyst system with the layer of hydrodewaxing catalyst positioned between beds of hydrotreating catalyst. Additional equipment, including exchangers, furnaces, feed pumps, quench pumps, and compressors to feed the reactor(s) and maintain proper operating conditions, are well known and are considered part of the diesel hydrotreating zone 180. In addition, equipment, including pumps, compressors, high temperature separation vessels, low temperature separation vessels and the like to separate reaction products and provide hydrogen recycle within the diesel hydrotreating zone 180, are well known and are considered part of the diesel hydrotreating zone 180.

In certain embodiments, the diesel hydrotreating zone 180 operating conditions include:

a reactor inlet temperature (° C.) in the range of from about 296-453, 296-414, 296-395, 336-453, 336-414, 336-395, 355-453, 355-414, 355-395 or 370-380;

a reactor outlet temperature (° C.) in the range of from about 319-487, 319-445, 319-424, 361-487, 361-445, 361-424, 382-487, 382-445, 382-424 or 400-406;

a start of run (SOR) reaction temperature (° C.), as a weighted average bed temperature (WABT), in the range of from about 271-416, 271-379, 271-361, 307-416, 307-379, 307-361, 325-416, 325-379, 325-361 or 340-346;

an end of run (EOR) reaction temperature (° C.), as a WABT, in the range of from about 311-476, 311-434, 311-414, 352-476, 352-434, 352-414, 373-476, 373-434, 373-414 or 390-396;

a reaction inlet pressure (barg) in the range of from about 48-72, 48-66, 48-63, 54-72, 54-66, 54-63, 57-72, 57-66 or 57-63;

a reaction outlet pressure (barg) in the range of from about 44-66, 44-60, 44-58, 49-66, 49-60, 49-58, 52-66, 52-60 or 52-58;

a hydrogen partial pressure (barg) (outlet) in the range of from about 32-48, 32-44, 32-42, 36-48, 36-44, 36-42, 38-48, 38-44 or 38-42;

a hydrogen treat gas feed rate (standard liters per liter of hydrocarbon feed, SLt/Lt) up to about 400, 385, 353 or 337, in certain embodiments from about 256-385, 256-353, 256-337, 289-385, 289-353, 289-337, 305-385, 305-353 or 305-337;

a hydrogen quench gas feed rate (SLt/Lt) up to about 100, 85, 78 or 75, in certain embodiments from about 57-85, 57-78, 57-75, 64-85, 64-78, 64-75, 68-85, 68-78, or 68-75; and a make-up hydrogen feed rate (SLt/Lt) up to about 110, 108, 100 or 95, in certain embodiments from about 70-108, 70-100, 70-95, 80-108, 80-100, 80-95, 85-108, 85-100 or 85-95.

An effective quantity of hydrotreating catalyst is provided in the diesel hydrotreating zone 180, including those possessing hydrotreating functionality and which generally contain one or more active metal component of metals or metal compounds (oxides or sulfides) selected from the Periodic Table of the Elements IUPAC Groups 6-10. In certain embodiments, the active metal component is one or more of Co, Ni, W and Mo. The active metal component is typically deposited or otherwise incorporated on a support, such as amorphous alumina, amorphous silica alumina, zeolites, or combinations thereof. The catalyst used in the diesel hydrotreating zone 180 can include one or more catalyst selected from Co/Mo, Ni/Mo, Ni/W, and Co/Ni/Mo. Combinations of one or more of Co/Mo, Ni/Mo, Ni/W and Co/Ni/Mo, can also be used. The combinations can be composed of different particles containing a single active metal species, or particles containing multiple active species. In certain embodiments, Co/Mo hydrodesulfurization catalyst is suitable. Effective liquid hourly space velocity values ($h^{-1}$), on a fresh feed basis relative to the hydrotreating catalysts, are in the range of from about 0.1-10.0, 0.1-5.0, 0.1-2.0, 0.3-10.0, 0.3-5.0, 0.3-2.0, 0.5-10.0, 0.5-5.0, 0.5-2.0 or 0.8-1.2. Suitable hydrotreating catalysts used in the diesel hydrotreating zone 180 have an expected lifetime in the range of about 28-44, 34-44, 28-38 or 34-38 months.

In certain embodiments, an effective quantity of hydrodewaxing catalyst is also added. In such embodiments, effective hydrodewaxing catalysts include those typically used for isomerizing and cracking paraffinic hydrocarbon feeds to improve cold flow properties, such as catalysts comprising Ni, W, or molecular sieves or combinations thereof. Catalyst comprising Ni/W, zeolite with medium or large pore sizes, or a combination thereof are suitable, along with catalyst comprising aluminosilicate molecular sieves such as zeolites with medium or large pore sizes. Effective commercial zeolites include for instance ZSM-5, ZSM-11, ZSM-12, ZSM-22, ZSM-23, ZSM 35, and zeolites of type beta and Y. Hydrodewaxing catalyst is typically supported on an oxide support such as $Al_2O_3$, $SiO_2$, $ZrO_2$, zeolites, zeolite-alumina, alumina-silica, alumina-silica-zeolite, activated carbon, and mixtures thereof. Effective liquid hourly space velocity values ($h^{-1}$), on a fresh feed basis relative to the hydrodewaxing catalyst, are in the range of from about 0.1-12.0, 0.1-8.0, 0.1-4.0, 0.5-12.0, 0.5-8.0, 0.5-4.0, 1.0-12.0, 1.0-8.0, 1.0-4.0 or 1.6-2.4. Suitable hydrodewaxing catalysts used in the diesel hydrotreating zone 180 have an expected lifetime in the range of about 28-44, 34-44, 28-38 or 34-38 months.

In high capacity operations, two or more parallel trains of reactors are utilized. In such embodiments, the flow in the diesel hydrotreating zone 180 is split after the feed pump into parallel trains, wherein each train contains feed/effluent heat exchangers, feed heater, a reactor and the hot separator. Each reactor contains three catalyst beds with inter-bed quench gas. A layered catalyst system is used with the layer of hydrodewaxing catalyst positioned between beds of hydrotreating catalyst. The trains recombine after the hot separators. Tops from the hot separators are combined and passed to a cold separator. Bottoms from the hot separators and from the cold separator are passed to a product stripper to produce stabilized ultra low sulfur diesel and wild naphtha. Tops from the cold separator are subjected to absorption and amine scrubbing. Recycle hydrogen is recovered, and passed (along with make-up hydrogen) to the reaction zone as treat gas and quench gas.

VGO 162 from the vacuum distillation zone 160 (or separate LVGO and HVGO fractions) is/are processed in a gas oil hydroprocessing zone 300 (FIG. 12]) or 320 (FIG. 13]) in the presence of an effective amount of hydrogen obtained from recycle within the gas oil hydroprocessing zone and make-up hydrogen 302. In certain embodiments, all or a portion of the make-up hydrogen 302 is derived from the steam cracker hydrogen stream 210 from the olefins recovery train 270. In certain embodiments (not shown in FIGS. 12 and 13), all or a portion of the heavy middle distillate fraction, such as the third middle distillate fraction 126, e.g., atmospheric gas oil from the atmospheric distillation zone 110, can also be treated in the gas oil hydroprocessing zone, for instance, a full range AGO, or a fraction thereof such as a fourth middle distillate stream 130, such as heavy atmospheric gas oil. Further, a portion of the third middle distillate fraction 126 can be routed to the gas oil hydroprocessing zone, while the remainder is routed to high olefinic fluid catalytic cracking zone 700, without passing through the vacuum gas oil hydroprocessing zone.

In accordance with the process herein, the severity of the gas oil hydroprocessing operation can be used to moderate the relative yield of olefin and aromatic chemicals from the overall complex and improve the economic threshold of cracking heavy feeds. This application of a gas oil hydroprocessing zone. as a chemical yield control mechanism, is uncommon in the industry, where fuels products are typically the product objectives.

In a hydrotreating mode of operation, as shown in FIG. 12, a vacuum gas oil hydrotreating zone 300 operates under suitable hydrotreating conditions, and generally produces off-gas and light ends (not shown), a wild naphtha stream 306 and hydrotreated gas oil 304. Effluent off-gases are recovered from the gas oil hydrotreating zone 300 and are passed to the olefins recovery train, the saturated gas plant as part of the other gases stream 156, and/or directly to a fuel gas system. Liquefied petroleum gas can be recovered from the gas oil hydrotreating zone 300 and routed to the mixed feed steam cracking zone, the olefins recovery train and/or the saturated gas plant. The naphtha fraction 306 is routed to the mixed feed steam cracking zone 230. In certain embodiments, the hydrotreated naphtha fraction 306 is routed through the crude complex 100, alone, or in combination with other wild naphtha fractions from within the integrated process. In embodiments in which hydrotreated naphtha fraction 306 is routed through the crude complex 100, all or a portion of the liquefied petroleum gas produced in the gas oil hydrotreating zone 300 can be passed with the hydrotreated naphtha fraction 306. Hydrotreated gas oil 304 is routed to the high olefinic fluid catalytic cracking zone 700. In certain embodiments, as shown in FIG. 10 described below, in addition to or in conjunction with the hydrotreated naphtha fraction 306, all or a portion of the hydrotreated distillates and naphtha from the gas oil hydrotreating zone 300 are passed to the diesel hydrotreating zone 180.

The gas oil hydrotreating zone 300 generally operates under conditions effective for removal of a significant amount of the sulfur and other known contaminants, and for conversion of the VGO 162 feed into a major proportion of hydrotreated gas oil 304 that is passed to the high olefinic fluid catalytic cracking zone 700, and minor proportions of distillates and hydrotreated naphtha 308. The hydrotreated gas oil fraction 304 generally contains the portion of the vacuum gas oil hydrotreater 300 effluent that is at or above the AGO, H-AGO or VGO range.

For instance, a suitable gas oil hydrotreating zone 300 can include, but is not limited to, systems based on technology commercially available from Honeywell UOP, US; Chevron Lummus Global LLC (CLG), US; Axens, IFP Group Technologies, FR; or Shell Global Solutions, US.

The gas oil hydrotreating zone 300 can contain one or more fixed-bed, ebullated-bed, slurry-bed, moving bed, continuous stirred tank (CSTR) or tubular reactors, in series and/or parallel arrangement. Additional equipment, including exchangers, furnaces, feed pumps, quench pumps, and compressors to feed the reactor(s) and maintain proper operating conditions, are well known and are considered part of the gas oil hydrotreating zone 300. In addition, equipment, including pumps, compressors, high temperature separation vessels, low temperature separation vessels and the like to separate reaction products and provide hydrogen recycle within the gas oil hydrotreating zone 300, are well known and are considered part of the gas oil hydrotreating zone 300.

An effective quantity of catalyst is provided in gas oil hydrotreating zone 300, including those possessing hydrotreating functionality, for hydrodesulfurization and hydrodenitrification. Such catalyst generally contain one or more active metal component of metals or metal compounds (oxides or sulfides) selected from the Periodic Table of the Elements IUPAC Groups 6-10. In certain embodiments, the active metal component is one or more of Co, Ni, W and Mo. The active metal component is typically deposited or otherwise incorporated on a support, such as amorphous alumina, amorphous silica alumina, zeolites, or combinations thereof. In certain embodiments, the catalyst used in the gas oil hydrotreating zone 300 includes one or more beds selected from Co/Mo, Ni/Mo, Ni/W, and Co/Ni/Mo. Combinations of one or more beds of Co/Mo, Ni/Mo, Ni/W and Co/Ni/Mo, can also be used. The combinations can be composed of different particles containing a single active metal species, or particles containing multiple active species. In certain embodiments, a combination of Co/Mo catalyst and Ni/Mo catalyst are effective for hydrodesulfurization and hydrodenitrification. One or more series of reactors can be provided, with different catalysts in the different reactors of each series. For instance, a first reactor includes Co/Mo catalyst and a second reactor includes Ni/Mo catalyst. Suitable catalyst used in the gas oil hydrotreating zone 300 have an expected lifetime in the range of about 28-44, 28-38, 34-44 or 34-38 months.

In certain embodiments, the gas oil hydrotreating zone 300 operating conditions include:

a reactor inlet temperature (° C.) in the range of from about 324-496, 324-453, 324-431, 367-496, 367-453, 367-431, 389-496, 389-453, 389-431 or 406-414;

a reactor outlet temperature (° C.) in the range of from about 338-516, 338-471, 338-449, 382-516, 382-471, 382-449, 404-516, 404-471, 404-449 or 422-430;

a start of run (SOR) reaction temperature (° C.), as a weighted average bed temperature (WABT), in the range of from about 302-462, 302-422, 302-402, 342-462, 342-422, 342-402, 362-462, 362-422, 362-402 or 378-384;

an end of run (EOR) reaction temperature (° C.), as a WABT, in the range of from about 333-509, 333-465, 333-443, 377-509, 377-465, 377-443, 399-509, 399-465, 399-443 or 416-424;

a reaction inlet pressure (barg) in the range of from about 91-137, 91-125, 91-119, 102-137, 102-125, 102-119, 108-137, 108-125, 108-119 or 110-116;

a reaction outlet pressure (barg) in the range of from about 85-127, 85-117, 85-111, 96-127, 96-117, 96-111, 100-127, 100-117 or 100-111;

a hydrogen partial pressure (barg) (outlet) in the range of from about 63-95, 63-87, 63-83, 71-95, 71-87, 71-83, 75-95, 75-87, 75-83 or 77-81;

a hydrogen treat gas feed rate (SLt/Lt) up to about 525, 510, 465 or 445, in certain embodiments from about 335-510, 335-465, 335-445, 380-510, 380-465, 380-445, 400-510, 400-465 or 400-445;

a hydrogen quench gas feed rate (SLt/Lt) up to about 450, 430, 392 or 375, in certain embodiments from about 285-430, 285-392, 285-375, 320-430, 320-392, 320-375, 338-430, 338-392 or 338-375;

a make-up hydrogen feed rate (SLt/Lt) up to about 220, 200, 180 or 172, in certain embodiments from about 130-200, 130-180, 130-172, 148-200, 148-180, 148-172, 155-200, 155-180 or 155-172; and liquid hourly space velocity values ($h^{-1}$), on a fresh feed basis relative to the hydrotreating catalysts, in the range of from about 0.1-10.0, 0.1-5.0, 0.1-2.0, 0.3-10.0, 0.3-5.0, 0.3-2.0, 0.4-10.0, 0.4-5.0, 0.4-3.0 or 0.5-2.5.

An effective quantity of catalyst is provided in gas oil hydrotreating zone 300, including those possessing hydrotreating functionality, for hydrodesulfurization and hydrodenitrification. Such catalyst generally contain one or more active metal component of metals or metal compounds (oxides or sulfides) selected from the Periodic Table of the Elements IUPAC Groups 6-10. In certain embodiments, the active metal component is one or more of Co, Ni, W and Mo. The active metal component is typically deposited or otherwise incorporated on a support, such as amorphous alumina, amorphous silica alumina, zeolites, or combinations thereof. In certain embodiments, the catalyst used in the gas oil hydrotreating zone 300 includes one or more beds selected from Co/Mo, Ni/Mo, Ni/W, and Co/Ni/Mo. Combinations of one or more beds of Co/Mo, Ni/Mo, Ni/W and Co/Ni/Mo, can also be used. The combinations can be composed of different particles containing a single active metal species, or particles containing multiple active species. In certain embodiments, a combination of Co/Mo catalyst and Ni/Mo catalyst are effective for hydrodesulfurization and hydrodenitrification. One or more series of reactors can be provided, with different catalysts in the different reactors of each series. For instance, a first reactor includes Co/Mo catalyst and a second reactor includes Ni/Mo catalyst. Effective liquid hourly space velocity values ($h^{-1}$), on a fresh feed basis relative to the hydrotreating catalysts, are in the range of from about 0.1-10.0, 0.1-5.0, 0.1-2.0, 0.3-10.0, 0.3-5.0, 0.3-2.0, 0.4-10.0, 0.4-5.0, 0.4-3.0 or 0.5-2.5. Suitable catalyst used in the gas oil hydrotreating zone 300 have an expected lifetime in the range of about 28-44, 28-38, 34-44 or 34-38 months.

Under the above conditions and catalyst selections, exemplary products from the gas oil hydrotreating zone 300 include 1-30, 5-30, 2-27 or 5-27 wt % of effluent (relative to the feed to the gas oil hydrotreating zone 300) boiling at or below the atmospheric residue end boiling point, such as 370° C., including LPG, kerosene, naphtha, and atmospheric gas oil range components. The remaining bottoms fraction is the hydrotreated gas oil fraction, all or a portion of which can be effectively integrated as feed to the gas oil steam cracking zone 250 as described herein.

In additional embodiments, the gas oil hydrotreating zone 300 can operate under conditions effective for feed conditioning and to maximize targeted conversion to petrochemicals in the steam cracker complex. Accordingly, in certain embodiments severity conditions are selected that achieve objectives differing from those used for conventional refinery operations. That is, while typical VGO hydrotreating operates with less emphasis on conservation of liquid product yield, in the present embodiment VGO hydrotreating operates to produce a higher yield of lighter products which are intentionally recovered to maximize chemicals yield. In embodiments to maximize conversion to petrochemicals, the gas oil hydrotreating zone 300 operating conditions include:

a reactor inlet temperature (° C.) in the range of from about 461-496, 461-473, 485-496 or 473-485;

a reactor outlet temperature (° C.) in the range of from about 480-516, 480-489, 489-495 or 495-516;

a start of run (SOR) reaction temperature (° C.), as a weighted average bed temperature (WABT), in the range of from about 430-462, 430-440, 440-450 or 450-462;

an end of run (EOR) reaction temperature (° C.), as a WABT, in the range of from about 473-509, 484-495, 473-484 or 495-509;

a reaction inlet pressure (barg) in the range of from about 110-137, 113-137, 110-120, 120-129 or 129-137;

a reaction outlet pressure (barg) in the range of from about 104-118, 104-108, 112-118 or 108-112;

a hydrogen partial pressure (barg) (outlet) in the range of from about 76-95, 76-83, 83-89, or 89-95;

a hydrogen treat gas feed rate (SLt/Lt) up to about 525, 485, 490 or 520, in certain embodiments from about 474-520, 474-488, 488-500, or 500-520;

a hydrogen quench gas feed rate (SLt/Lt) up to about 450, 441, 416 or 429, in certain embodiments from about 400-441, 400-415, 415-430, or 430-441;

a make-up hydrogen feed rate (SLt/Lt) up to about 220, 200, 207 or 214, in certain embodiments from about 186-200, 190-200, 186-190, 190-195, or 195-200; and liquid hourly space velocity values ($h^{-1}$), on a fresh feed basis relative to the hydrotreating catalysts, in the range of from about 0.5-0.7, 0.5-0.55, 0.55-0.6, 0.6-0.65, 0.65-0.7.

Under the above conditions and catalyst selections, exemplary products from the gas oil hydrotreating zone 300 operating under conditions effective for feed conditioning and to maximize targeted conversion to petrochemicals in the steam cracker complex include 20-30, 22-28, 23-27 or 24-26 wt % of effluent (relative to the feed to the gas oil hydrotreating zone 300) boiling at or below the atmospheric residue end boiling point, such as 370° C., including LPG, kerosene, naphtha, and atmospheric gas oil range components. The remaining bottoms fraction is the hydrotreated gas oil fraction, all or a portion of which can be effectively integrated as feed to the gas oil steam cracking zone 250 as described herein.

In certain embodiments, the gas oil hydrotreating zone 300 contains one or more trains of reactors, with a first reactor having two catalyst beds with two quench streams including an inter-bed quench stream, and a second reactor (lag reactor) having one catalyst bed with a quench stream. In high capacity operations, two or more parallel trains of reactors are utilized. In such embodiments, the flow in gas oil hydrotreating zone 300 is split after the feed pump into parallel trains, wherein each train contains feed/effluent heat exchangers, feed heater, a reactor and the hot separator. The trains recombine after the hot separators. Tops from the hot separators are combined and passed to a cold separator. Bottoms from the hot separators are passed to a hot flash drum. Bottoms from the cold separator and tops from the hot flash drum are passed to a low pressure flash drum to remove off-gases. Hot flash liquid bottoms and low pressure flash bottoms are passed to a stripper to recover hydrotreated gas oil and wild naphtha. Tops from the cold separator are subjected to absorption and amine scrubbing. Recycle hydrogen is recovered, and passed (along with make-up hydrogen) to the reaction zone as treat gas and quench gas.

FIG. 13 depicts a hydrocracking mode of operation for treatment of the vacuum gas oil. Hydrocracking processes are used commercially in a large number of petroleum refineries. They are used to process a variety of feeds boiling above the atmospheric gas oil range (for example, in the range of about 370 to 520° C.) in conventional hydrocracking units and boiling above the vacuum gas oil range (for example, above about 520° C.) in residue hydrocracking units. In general, hydrocracking processes split the molecules of the feed into smaller, i.e., lighter, molecules having higher average volatility and economic value. Additionally, hydrocracking processes typically improve the quality of the hydrocarbon feedstock by increasing the hydrogen-to-carbon ratio and by removing organosulfur and organonitrogen compounds. The significant economic benefit derived from hydrocracking processes has resulted in substantial development of process improvements and more active catalysts.

Three major hydrocracking process schemes include single-stage once through hydrocracking, series-flow hydrocracking with or without recycle, and two-stage recycle hydrocracking. Single-stage once through hydrocracking is the simplest of the hydrocracker configuration and typically occurs at operating conditions that are more severe than hydrotreating processes, and less severe than conventional higher pressure hydrocracking processes. It uses one or more reactors for both treating steps and cracking reaction, so the catalyst must be capable of both hydrotreating and hydrocracking. This configuration is cost effective, but typically results in relatively low product yields (for example, a maximum conversion rate of about 50 wt %). Single stage hydrocracking is often designed to maximize mid-distillate yield over a single or dual catalyst systems. Dual catalyst systems can be used in a stacked-bed configuration or in two different reactors. The effluents are passed to a fractionator column to separate the $H_2S$, $NH_3$, light gases ($C_1$-$C_4$), naphtha and diesel products, boiling in the temperature range including and below atmospheric gas oil range fractions (for instance in the temperature range of 36-370° C.). The hydrocarbons boiling above the atmospheric gas oil range (for instance 370° C.) are typically unconverted oils. Any portion of these unconverted oils that are not recycled are drawn from a bottoms fraction in a gas oil hydrocracking zone 320 as a hydrogen-rich bleed stream and is effectively integrated as feed to the high olefinic fluid catalytic cracking zone 700 as described herein. In certain embodiments, unconverted oils can be processed in a lube oil production unit (not shown).

The gas oil hydrocracking zone 320 operates under mild, moderate or severe hydrocracking conditions, and generally produces off-gas and light ends (not shown), a wild naphtha stream 326, a diesel fuel fraction 322, and an unconverted oil fraction 324. Effluent off-gases are recovered from the gas oil hydrotreating zone 300 and are passed to the olefins recovery train, the saturated gas plant as part of the other gases stream 156, and/or directly to a fuel gas system. Liquefied petroleum gas can be recovered from the gas oil hydrocracking zone 320 and routed to the mixed feed steam cracking zone, the olefins recovery train and/or the saturated gas plant. The naphtha fraction 326 is routed to the mixed feed steam cracking zone 230. In certain embodiments, the naphtha fraction 326 is routed through the crude complex 100, alone, or in combination with other wild naphtha fractions from within the integrated process. In embodiments in which naphtha fraction 326 is routed through the crude complex 100, all or a portion of the liquefied petroleum gas produced in the gas oil hydrocracking zone 320 can be passed with the naphtha fraction 326. The unconverted oil fraction 324 is routed to the high olefinic fluid catalytic cracking zone 700. The diesel fuel fraction 322 is recovered as fuel, for instance, compliant with Euro V diesel standards, and can be combined with the diesel fuel fraction 182 from the diesel hydrotreating zone 180. Vacuum gas oil hydrocracker 320 can operate under mild, moderate or severe conditions, depending on factors including the feedstock and the desired degree of conversion The gasoil hydrocracking zone 320 can operate under mild, moderate or severe conditions, depending on factors including the feedstock and the desired degree of conversion. Such conditions are effective for removal of a significant amount of the sulfur and other known contaminants, and for conversion of the feed(s) into a major proportion of hydrocracked products and minor proportions of off-gases, light ends and unconverted product that is passed to the high olefinic fluid catalytic cracking zone 700.

For instance, a suitable vacuum gas oil hydrocracker zone 320 can include, but is not limited to, systems based on technology commercially available from Honeywell UOP, US; Chevron Lummus Global LLC (CLG), US; Axens, IFP Group Technologies, FR; or Shell Global Solutions, US.

The gas oil hydrocracking zone 320 can contain one or more fixed-bed, ebullated-bed, slurry-bed, moving bed, continuous stirred tank (CSTR) or tubular reactors, in series and/or parallel arrangement. Additional equipment, including exchangers, furnaces, feed pumps, quench pumps, and compressors to feed the reactor(s) and maintain proper operating conditions, are well known and are considered part of the gas oil hydrocracking zone 320. In addition, equipment, including pumps, compressors, high temperature separation vessels, low temperature separation vessels and the like to separate reaction products and provide hydrogen recycle within the gas oil hydrocracking zone 320, are well known and are considered part of the gas oil hydrocracking zone 320.

Series-flow hydrocracking with or without recycle is one of the most commonly used configuration. It uses one reactor (containing both treating and cracking catalysts) or two or more reactors for both treating and cracking reaction steps. In a series-flow configuration the entire hydrocracked product stream from the first reaction zone, including light gases (typically $C_1$-$C_4$, $H_2S$, $NH_3$) and all remaining hydrocarbons, are sent to the second reaction zone. Unconverted bottoms from the fractionator column are recycled back into the first reactor for further cracking. This configuration converts heavy crude oil fractions such as vacuum gas oil, into light products and has the potential to maximize the yield of naphtha, kerosene and or diesel range hydrocarbons, depending on the recycle cut point used in the distillation section.

Two-stage recycle hydrocracking uses two reactors and unconverted bottoms from the fractionation column are passed to the second reactor for further cracking. Since the first reactor accomplishes both hydrotreating and hydrocracking, the feed to second reactor is virtually free of ammonia and hydrogen sulfide. This permits the use of high performance zeolite catalysts which are susceptible to poisoning by sulfur or nitrogen compounds.

Effective hydrocracking catalyst generally contain about 5-40 wt % based on the weight of the catalyst, of one or more active metal component of metals or metal compounds (oxides or sulfides) selected from the Periodic Table of the Elements IUPAC Groups 6-10. In certain embodiments, the active metal component is one or more of Mo, W, Co or Ni. The active metal component is typically deposited or otherwise incorporated on a support, such as amorphous alumina, amorphous silica alumina, zeolites, or combinations thereof. In certain embodiments, alone or in combination with the above metals, Pt group metals such as Pt and/or Pd, may be present as a hydrogenation component, generally in an amount of about 0.1-2 wt % based on the weight of the catalyst. Suitable hydrocracking catalyst have an expected lifetime in the range of about 18-30, 22-30, 18-26 or 22-26 months.

Exemplary products from the gas oil hydrocracking zone 320 include 27-99, 27-90, 27-82, 27-80, 27-75, 27-52, 27-48, 30-99, 30-90, 30-82, 30-80, 30-75, 30-52, 30-48, 48-99, 48-90, 48-82, 48-80, 48-75, 48-52, 78-99, 78-90, 78-85, 80-90 or 80-99 wt % of effluent (relative to the feed to the gas oil hydrocracking zone 320) boiling at or below the atmospheric residue end boiling point, such as 370° C., including LPG, kerosene, naphtha, and atmospheric gas oil range components. The remaining bottoms fraction is the unconverted oil fraction, all or a portion of which can be effectively integrated as feed to the high olefinic fluid catalytic cracking zone 700 as described herein.

Figure 18:
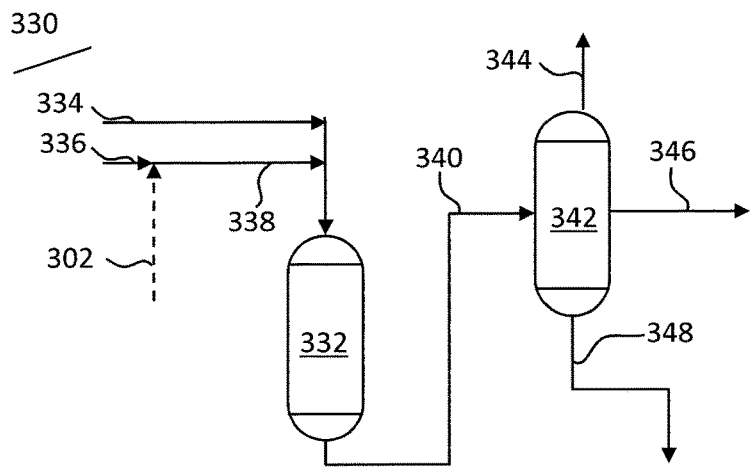
FIG. 18 schematically depicts a single reactor hydrocracking zone.

FIG. 18 schematically depicts an embodiment of a once-through single reactor hydrocracking zone 330 including a reaction zone 332 and a fractionating zone 342, which can as a mild conversion or partial conversion hydrocracker.

Reaction zone 332 generally includes one or more inlets in fluid communication with a source of initial feedstock 334 and a source of hydrogen gas 338. One or more outlets of reaction zone 332 that discharge effluent stream 340 is in fluid communication with one or more inlets of the fractionating zone 342 (typically including one or more high pressure and/or low pressure separation stages therebetween for recovery of recycle hydrogen, not shown).

Fractionating zone 342 includes one or more outlets for discharging gases 344, typically $H_2$, $H_2S$, $NH_3$, and light hydrocarbons ($C_1$-$C_4$); one or more outlets for recovering product 346, such as middle distillates naphtha and diesel products boiling in the temperature range including and below atmospheric gas oil range fractions (for instance in the temperature range of 36-370° C.); and one or more outlets for discharging bottoms 348 including hydrocarbons boiling above the atmospheric gas oil range (for instance 370° C.). In certain embodiments, the temperature cut point for bottoms 348 (and correspondingly the end point for the products 346) is a range corresponding to the upper temperature limit of the desired gasoline, kerosene and/or diesel product boiling point ranges for downstream operations.

In operation of the once-through single reactor hydrocracking zone 330, a feedstock stream 334 and a hydrogen stream 338 are charged to the reaction zone 332. Hydrogen stream 338 is an effective quantity of hydrogen to support the requisite degree of hydrocracking, feed type, and other factors, and can be any combination including, recycle hydrogen 336 from optional gas separation subsystems (not shown) associated with reaction zone 332, and/or derived from fractionator gas stream 344 and make-up hydrogen 302, if necessary. In certain embodiments, a reaction zone can contain multiple catalyst beds and can receive one or more quench hydrogen streams between the beds (not shown).

The reaction effluent stream 340 contains converted, partially converted and unconverted hydrocarbons. Reaction effluent stream 340 is passed to fractionating zone 342 (optionally after one or more high pressure and low pressure separation stages to recover recycle hydrogen), generally to recover gas and liquid products and by-products 344, 346, and separate a bottoms fraction 348. This stream 348 is routed to the high olefinic fluid catalytic cracking zone 700 as described herein.

Gas stream 344, typically containing $H_2$, $H_2S$, $NH_3$, and light hydrocarbons ($C_1$-$C_4$), is discharged and recovered and can be further processed. Effluent off-gases are passed to the olefins recovery train, the saturated gas plant as part of the other gases stream 156, and/or directly to a fuel gas system. Liquefied petroleum gas can be recovered and routed to the mixed feed steam cracking zone, the olefins recovery train and/or the saturated gas plant. One or more cracked product streams 346 are discharged via appropriate outlets of the fractionator and can be further processed and/or blended in downstream refinery operations to produce gasoline, kerosene and/or diesel fuel, or other petrochemical products.

In certain embodiments (not shown), fractionating zone 342 can operate as a flash vessel to separate heavy components at a suitable cut point, for example, a range corresponding to the upper temperature range of the desired gasoline, kerosene and/or diesel products for downstream operations. In certain embodiments, a suitable cut point is in the range of 350 to 450° C., 360 to 450° C., 370 to 450° C., 350 to 400° C., 360 to 400° C., 370 to 400° C., 350 to 380° C., or 360 to 380° C. The stream above that cut point is routed to the high olefinic fluid catalytic cracking zone 700 as described herein.

For instance, a suitable once-through single reactor hydrocracking zone 330 can include, but is not limited to, systems based on technology commercially available from Honeywell UOP, US; Chevron Lummus Global LLC (CLG), US; Axens, IFP Group Technologies, FR; or Shell Global Solutions, US.

The reactor arrangement in the once-through single reactor hydrocracking zone 330 can contain one or more fixed-bed, ebullated-bed, slurry-bed, moving bed, continuous stirred tank (CSTR), or tubular reactors, which can be in parallel arrangement. The once-through single reactor hydrocracking zone 330 can operate in a mild hydrocracking mode of operation or a partial conversion mode of operation. Additional equipment, including exchangers, furnaces, feed pumps, quench pumps, and compressors to feed the reactor (s) and maintain proper operating conditions, are well known and are considered part of the once-through single reactor hydrocracking zone 330. In addition, equipment, including pumps, compressors, high temperature separation vessels, low temperature separation vessels and the like to separate reaction products and provide hydrogen recycle within the once-through single reactor hydrocracking zone 330, are well known and are considered part of the once-through single reactor hydrocracking zone 330.

In certain embodiments, operating conditions for the reactor(s) in hydrocracking zone 330 using a once-through (single stage without recycle) configuration and operating in a mild hydrocracking mode include:

a reactor inlet temperature (° C.) in the range of from about 329-502, 329-460, 329-440, 372-502, 372-460, 372-440, 394-502, 394-460, 394-440 or 412-420;

a reactor outlet temperature (° C.) in the range of from about 338-516, 338-471, 338-450, 382-516, 382-471, 382-450, 400-516, 400-471, 400-450 or 422-430;

a start of run (SOR) reaction temperature, as a weighted average bed temperature (WABT), in the range of from about 310-475, 310-435, 310-415, 350-475, 350-435, 350-415, 370-475, 370-435, 370-415 or 390-397;

an end of run (EOR) reaction temperature, as a WABT, in the range of from about 338-516, 338-471, 338-450, 382-516, 382-471, 382-450, 400-516, 400-471, 400-450 or 422-430;

a reaction inlet pressure (barg) in the range of from about 108-161, 108-148, 108-141, 121-161, 121-148, 121-141, 128-161, 128-148, 128-141 or 131-137;

a reaction outlet pressure (barg) in the range of from about 100-150, 100-137, 100-130, 112-150, 112-137, 112-130, 118-150, 118-137 or 118-130;

a hydrogen partial pressure (barg) (outlet) in the range of from about 77-116, 77-106, 77-101, 87-116, 87-106, 87-101, 92-116, 92-106, 92-101 or 94-98;

a hydrogen treat gas feed rate (SLt/Lt) up to about 530, 510, 470 or 450, in certain embodiments from about 340-510, 340-470, 340-450, 382-510, 382-470, 382-450, 400-510, 400-470, 400-450 or 410-440;

a hydrogen quench gas feed rate (SLt/Lt) up to about 470, 427, 391 or 356, in certain embodiments from about 178-427, 178-214, 178-356, 214-321 or 178-391;

make-up hydrogen rate (SLt/Lt) up to about 225, 215, 200 or 190, in certain embodiments from about 143-215, 143-200, 143-190, 161-215, 161-200, 161-190, 170-215, 170-200 or 170-190; and liquid hourly space velocity values ($h^{-1}$), on a fresh feed basis relative to the hydrocracking catalysts, are in the range of from about 0.1-10.0, 0.1-5.0, 0.1-2.0, 0.3-10.0, 0.3-5.0, 0.3-2.0, 0.4-10.0, 0.4-5.0 or 0.5-3.0.

Under the above conditions and catalyst selections, exemplary products from the once-through single reactor hydrocracking zone 330 operating in a mild hydrocracking mode of operation include 27-52, 27-48, 30-50 or 30-52 wt % of effluent (relative to the feed to the gas oil hydrotreating zone 330) boiling at or below the atmospheric residue end boiling point, such as 370° C., including LPG, kerosene, naphtha, and atmospheric gas oil range components. The remaining bottoms fraction is the unconverted oil fraction, all or a portion of which can be effectively integrated as feed to the high olefinic fluid catalytic cracking zone 700 as described herein.

In certain embodiments, operating conditions for the reactor(s) in hydrocracking zone 330 using a once-through (single stage without recycle) configuration and operating in a partial conversion mode include:

a reactor inlet temperature (° C.) in the range of from about 340-502, 340-460, 340-440, 372-502, 372-460, 372-440, 394-502, 394-460, 394-440 or 412-420;

a reactor outlet temperature (° C.) in the range of from about 350-516, 350-471, 350-450, 382-516, 382-471, 382-450, 400-516, 400-471, 400-450 or 422-430;

a start of run (SOR) reaction temperature, as a weighted average bed temperature (WABT), in the range of from about 310-475, 310-435, 310-415, 350-475, 350-435, 350-415, 370-475, 370-435, 370-415 or 390-397;

an end of run (EOR) reaction temperature, as a WABT, in the range of from about 338-516, 338-471, 338-450, 382-516, 382-471, 382-450, 400-516, 400-471, 400-450 or 422-430;

a reaction inlet pressure (barg) in the range of from about 100-165, 100-150, 100-140, 120-165, 120-140, 130-165, 130-150, or 130-140;

a reaction outlet pressure (barg) in the range of from about 92-150, 92-137, 92-130, 112-150, 112-127, 112-130, 118-140, 118-130;

a hydrogen partial pressure (barg) (outlet) in the range of from about 80-120, 80-106, 80-101, 90-120, 90-106, 90-101, 100-120, or 100-115;

a hydrogen treat gas feed rate (SLt/Lt) up to about 677, 615, 587 or 573, in certain embodiments from about 503-615, 503-587, 503-573, 531-615, 531-587, 531-573, 545-615, 545-587, or 545-573;

a hydrogen quench gas feed rate (SLt/Lt) up to about 614, 558, 553 or 520, in certain embodiments from about 457-558, 457-533, 457-520, 482-558, 482-533, 482-520, 495-558, 495-533, or 495-520;

make-up hydrogen rate (SLt/Lt) up to about 305, 277, 264 or 252, in certain embodiments from about 204-277, 204-264, 204-252, 216-277, 216-264, 216-252, 228-277, 228-264, or 228-252; and liquid hourly space velocity values ($h^{-1}$), on a fresh feed basis relative to the hydrocracking catalysts, are in the range of from about 0.1-10.0, 0.1-5.0, 0.1-2.0, 0.3-10.0, 0.3-5.0, 0.3-2.0, 0.4-10.0, 0.4-5.0, 0.4-2.0 or 0.5-3.0.

Under the above conditions and catalyst selections, exemplary products from the once-through single reactor hydrocracking zone 330 operating as a partial conversion hydrocracker include 48-82, 50-80, 48-75, 50-75 wt % of effluent (relative to the feed to the gas oil hydrotreating zone 330) boiling at or below the atmospheric residue end boiling point, such as 370° C., including LPG, kerosene, naphtha, and atmospheric gas oil range components. The remaining bottoms fraction is the unconverted oil fraction, all or a portion of which can be effectively integrated as feed to the high olefinic fluid catalytic cracking zone 700 as described herein.

Figure 19:
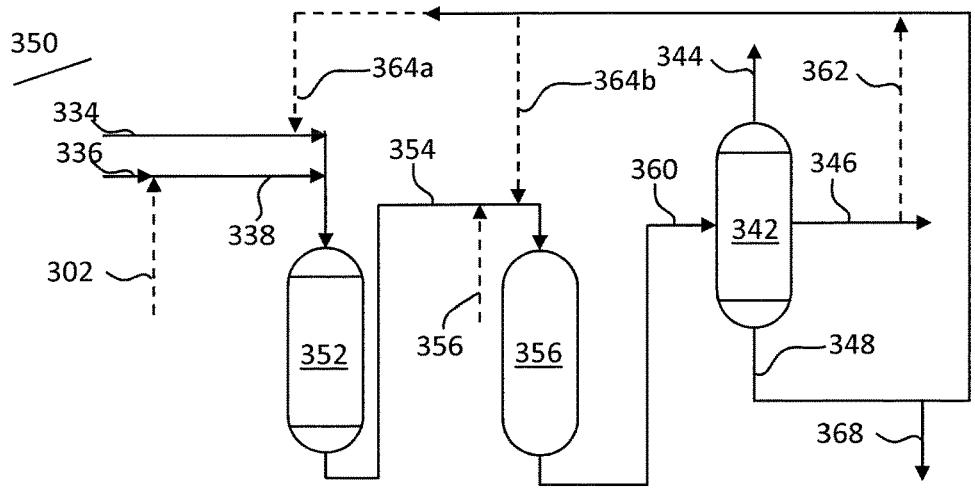
FIG. 19 schematically depicts a series-flow hydrocracking zone with recycle.

FIG. 19 schematically depicts another embodiment of a series flow hydrocracking zone 350, which operates as series-flow hydrocracking system with recycle to the first reactor zone, the second reactor zone, or both the first and second reactor zones. In general, series flow hydrocracking zone 350 includes a first reaction zone 352, a second reaction zone 358 and a fractionating zone 342.

First reaction zone 352 generally includes one or more inlets in fluid communication with a source of initial feedstock 334, a source of hydrogen gas 338, and in certain embodiments recycle stream 364a comprising all or a portion of the fractionating zone 342 bottoms stream 348 and optionally a portion of fractionating zone 342 product stream 362. One or more outlets of the first reaction zone 352 that discharge effluent stream 354 is in fluid communication with one or more inlets of the second reaction zone 358. In certain embodiments, the effluents 354 are passed to the second reaction zone 358 without separation of any excess hydrogen and light gases. In optional embodiments, one or more high pressure and low pressure separation stages are provided between the first and second reaction zones 352, 358 for recovery of recycle hydrogen (not shown).

The second reaction zone 358 generally includes one or more inlets in fluid communication with one or more outlets of the first reaction zone 352, optionally a source of additional hydrogen gas 356, and in certain embodiments a recycle stream 364b comprising all or a portion of the fractionating zone 342 bottoms stream 348 and optionally a portion of fractionating zone 342 product stream 362. One or more outlets of the second reaction zone 358 that discharge effluent stream 360 is in fluid communication with one or more inlets of the fractionating zone 342 (optionally having one or more high pressure and low pressure separation stages therebetween for recovery of recycle hydrogen, not shown).

Fractionating zone 342 includes one or more outlets for discharging gases 344, typically $H_2$, $H_2S$, $NH_3$, and light hydrocarbons ($C_1$-$C_4$); one or more outlets for recovering product 346, such as middle distillates naphtha and diesel products boiling in the temperature range including and below atmospheric gas oil range fractions (for instance in the temperature range of 36-370° C.); and one or more outlets for discharging bottoms 348 including hydrocarbons boiling above the atmospheric gas oil range (for instance about 370° C.), from which a bleed stream 368 is obtained in processes that do not operate with 100% recycle. In certain embodiments, the temperature cut point for bottoms 348 (and correspondingly the end point for the products 346) is a range corresponding to the upper temperature limit of the desired gasoline, kerosene and/or diesel product boiling point ranges for downstream operations.

In operation of the series flow hydrocracking zone 350, a feedstock stream 334 and a hydrogen stream 338 are charged to the first reaction zone 352. Hydrogen stream 338 is an effective quantity of hydrogen to support the requisite degree of hydrocracking, feed type, and other factors, and can be any combination including, recycle hydrogen 336 from optional gas separation subsystems (not shown) associated with reaction zones 352 and 358, and/or derived from fractionator gas stream 344 and make-up hydrogen 302. In certain embodiments, a reaction zone can contain multiple catalyst beds and can receive one or more quench hydrogen streams between the beds (not shown).

First reaction zone 352 operates under effective conditions for production of reaction effluent stream 354 which is passed to the second reaction zone 358 (optionally after one or more high pressure and low pressure separation stages to recover recycle hydrogen), optionally along with an additional hydrogen stream 356. Second reaction zone 358 operates under conditions effective for production of the reaction effluent stream 360, which contains converted, partially converted and unconverted hydrocarbons.

The reaction effluent stream 360 is passed to fractionating zone 342, generally to recover gas and liquid products and by-products 344, 346, and separate a bottoms fraction 348. A portion of the bottoms fraction 348, stream 368 is routed to the high olefinic fluid catalytic cracking zone 700 as described herein.

Gas stream 344, typically containing $H_2$, $H_2S$, $NH_3$, and light hydrocarbons ($C_1$-$C_4$), is discharged and recovered and can be further processed. Effluent off-gases are passed to the olefins recovery train, the saturated gas plant as part of the other gases stream 156, and/or directly to a fuel gas system. Liquefied petroleum gas can be recovered and routed to the mixed feed steam cracking zone, the olefins recovery train and/or the saturated gas plant. One or more cracked product streams 346 are discharged via appropriate outlets of the fractionator and can be further processed and/or blended in downstream refinery operations to produce gasoline, kerosene and/or diesel fuel, or other petrochemical products. In certain embodiments, a diesel fraction 362 derived from the one or more cracked product streams 346 can be integrated with the recycle streams to the reactors. This integration adds to the flexibility of the configuration between production of diesel fuel or petrochemicals from the product streams 346.

In certain embodiments (not shown), fractionating zone 342 can operate as a flash vessel to separate heavy components at a suitable cut point, for example, a range corresponding to the upper temperature range of the desired gasoline, kerosene and/or diesel products for downstream operations. In certain embodiments, a suitable cut point is in the range of 350 to 450° C., 360 to 450° C., 370 to 450° C., 350 to 400° C., 360 to 400° C., 370 to 400° C., 350 to 380°

C., or 360 to 380° C. The stream above that cut point is routed to the high olefinic fluid catalytic cracking zone 700 as described herein.

All or a portion of the fractionator bottoms stream 348 from the reaction effluent is recycled to the first or second reaction zones 352 and/or 358 (streams 364a and/or 364b). In certain embodiments, a portion of the fractionator bottoms from the reaction effluent is removed as bleed stream 368. Bleed stream 368 can be about 0-10 vol %, 1-10 vol %, 1-5 vol % or 1-3 vol % of the fractionator bottoms 348. This stream 368 is routed to the high olefinic fluid catalytic cracking zone 700 as described herein.

Accordingly, all or a portion of the fractionator bottoms stream 348 is recycled to the second reaction zone 358 as stream 364b, the first reaction zone 352 as stream 364a, or both the first and second reaction zones 352 and 358. For instance, stream 364a recycled to zone 352 comprises 0 to 100 vol %, in certain embodiments 0 to about 80 vol %, and in further embodiments 0 to about 50 vol % of stream 348, and stream 364b recycled to zone 358 comprises 0 to 100 vol %, in certain embodiments 0 to about 80 vol %, and in further embodiments 0 to about 50 vol % of stream 348. In certain embodiments, in which the recycle is at or approaches 100 vol %, recycle of the unconverted oil increases the yield of products suitable as feed to the mixed feed steam cracking zone 230.

For instance, a suitable series flow hydrocracking zone 350 can include, but is not limited to, systems based on technology commercially available from Honeywell UOP, US; Chevron Lummus Global LLC (CLG), US; Axens, IFP Group Technologies, FR; or Shell Global Solutions, US.

The reactor arrangement in the series flow hydrocracking zone 350 can contain one or more fixed-bed, ebullated-bed, slurry-bed, moving bed, continuous stirred tank (CSTR), or tubular reactors, which can be in parallel arrangement. Additional equipment, including exchangers, furnaces, feed pumps, quench pumps, and compressors to feed the reactor (s) and maintain proper operating conditions, are well known and are considered part of the series flow hydrocracking zone 350. In addition, equipment, including pumps, compressors, high temperature separation vessels, low temperature separation vessels and the like to separate reaction products and provide hydrogen recycle within the series flow hydrocracking zone 350, are well known and are considered part of the series flow hydrocracking zone 350.

In certain embodiments, operating conditions for the first reactor(s) in hydrocracking zone 350 using once-through series configuration operating in a partial conversion mode of operation include:

a reactor inlet temperature (° C.) in the range of from about 340-502, 340-460, 340-440, 372-502, 372-460, 372-440, 394-502, 394-460, 394-440 or 412-420;

a reactor outlet temperature (° C.) in the range of from about 350-516, 350-471, 350-450, 382-516, 382-471, 382-450, 400-516, 400-471, 400-450 or 422-430;

a start of run (SOR) reaction temperature, as a weighted average bed temperature (WABT), in the range of from about 310-475, 310-435, 310-415, 350-475, 350-435, 350-415, 370-475, 370-435, 370-415 or 390-397;

an end of run (EOR) reaction temperature, as a WABT, in the range of from about 338-516, 338-471, 338-450, 382-516, 382-471, 382-450, 400-516, 400-471, 400-450 or 422-430;

a reaction inlet pressure (barg) in the range of from about 100-165, 100-150, 100-140, 120-165, 120-140, 130-165, 130-150, or 130-140;

a reaction outlet pressure (barg) in the range of from about 92-150, 92-137, 92-130, 112-150, 112-127, 112-130, 118-140, 118-130;

a hydrogen partial pressure (barg) (outlet) in the range of from about 80-120, 80-106, 80-101, 90-120, 90-106, 90-101, 100-120, or 100-115;

a hydrogen treat gas feed rate (SLt/Lt) up to about 668, 607, 580 or 566, in certain embodiments from about 497-607, 497-580, 497-566, 525-607, 525-580, 525-566, 538-607, 538-580, or 538-566;

a hydrogen quench gas feed rate (SLt/Lt) up to about 819, 744, 711 or 694, in certain embodiments from about 609-744, 609-711, 609-694, 643-744, 643-711, 643-694, 660-744, 660-711, or 660-694;

make-up hydrogen rate (SLt/Lt) up to about 271, 246, 235 or 224, in certain embodiments from about 182-246, 182-235, 182-224, 192-246, 192-235, 192-224, 203-246, 203-235, or 203-224; and liquid hourly space velocity values ($h^{-1}$), on a fresh feed basis relative to the hydrocracking catalysts, are in the range of from about 0.1-10.0, 0.1-5.0, 0.1-2.0, 0.3-10.0, 0.3-5.0, 0.3-2.0, 0.4-10.0, 0.4-5.0, 0.4-2.0 or 0.5-1.5.

In certain embodiments, operating conditions for the second reactor(s) in hydrocracking zone 350 using once-through series configuration operating in a partial conversion mode of operation include:

In certain embodiments, partial conversion hydrocracking using once-through configuration operating conditions include:

a reactor inlet temperature (° C.) in the range of from about 340-502, 340-460, 340-440, 372-502, 372-460, 372-440, 394-502, 394-460, 394-440 or 412-420;

a reactor outlet temperature (° C.) in the range of from about 350-516, 350-471, 350-450, 382-516, 382-471, 382-450, 400-516, 400-471, 400-450 or 422-430;

a start of run (SOR) reaction temperature, as a weighted average bed temperature (WABT), in the range of from about 310-475, 310-435, 310-415, 350-475, 350-435, 350-415, 370-475, 370-435, 370-415 or 390-397;

an end of run (EOR) reaction temperature, as a WABT, in the range of from about 338-516, 338-471, 338-450, 382-516, 382-471, 382-450, 400-516, 400-471, 400-450 or 422-430;

a reaction inlet pressure (barg) in the range of from about 90-150, 90-130, 90-140, 110-150, 110-130, 110-145, or 130-150;

a reaction outlet pressure (barg) in the range of from about 85-140, 85-127, 100-140, 112-130, 112-140, or 118-130;

hydrogen partial pressure (barg) (outlet) in the range of from about 80-130, 80-120, 80-101, 90-130, 90-120, 90-101, 100-130, or 100-115;

a hydrogen treat gas feed rate (SLt/Lt) up to about 890, 803, 767 or 748, in certain embodiments from about 657-803, 657-767, 657-748, 694-803, 694-767, 694-748, 712-803, 712-767, or 712-748;

a hydrogen quench gas feed rate (SLt/Lt) up to about 850, 764, 729 or 712, in certain embodiments from about 625-764, 625-729, 625-712, 660-764, 660-729, 660-712, 677-764, 677-729, or 677-712;

make-up hydrogen rate (SLt/Lt) up to about 372, 338, 323 or 309, in certain embodiments from about 250-338, 250-323, 250-309, 264-338, 264-323, 264-309, 279-338, 279-323, or 279-309; and liquid hourly space velocity values ($h^{-1}$), on a fresh feed basis relative to the hydrocracking catalysts, are in the range of from about 0.1-10.0, 0.1-5.0, 0.1-2.0, 0.3-10.0, 0.3-5.0, 1.0-5.0, 2.0-4.0 or 1.0-3.0.

Under the above conditions and catalyst selections, exemplary products from the partial conversion hydrocracker using once-through configuration include 48-82, 50-80, 48-75 or 50-75 wt % of effluent boiling at or below the atmospheric residue end boiling point, such as 370° C., including LPG, kerosene, naphtha, and atmospheric gas oil range components. The remaining bottoms fraction is the unconverted oil fraction, all or a portion of which can be effectively integrated as feed to the high olefinic fluid catalytic cracking zone 700 as described herein.

Figure 20:
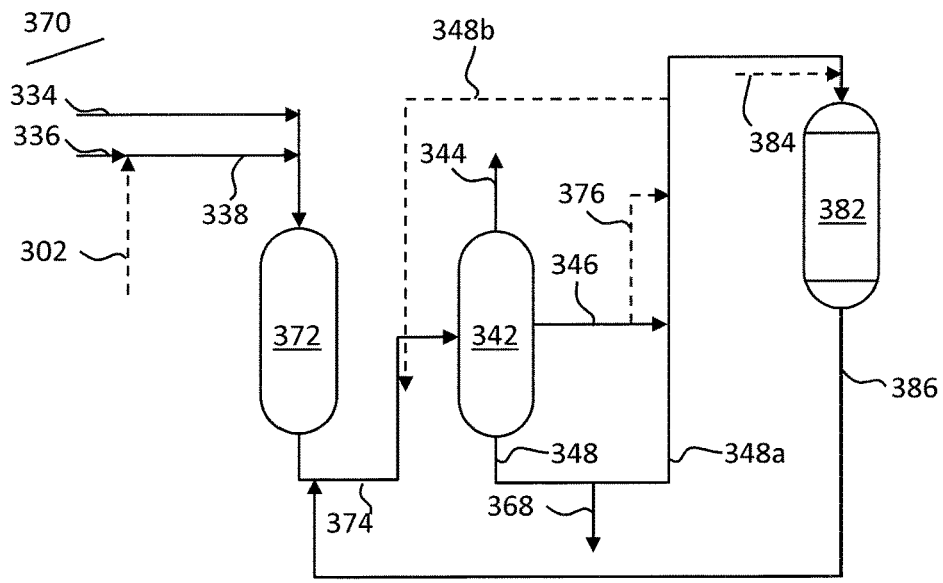
FIG. 20 schematically depicts a two-stage hydrocracking zone with recycle.

FIG. 20 schematically depicts another embodiment of an integrated hydrocracking unit operation, a two-stage with recycle hydrocracking zone 370, which operates as two-stage hydrocracking system with recycle. In general, hydrocracking zone 370 includes a first reaction zone 372, a second reaction zone 382 and a fractionating zone 342.

First reaction zone 372 generally includes one or more inlets in fluid communication with a source of initial feedstock 334 and a source of hydrogen gas 338. One or more outlets of the first reaction zone 372 that discharge effluent stream 374 are in fluid communication with one or more inlets of the fractionating zone 342 (optionally having one or more high pressure and low pressure separation stages therebetween for recovery of recycle hydrogen, not shown).

Fractionating zone 342 includes one or more outlets for discharging gases 344, typically $H_2S$, $NH_3$, and light hydrocarbons ($C_1$-$C_4$); one or more outlets for recovering product 346, such as naphtha and diesel products boiling in the temperature range including and below atmospheric gas oil range fractions (for instance in the temperature range of 36-370° C.); and one or more outlets for discharging bottoms 348 including hydrocarbons boiling above the atmospheric gas oil range (for instance about 370° C.), from which a bleed stream 368 is obtained in processes that do not operate with 100% recycle. In certain embodiments, the temperature cut point for bottoms 348 (and correspondingly the end point for the products 346) is a range corresponding to the upper temperature limit of the desired gasoline, kerosene and/or diesel product boiling point ranges for downstream operations.

The fractionating zone 342 bottoms outlet is in fluid communication with the one or more inlets of the second reaction zone 382 for recycle stream 348a derived from the bottoms stream 348. Recycle stream 348a can be all or a portion of the bottoms stream 348. In certain optional embodiments (as indicated by dashed lines in FIG. 20), a portion 348b is in fluid communication with one or more inlets of the first reaction zone 372.

Second reaction zone 382 generally includes one or more inlets in fluid communication with the fractionating zone 342 bottoms outlet portion 348a of bottoms 348, and a source of hydrogen gas 384. One or more outlets of the second reaction zone 382 that discharge effluent stream 386 are in fluid communication with one or more inlets of the fractionating zone 342 (optionally having one or more high pressure and low pressure separation stages therebetween for recovery of recycle hydrogen, not shown).

In operation of the two-stage hydrocracking zone 370, a feedstock stream 334 and a hydrogen stream 338 are charged to the first reaction zone 372. Hydrogen stream 338 is an effective quantity of hydrogen to support the requisite degree of hydrocracking, feed type, and other factors, and can be any combination including, recycle hydrogen 336 from optional gas separation subsystems (not shown) associated with reaction zones 372 and 382, and/or derived from fractionator gas stream 344 and make-up hydrogen 302. In certain embodiments, a reaction zone can contain multiple catalyst beds and can receive one or more quench hydrogen streams between the beds (not shown).

First reaction zone 372 operates under effective conditions for production of reaction effluent stream 374 which is passed to the fractionating zone 342 (optionally after one or more high pressure and low pressure separation stages to recover recycle hydrogen) generally to recover gas and liquid products and by-products, and separate a bottoms fraction.

Gas stream 344, typically containing $H_2$, $H_2S$, $NH_3$, and light hydrocarbons ($C_1$-$C_4$), is discharged and recovered and can be further processed. Effluent off-gases are passed to the olefins recovery train, the saturated gas plant as part of the other gases stream 156, and/or directly to a fuel gas system. Liquefied petroleum gas can be recovered and routed to the mixed feed steam cracking zone, the olefins recovery train and/or the saturated gas plant. One or more cracked product streams 346 are discharged via appropriate outlets of the fractionator and can be further processed and/or blended in downstream refinery operations to produce gasoline, kerosene and/or diesel fuel, or other petrochemical products. In certain embodiments, a diesel fraction 376 derived from the one or more cracked product streams 346 can be integrated with the feed to the second stage reactor 382. This integration adds to the flexibility of the configuration between production of diesel fuel or petrochemicals from the product streams 346.

In certain embodiments (not shown), fractionating zone 342 can operate as a flash vessel to separate heavy components at a suitable cut point, for example, a range corresponding to the upper temperature range of the desired gasoline, kerosene and/or diesel products for downstream operations. In certain embodiments, a suitable cut point is in the range of 350 to 450° C., 360 to 450° C., 370 to 450° C., 350 to 400° C., 360 to 400° C., 370 to 400° C., 350 to 380° C., or 360 to 380° C. The stream above that cut point is routed to the high olefinic fluid catalytic cracking zone 700 as described herein.

All or a portion of the fractionator bottoms stream 348 from the reaction effluent is passed to the second reaction zone 382 as stream 348a. In certain embodiments, all or a portion of the bottoms stream 348 is recycled to the second reaction zone 382 as stream 348a, the first reaction zone 372 as stream 348b, or both the first and second reaction zones 372 and 382. For instance, stream 348b which is recycled to zone 372 comprises 0 to 100 vol %, 0 to about 80 vol %, or 0 to about 50 vol % of stream 348, and stream 348a which is recycled to zone 382 comprises 0 to 100 vol %, 0 to about 80 vol %, or 0 to about 50 vol % of stream 348. In certain embodiments, in which the recycle is at or approaches 100 vol %, recycle of the unconverted oil increases the yield of products suitable as feed to the mixed feed steam cracking zone 230.

In certain embodiments, a portion of the fractionator bottoms from the reaction effluent is removed as bleed stream 368. Bleed stream 368 can be about 0-10 vol %, 1-10 vol %, 1-5 vol % or 1-3 vol % of the fractionator bottoms 348.

Second reaction zone 382 operates under conditions effective for production of the reaction effluent stream 386, which contains converted, partially converted and unconverted hydrocarbons. The second stage the reaction effluent stream 386 is passed to the fractionating zone 342, optionally through one or more gas separators to recovery recycle hydrogen and remove certain light gases For instance, a suitable two-stage hydrocracking zone 370 can include, but is not limited to, systems based on technology commercially available from Honeywell UOP, US; Chevron Lummus Global LLC (CLG), US; Axens, IFP Group Technologies, FR; or Shell Global Solutions, US.

The reactor arrangement in the two-stage with recycle hydrocracking zone 370 can contain one or more fixed-bed, ebullated-bed, slurry-bed, moving bed, continuous stirred tank (CSTR), or tubular reactors, which can be in parallel arrangement. Additional equipment, including exchangers, furnaces, feed pumps, quench pumps, and compressors to feed the reactor(s) and maintain proper operating conditions, are well known and are considered part of the two-stage hydrocracking zone 370. In addition, equipment, including pumps, compressors, high temperature separation vessels, low temperature separation vessels and the like to separate reaction products and provide hydrogen recycle within the two-stage hydrocracking zone 370, are well known and are considered part of the two-stage hydrocracking zone 370.

In certain embodiments, operating conditions for the first stage reactor(s) in hydrocracking zone 370 using a two-stage with recycle configuration operating in a full conversion mode of operation include:

a reactor inlet temperature (° C.) in the range of from about 340-502, 340-460, 340-440, 372-502, 372-460, 372-440, 394-502, 394-460, 394-440 or 412-420;

a reactor outlet temperature (° C.) in the range of from about 350-516, 350-471, 350-450, 382-516, 382-471, 382-450, 400-516, 400-471, 400-450 or 422-430;

a start of run (SOR) reaction temperature, as a weighted average bed temperature (WABT), in the range of from about 310-475, 310-435, 310-415, 350-475, 350-435, 350-415, 370-475, 370-435, 370-415 or 390-397;

an end of run (EOR) reaction temperature, as a WABT, in the range of from about 338-516, 338-471, 338-450, 382-516, 382-471, 382-450, 400-516, 400-471, 400-450 or 422-430;

a reaction inlet pressure (barg) in the range of from about 100-180, 100-160, 100-141, 121-180, 121-160, 121-141, 128-180, 128-160, 128-141 or 131-180;

a reaction outlet pressure (barg) in the range of from about 90-170, 90-137, 90-130, 112-170, 112-137, 112-130, 118-150, 118-137 or 118-170;

a hydrogen partial pressure (barg) (outlet) in the range of from about 90-137, 90-106, 90-120, 100-137, 100-106, or 100-120;

a hydrogen treat gas feed rate (SLt/Lt) up to about 1050, 940, 898 or 876, in certain embodiments from about 769-940, 769-898, 769-876, 812-940, 812-898, 812-876, 834-940, 834-898, or 834-876;

a hydrogen quench gas feed rate (SLt/Lt) up to about 1100, 980, 935 or 913, in certain embodiments from about 801-980, 801-935, 801-913, 846-980, 846-935, 846-913, 868-980, 868-935, or 868-913;

make-up hydrogen rate (SLt/Lt) up to about 564, 512, 490 or 468, in certain embodiments from about 378-512, 378-490, 378-468, 401-512, 401-490, 401-468, 423-512, 423-490, or 423-468; and liquid hourly space velocity values (h$^{-1}$), on a fresh feed basis relative to the hydrocracking catalysts, are in the range of from about 0.1-10.0, 0.1-5.0, 0.1-2.0, 0.3-10.0, 0.3-5.0, 0.3-2.0, 0.4-10.0, 0.4-5.0, 0.4-2.0 or 0.5-1.5.

In certain embodiments, operating conditions for the second stage reactor(s) in hydrocracking zone 370 using a two-stage with recycle configuration operating in a full conversion mode of operation include:

In certain embodiments, operating conditions for the reactor(s) in the first stage reaction zone of the two-stage hydrocracking zone 370 include:

a reactor inlet temperature (° C.) in the range of from about 340-502, 340-460, 340-440, 372-502, 372-460, 372-440, 394-502, 394-460, 394-440 or 412-420;

a reactor outlet temperature (° C.) in the range of from about 350-516, 350-471, 350-450, 382-516, 382-471, 382-450, 400-516, 400-471, 400-450 or 422-430;

a start of run (SOR) reaction temperature, as a weighted average bed temperature (WABT), in the range of from about 310-475, 310-435, 310-415, 350-475, 350-435, 350-415, 370-475, 370-435, 370-415 or 390-397;

an end of run (EOR) reaction temperature, as a WABT, in the range of from about 338-516, 338-471, 338-450, 382-516, 382-471, 382-450, 400-516, 400-471, 400-450 or 422-430;

a reaction inlet pressure (barg) in the range of from about 80-145, 80-100, 80-131, 80-120, 120-145, 100-145, or 130-145;

a reaction outlet pressure (barg) in the range of from about 75-137, 75-130, 90-130, 100-137, 100-122, or 112-137;

a hydrogen partial pressure (barg) (outlet) in the range of from about 90-145, 90-106, 90-120, 100-145, 100-106, or 100-120;

a hydrogen treat gas feed rate (SLt/Lt) up to about 910, 823, 785 or 767, in certain embodiments from about 673-823, 673-785, 673-767, 711-823, 711-785, 711-767, 729-823, 729-785, or 729-767;

a hydrogen quench gas feed rate (SLt/Lt) up to about 980, 882, 842 or 822, in certain embodiments from about 721-882, 721-842, 721-822, 761-882, 761-842, 761-822, 781-882, 781-842, or 781-822;

make-up hydrogen rate (SLt/Lt) up to about 451, 410, 392 or 374, in certain embodiments from about 303-410, 303-392, 303-374, 321-410, 321-392, 321-374, 338-410, 338-392, or 338-374; and liquid hourly space velocity values (h$^{-1}$), on a fresh feed basis relative to the hydrocracking catalysts, are in the range of from about 0.1-10.0, 0.1-5.0, 0.1-2.0, 0.3-10.0, 0.3-5.0, 1.0-5.0, 2.0-4.0 or 1.0-3.0.

Under the above conditions and catalyst selections, exemplary products from the hydrocracking zone 370 operating as a two-stage hydrocracker (with recycle) in a full conversion mode include 78-99, 78-90, 78-85, 80-90 or 80-99 wt % of effluent (relative to the feed to the hydrocracking zone 370) boiling at or below the atmospheric residue end boiling point, such as 370° C., including LPG, kerosene, naphtha, and atmospheric gas oil range components. The remaining bottoms fraction is the unconverted oil fraction, all or a portion of which can be effectively integrated as feed to the high olefinic fluid catalytic cracking zone 700 as described herein.

In certain embodiments, 0-100 wt % of the vacuum residue stream 168 can be processed in a residue treatment center 800 (shown in dashed lines as an optional embodiment). In additional embodiments, 0-100 wt % of the pyrolysis oil from the steam cracker complex can be routed to the residue treatment center 800. The residue treatment center 800 can include, but is not limited to, one or more of: a catalytic hydrogen addition process, such as a residue hydrocracking system; a thermal coking process, such as a delayed coker; and/or a solvent deasphalting process. In certain embodiments, the residue treatment center 800 produces one or more of a distillate fraction 808, a heavy fraction 806, and/or a bottoms fraction 804. The distillate fraction 808 can include, for instance, one or more middle distillate streams boiling in the temperature range including and below atmospheric gas oil range fractions (for instance in the temperature range of 36-370° C.), or including and below medium atmospheric gas oil range fractions. Note that when the residue treatment center 800 is solvent deasphalting, a distillate fraction 808 is not produced. Portions of the distillate fraction 808 can be used as feed to the mixed feed steam cracking zone 230, feed to one or more of the integrated hydroprocessing zones, and/or used for production of fuel components. All or a portion of the heavy fraction 806 can include, for instance, one or more streams of treated heavy range hydrocarbons boiling above the atmospheric gas oil range (for instance 370° C.), or above the medium atmospheric gas oil range; or deasphalted oil in a solvent deasphalting unit. Portions of the heavy fraction 806 can be used as feed to the gas oil steam cracking zone 250, feed to one or more of the integrated hydroprocessing zones, recovered as unconverted oil product, used for lube oil production in a base oil production zone, and/or incorporated in a fuel oil pool. The bottoms fraction 804 can include, for instance, pitch in a residue hydrocracking system, petroleum coke in a delayed coker, or asphalt in a solvent deasphalting unit).

Embodiments of systems and processes incorporating certain vacuum residue hydroprocessing zones are disclosed in U.S. patent application Ser. No 15/817,133 filed on Nov. 17, 2017, entitled "Process and System for Conversion of Crude Oil to Petrochemicals and Fuel Products Integrating Vacuum Residue Hydroprocessing," and U.S. patent application Ser. No 15/817,136 filed on Nov. 17, 2017, entitled "Process and System for Conversion of Crude Oil to Petrochemicals and Fuel Products Integrating Vacuum Residue Conditioning and Base Oil Production," which are commonly owned and are incorporated by reference herein in their entireties. Embodiments of systems and processes incorporating solvent deasphalting are disclosed in U.S. patent application Ser. No 15/817,140 filed on Nov. 17, 2017, entitled "Process and System for Conversion of Crude Oil to Petrochemicals and Fuel Products Integrating Solvent Deasphalting of Vacuum Residue," which is commonly owned and is incorporated by reference herein in its entirety. Embodiments of systems and processes incorporating thermal coking are disclosed in U.S. patent application Ser. No 15/817,143 filed on Nov. 17, 2017, entitled "Process and System for Conversion of Crude Oil to Petrochemicals and Fuel Products Integrating Delayed Coking of Vacuum Residue," which is commonly owned and is incorporated by reference herein in its entirety.

The hydrotreated gas oil fraction 304 is routed to the high olefinic fluid catalytic cracking zone 700. In certain embodiments, as shown in dashed lines, the fourth middle distillate stream 130 is also routed the high olefinic fluid catalytic cracking zone 700, bypassing the vacuum gas oil hydrotreating zone 300. In certain embodiments, as shown in dashed lines, the fourth middle distillate stream 130 is subjected to hydrotreating prior to passage to the high olefinic fluid catalytic cracking zone 700, for instance with the other feeds to the vacuum gas oil hydrotreating zone 300.

Products include fuel gas and LPG that are passed to an unsaturated gas plant 702, fluid catalytic cracking naphtha 706, which can be routed to a naphtha hydrotreating zone 670 as shown in FIG. 21; a light cycle oil stream 708, all or a portion of which is passed to the diesel hydrotreating zone 180, and a slurry oil or heavy cycle oil stream 710 that can be routed to a fuel oil pool or used as feedstock for production of carbon black. In certain embodiments, all or a portion of fluid catalytic cracking naphtha 706 can be routed to the aromatics extraction zone 620 without hydrotreating. In certain embodiments, 0-100 wt % 712 of the light cycle oil stream 708 is routed to a fuel oil pool The unsaturated gas plant 702 and a high olefinic fluid catalytic cracking recovery section (not shown) are operated to recover a C2− stream 714 and a C3+ stream that are passed to an olefins recovery train 270. In certain embodiments high olefinic fluid catalytic cracking light ends are selectively treated for removal of contaminants including oxygen, nitrous oxides, nitriles, acetylene, methyl acetylene, butadiene, arsine, phosphine, stibine and mercury, while preserving ethylene content. In certain embodiments treatment of the C2− off-gas stream includes use of a multifunctional catalyst as is known in the operation of unsaturated gas plants before being passed to the olefins recovery train 270. Furthermore, a C3+ stream 716, generally containing C3s and C4s, is recovered from the high olefinic fluid catalytic cracking recovery section. In certain embodiments, this stream is treated in a mercaptan oxidation unit, as is known in the operation of unsaturated gas plants, before routing to the to the olefins recovery train 270 or the steam cracking zone 230. In certain embodiments, the C3+ stream 716 stream is sent to a splitter, which can be integrated with or separate from the olefins recovery train 270, to recover olefins, and the remaining LPGs are routed to the mixed feed steam cracking zone 230. All, a substantial portion, a significant portion or a major portion of the C2− stream 714 and the C3+ stream 716 are routed through the unsaturated gas plant. The remainder, if any, can be routed to the mixed feed steam cracking zone 230 and/or the olefins recovery train 270.

In certain embodiments, the vacuum gas oil hydrotreating zone 300 can be bypassed and the high olefinic fluid catalytic cracking and associated regenerator are operated to treat the products from the unit, including flue gases produced in the catalyst regenerator, for control of sulfur. In other embodiments, the vacuum gas oil hydrotreating zone 300 is utilized, as treating the VGO reduces catalyst consumption in the high olefinic fluid catalytic cracking and enhances yield. In embodiments in which the vacuum gas oil hydrotreating zone 300 is utilized, flue gas desulfurization of flue gases produced in the catalyst regenerator is also provided.

As shown in FIGS. 12, 13 and 21, a portion of the cycle oil product from the high olefinic fluid catalytic cracking, cycle oil 708, is passed to the diesel hydrotreating zone 180, and a portion of the cycle oil product from the high olefinic fluid catalytic cracking, cycle oil 712, is diverted, for instance, for inclusion in a fuel oil pool. A quantity (wt %) of 0-5, 0-10, 0-15, or 0-20 of cycle oil stream 708 is passed to the diesel hydrotreating zone 180 and the remainder passed to a fuel oil pool. Slurry oil 710 is also recovered from the high olefinic fluid catalytic cracking zone 700. This heavy product is an effective feedstock for carbon black production, or can be included in a fuel oil pool.

There are many commercially available systems for maximizing the propylene production utilizing a fluid catalytic cracking unit. A suitable high olefinic fluid catalytic cracking zone 700 can include, but is not limited to, systems based on technology commercially available from Axens, IFP Group Technologies, FR; Honeywell UOP, US; CN Petroleum & Chemical Corporation (Sinopec), CN; KBR, Inc, US; or Chicago Bridge & Iron Company N.V. (CB&I), NL.

The high olefinic fluid catalytic cracking zone 700 can have one or more risers/reactors, a disengager/stripper and one or more regenerators. If plural reactors are implemented, propylene yield and selectivity can be maximized.

Figure 22:
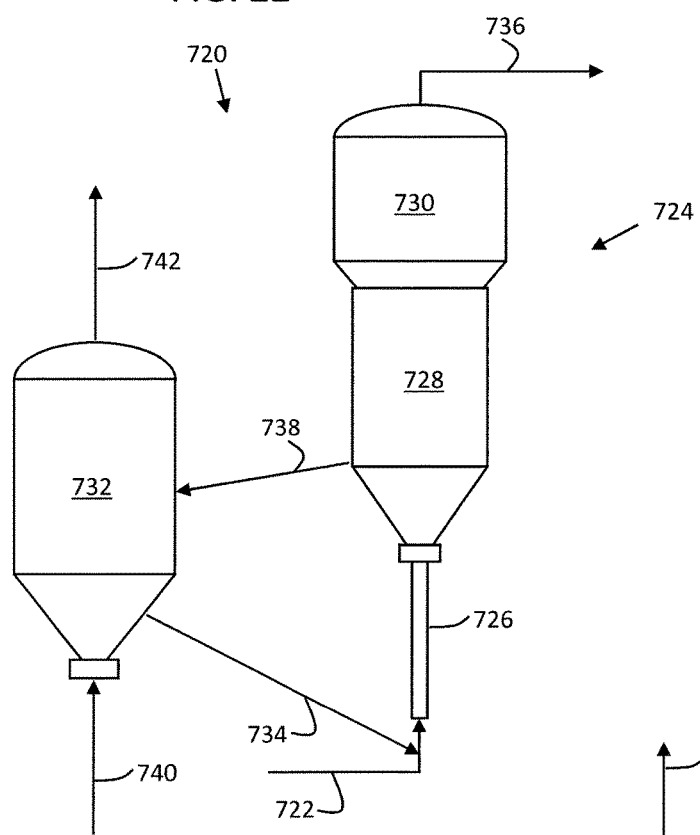
FIGS. 22 and 23 depict general operations of types of fluid catalytic cracking operations.

In certain embodiments, a fluid catalytic cracking unit configured with a riser reactor is provided that operates under conditions that promote formation of light olefins, particularly propylene, and that minimize light olefin-consuming reactions including hydrogen-transfer reactions. FIG. 22 is a simplified schematic illustration of a riser fluid catalytic cracking unit. A fluid catalytic cracking unit 720 includes a riser reactor. Fluid catalytic cracking unit 720 includes a reactor/separator 724 having a riser portion 726, a reaction zone 728 and a separation zone 730. Fluid catalytic cracking unit 720 also includes a regeneration vessel 732 for regenerating spent catalyst. A charge 722 is introduced to the reaction zone, in certain embodiments accompanied by steam or other suitable gas for atomization of the feed (not shown). The charge 722, in the integrated process herein hydrotreated gas oil, optionally in combination with atmospheric gas oil such as heavy atmospheric gas oil, is admixed and intimately contacted with an effective quantity of heated fresh or regenerated solid cracking catalyst particles which are conveyed via a conduit 734 from regeneration vessel 732. The feed mixture and the cracking catalyst are contacted under conditions to form a suspension that is introduced into the riser 726. In a continuous process, the mixture of cracking catalyst and hydrocarbon feedstock proceed upward through the riser 726 into reaction zone 728. In the riser 726 and reaction zone 728, the hot cracking catalyst particles catalytically crack relatively large hydrocarbon molecules by carbon-carbon bond cleavage.

During the reaction, as is conventional in fluid catalytic cracking operations, the cracking catalysts become coked and hence access to the active catalytic sites is limited or nonexistent. Reaction products are separated from the coked catalyst using any suitable configuration known in fluid catalytic cracking units, generally referred to as the separation zone 730 in a fluid catalytic cracking unit 720, for instance, located at the top of the reactor 724 above the reaction zone 728. The separation zone can include any suitable apparatus known to those of ordinary skill in the art such as, for example, cyclones. The reaction product is withdrawn through conduit 736. Catalyst particles containing coke deposits from fluid cracking of the hydrocarbon feedstock pass through a conduit 738 to regeneration zone 732.

In regeneration zone 732, the coked catalyst comes into contact with a stream of oxygen-containing gas, such as pure oxygen or air, which enters regeneration zone 732 via a conduit 740. The regeneration zone 732 is operated in a configuration and under conditions that are known in typical fluid catalytic cracking operations. For instance, regeneration zone 732 can operate as a fluidized bed to produce regeneration off-gas comprising combustion products which is discharged through a conduit 742. The hot regenerated catalyst is transferred from regeneration zone 732 through conduit 734 to the bottom portion of the riser 726 for admixture with the hydrocarbon feedstock and noted above.

In one embodiment, a suitable fluid catalytic cracking unit 720 can be similar to that described in U.S. Pat. Nos. 7,312,370, 6,538,169, and 5,326,465, the disclosures of which are incorporated herein by reference in their entireties. In general, the operating conditions for the reactor of a suitable riser fluid catalytic cracking unit 720 include:

a reaction temperature (° C.) of from about 480-650, 480-620, 480-600, 500-650, 500-620, or 500-600;

a reaction pressure (barg) of from about 1-20, 1-10, or 1-3;

a contact time (in the reactor, seconds) of from about 0.5-10, 0.5-5, 0.5-2, 1-10, 1-5, or 1-2; and a catalyst-to-feed ratio of about 1:1 to 15:1, 1:1 to 10:1, 1:1 to 20:1, 8:1 to 20:1, 8:1 to 15:1, or 8:1 to 10:1.

Figure 23:
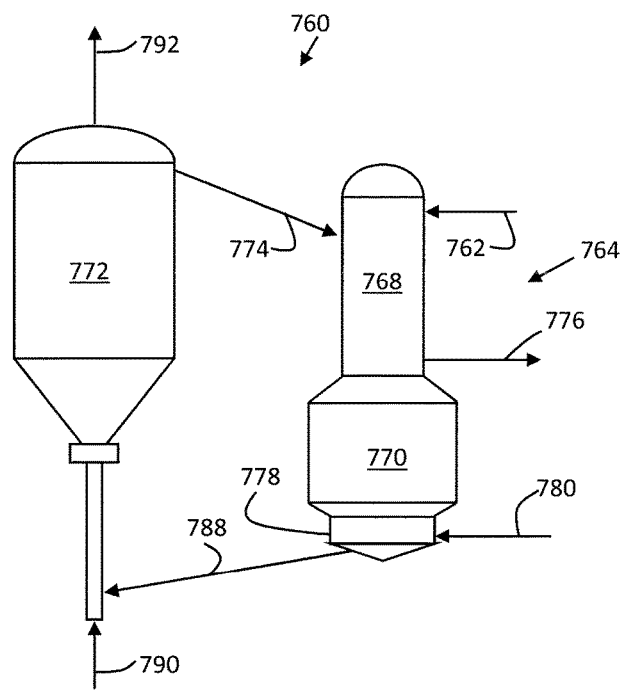

In certain embodiments, a fluid catalytic cracking unit configured with a downflow reactor is provided that operates under conditions that promote formation of light olefins, particularly propylene, and that minimize light olefin-consuming reactions including hydrogen-transfer reactions. FIG. 23 is a simplified schematic illustration of a downflow fluid catalytic cracking unit. A fluid catalytic cracking unit 760 includes a reactor/separator 764 having a reaction zone 768 and a separation zone 770. Fluid catalytic cracking unit 760 also includes a regeneration zone 772 for regenerating spent catalyst. In particular, a charge 762 is introduced to the reaction zone, in certain embodiments accompanied by steam or other suitable gas for atomization of the feed (not shown). An effective quantity of heated fresh or hot regenerated solid cracking catalyst particles from regeneration zone 772 is conveyed to the top of reaction zone 768 also transferred, for instance, through a downwardly directed conduit or pipe 774, commonly referred to as a transfer line or standpipe, to a withdrawal well or hopper (not shown) at the top of reaction zone 768. Hot catalyst flow is typically allowed to stabilize in order to be uniformly directed into the mix zone or feed injection portion of reaction zone 768. The charge 762 is injected into a mixing zone through feed injection nozzles typically situated proximate to the point of introduction of the regenerated catalyst into reaction zone 768. These multiple injection nozzles result in the thorough and uniform mixing of the hot catalyst and the charge 762, in the integrated process herein hydrotreated gas oil, optionally in combination with atmospheric gas oil such as heavy atmospheric gas oil. Once the charge contacts the hot catalyst, cracking reactions occur.

The reaction vapor of hydrocarbon cracked products, unreacted feed and catalyst mixture quickly flows through the remainder of reaction zone 768 and into the rapid separation zone 770 at the bottom portion of reactor/separator 764. Cracked and uncracked hydrocarbons are directed through a conduit or pipe 776 to a conventional product recovery section known in the art to yield as fluid catalytic cracking products light olefins, gasoline and cycle oil, with a maximized propylene yield. If necessary for temperature control, a quench injection can be provided near the bottom of reaction zone 768 immediately before the separation zone 770. This quench injection quickly reduces or stops the cracking reactions and can be utilized for controlling cracking severity to achieve the product slate.

The reaction temperature, i.e., the outlet temperature of the downflow reactor, can be controlled by opening and closing a catalyst slide valve (not shown) that controls the flow of hot regenerated catalyst from regeneration zone 772 into the top of reaction zone 768. The heat required for the endothermic cracking reaction is supplied by the regenerated catalyst. By changing the flow rate of the hot regenerated catalyst, the operating severity or cracking conditions can be controlled to produce the desired product slate. A stripper 778 is also provided for separating oil from the catalyst, which is transferred to regeneration zone 772. The catalyst from separation zone 770 flows to the lower section of the stripper 778 that includes a catalyst stripping section into which a suitable stripping gas, such as steam, is introduced through streamline 780. The stripping section is typically provided with several baffles or structured packing (not shown) over which the downwardly flowing catalyst 788 passes counter-currently to the flowing stripping gas. The upwardly flowing stripping gas, which is typically steam, is used to "strip" or remove any additional hydrocarbons that remain in the catalyst pores or between catalyst particles. The stripped and spent catalyst is transported by lift forces from the combustion air stream 790 through a lift riser of the regeneration zone 770. This spent catalyst, which can also be contacted with additional combustion air, undergoes controlled combustion of any accumulated coke. Flue gases are removed from the regenerator via conduit 792. In the regenerator, the heat produced from the combustion of the by-product coke is transferred to the catalyst raising the temperature required to provide heat for the endothermic cracking reaction in the reaction zone 768. According to the process herein, since the light solvent feedstock is combined with the heavy feedstock as the feed 762, the solvent to oil ratio in the initial solvent deasphalting/demetalizing process is selected so as to provide sufficient coking of the catalyst to provide the heat balance during regeneration.

In one embodiment, a suitable fluid catalytic cracking unit 760 with a downflow reactor that can be employed in the process described herein can be similar to those described in U.S. Pat. No. 6,656,346, and US Patent Publication Number 2002/0195373, the disclosures of which are incorporated herein by reference in their entireties. Important properties of downflow reactors include introduction of feed at the top of the reactor with downward flow, shorter residence time as compared to riser reactors, and high catalyst-to-oil ratio, for instance, in the range of about 20:1 to about 30:1. In general, the operating conditions for the reactor of a suitable propylene production downflow fluid catalytic cracking unit include a reaction temperature (° C.) of from about 550-650, 550-630, 550-620, 580-650, 580-630, 580-620, 590-650, 590-630, 590-620;

a reaction pressure (barg) of from about 1-20, 1-10, or 1-3;

a contact time (in the reactor, seconds) of from about 0.1-30, 0.1-10, 0.1-0.7, 0.2-30, 0.2-10, or 0.2-0.7; and a catalyst-to-feed ratio of about 1:1 to 40:1, 1:1 to 30:1, 10:1 to 30:1, or 10:1 to 30:1.

The catalyst used in the process described herein can be conventionally known or future developed catalysts used in fluid catalytic cracking processes, such as zeolites, silica-alumina, carbon monoxide burning promoter additives, bottoms cracking additives, light olefin-producing additives and any other catalyst additives routinely used in the fluid catalytic cracking process. In certain embodiments, suitable cracking zeolites in the fluid catalytic cracking process include zeolites Y, REY, USY, and RE-USY. For enhanced naphtha cracking potential, a preferred shaped selective catalyst additive can be employed, such as those used in fluid catalytic cracking processes to produce light olefins and increase fluid catalytic cracking gasoline octane is ZSM-5 zeolite crystal or other pentasil type catalyst structure. This ZSM-5 additive can be mixed with the cracking catalyst zeolites and matrix structures in conventional fluid catalytic cracking catalyst and is particularly suitable to maximize and optimize the cracking of the crude oil fractions in the downflow reaction zones.

Fluid catalytic cracking naphtha 706 is also recovered from the high olefinic fluid catalytic cracking zone 700. In certain embodiments, as depicted for instance in FIGS. 12, 13 and 21, fluid catalytic cracking naphtha 706 is further treated in the naphtha hydrotreating zone 670 in the presence of an effective amount of hydrogen obtained from recycle within the naphtha hydrotreating zone 670 and make-up hydrogen 674. Effluent fuel gas is recovered and, for instance, passed to a fuel gas system. In certain embodiments, all or a portion of the make-up hydrogen 674 is derived from the steam cracker hydrogen stream 210 from the olefins recovery train 270.

The cracked naphtha hydrotreating zone 670 operates under conditions effective to ensure removal of substantially all nitrogen, since nitrogen is a limiting contaminant in the aromatics extraction and subsequent processes. Due to the high temperature conditions effective for nitrogen removal, saturation of aromatics occurs, for instance, in the range of about 15% saturation, ahead of recovery. Effluents from the cracked naphtha hydrotreating zone 670 are a hydrotreated fluid catalytic cracking naphtha stream 672, and fuel gas.

A suitable cracked naphtha hydrotreating zone 670 can include, but is not limited to, systems based on technology commercially available from Honeywell UOP, US; Chevron Lummus Global LLC (CLG), US; or Axens, IFP Group Technologies, FR.

The effluent from the cracked naphtha hydrotreating reactor generally contain C5-C9+ hydrocarbons. In certain embodiments, C5-C9+ hydrocarbons are passed to the aromatics extraction zone 620, and the aromatics extraction zone 620 includes a depentanizing step to remove C5s. In other embodiments and as shown for instance in FIGS. 12 and 13, cracked naphtha hydrotreating zone 670 includes a depentanizing step to remove C5s, which are recycled as stream 676 to the mixed feed steam cracking zone 230. The hydrotreated fluid catalytic cracking naphtha stream 672, generally containing C6-C9+ hydrocarbons, is passed to the aromatics extraction zone 620.

The fluid catalytic cracking naphtha hydrotreating zone 670 can contain one or more fixed-bed, ebullated-bed, slurry-bed, moving bed, continuous stirred tank (CSTR) or tubular reactors, in series and/or parallel arrangement. Additional equipment, including exchangers, furnaces, feed pumps, quench pumps, and compressors to feed the reactor (s) and maintain proper operating conditions, are well known and are considered part of the fluid catalytic cracking naphtha hydrotreating zone 670. In addition, equipment, including pumps, compressors, high temperature separation vessels, low temperature separation vessels and the like to separate reaction products and provide hydrogen recycle within the fluid catalytic cracking naphtha hydrotreating zone 670, are well known and are considered part of the fluid catalytic cracking naphtha hydrotreating zone 670.

The fluid catalytic cracking naphtha hydrotreating zone 670 is operated under conditions effective to treat fluid catalytic cracking naphtha to produce hydrotreated naphtha 672 that can be used as additional feed to the aromatics extraction zone 620 for recovery of BTX streams. In certain embodiments hydrotreated naphtha 672 can be used for fuel production.

In certain embodiments, the cracked naphtha hydrotreating zone 670 operating conditions include:

a reactor inlet temperature (° C.) in the range of from about 293-450, 293-410, 293-391, 332-450, 332-410, 332-391, 352-450, 352-410, 352-391 or 368-374;

a reactor outlet temperature (° C.) in the range of from about 316-482, 316-441, 316-420, 357-482, 357-441, 357-420, 378-482, 378-441, 378-420 or 396-404;

a start of run (SOR) reaction temperature (° C.), as a weighted average bed temperature (WABT), in the range of from about 284-436, 284-398, 284-379, 322-436, 322-398, 322-379, 341-436, 341-398, 341-379 or 357-363;

an end of run (EOR) reaction temperature (° C.), as a WABT, in the range of from about 316-482, 316-441, 316-420, 357-482, 357-441, 357-420, 378-482, 378-441, 378-420 or 396-404;

a reaction inlet pressure (barg) in the range of from about 44-66, 44-60, 44-58, 49-66, 49-60, 49-58, 52-66, 52-60, 52-58 or 53-56;

a reaction outlet pressure (barg) in the range of from about 39-58, 39-53, 39-51, 43-58, 43-53, 43-51, 46-58, 46-53 or 46-51;

a hydrogen partial pressure (barg) (outlet) in the range of from about 22-33, 22-30, 22-29, 25-33, 25-30, 25-29, 26-33, 26-30 or 26-29;

a hydrogen treat gas feed rate (SLt/Lt) up to about 640, 620, 570 or 542, in certain embodiments from about 413-620, 413-570, 413-542, 465-620, 465-570, 465-542, 491-620, 491-570 or 491-542;

a hydrogen quench gas feed rate (SLt/Lt) up to about 95, 85, 78 or 75, in certain embodiments from about 57-85, 57-78, 57-75, 64-85, 64-78, 64-75, 68-85, 68-78 or 68-75; and a make-up hydrogen feed rate (SLt/Lt) up to about 120, 110 or 102, in certain embodiments from about 78-120, 78-110, 78-102, 87-120, 87-110, 87-102, 92-120, 92-110, 92-102 or 95-100.

An effective quantity of hydrotreating catalyst is provided in the fluid catalytic cracking naphtha hydrotreating zone 670, including those possessing hydrotreating functionality and which generally contain one or more active metal component of metals or metal compounds (oxides or sulfides) selected from the Periodic Table of the Elements IUPAC Groups 6-10. In certain embodiments, the active metal component is one or more of Co, Ni, W and Mo. The active metal component is typically deposited or otherwise incorporated on a support, such as amorphous alumina, amorphous silica alumina, zeolites, or combinations thereof. In certain embodiments, the catalyst used in the fluid catalytic cracking naphtha hydrotreating zone 670 includes one or more catalyst selected from Co/Mo, Ni/Mo, Ni/W, and Co/Ni/Mo. Combinations of one or more of Co/Mo, Ni/Mo, Ni/W and Co/Ni/Mo, can also be used. The combinations can be composed of different particles containing a single active metal species, or particles containing multiple active species. In certain embodiments, Co/Mo hydrodesulfurization catalyst is suitable. Effective liquid hourly space velocity values ($h^{-1}$), on a fresh feed basis relative to the hydrotreating catalysts, are in the range of from about 0.1-10.0, 0.1-5.0, 0.1-2.0, 0.3-10.0, 0.3-5.0, 0.3-2.0, 0.5-10.0, 0.5-5.0, 0.5-2.0 or 0.8-1.2. Suitable hydrotreating catalysts used in the fluid catalytic cracking naphtha hydrotreating zone 670 have an expected lifetime in the range of about 28-44, 34-44, 28-38 or 34-38 months.

The mixed feed steam cracking zone 230, which operates as high severity or low severity thermal cracking process, generally converts LPG, naphtha and heavier hydrocarbons primarily into a mixed product stream 220 containing mixed C1-C4 paraffins and olefins. In certain embodiments, the mixed feed steam cracking zone 230 processes straight-run liquids from the crude unit, propane (from outside battery limits and/or recycled) and various recycle streams from chemical production and recovery areas within the integrated process and system. A suitable mixed feed steam cracking zone 230 can include, but is not limited to, systems based on technology commercially available from Linde AG, DE; TechnipFMC plc, UK; Chicago Bridge & Iron Company N.V. (CB&I), NL; or KBR, Inc, US.

Plural feeds to the mixed feed steam cracking zone 230 include: light ends 152, light naphtha 138 and heavy naphtha 140 (or a full range straight run naphtha 136 as shown in other embodiments) from the crude complex 100; a LPG stream 634 from a transalkylation zone 630; a C3+ stream 716 recovered from the high olefinic fluid catalytic cracking zone 700; a recycle stream 282 from the methyl acetylene/propadiene (MAPD) saturation and propylene recovery zone 280, described below; C4 raffinate 524 from the 1-butene recovery zone 520 described below; C5s stream 676 from the fluid catalytic cracking naphtha hydrotreating ("FCCN HT") zone 670; C5s stream 606 from the py-gas hydrotreating zone 600; wild naphtha 184 from the diesel hydrotreating zone 180 described above (in certain embodiments via the crude complex); naphtha from the vacuum gas oil hydroprocessing zone described above (wild naphtha 326 or hydrotreated naphtha 306) described above (in certain embodiments via the crude complex); a raffinate stream 646 from the aromatics extraction zone 620; in certain embodiments a C5 cut derived from the pyrolysis gasoline described below; and optionally, propane stream 228 (from outside battery limits). In certain embodiments, the mixed feed steam cracking zone 230 can accept alternate feeds from other sources, for instance, other naphtha range feeds that may become available from outside of the battery limits.

The products from the mixed feed steam cracking zone 230 include a quenched cracked gas stream 220 containing mixed C1-C4 paraffins and olefins that is routed to the olefins recovery zone 270, a raw pyrolysis gasoline stream 212 that is routed to a py-gas hydrotreating zone 600 to provide feed 604 to the aromatics extraction zone 620, and a pyrolysis fuel oil stream 218.

The mixed feed steam cracking zone 230 operates under parameters effective to crack the feed into desired products including ethylene, propylene, butadiene, and mixed butenes. Pyrolysis gasoline and pyrolysis oil are also recovered. In certain embodiments, the steam cracking furnace(s) are operated at conditions effective to produce an effluent having a propylene-to-ethylene weight ratio of from about 0.3-0.8, 0.3-0.6, 0.4-0.8 or 0.4-0.6.

The mixed feed steam cracking zone 230 generally comprises one or more trains of furnaces. For instance, a typical arrangement includes reactors that can operate based on well-known steam pyrolysis methods, that is, charging the thermal cracking feed to a convection section in the presence of steam to raise the temperature of the feedstock, and passing the heated feed to the pyrolysis reactor containing furnace tubes for cracking. In the convection section, the mixture is heated to a predetermined temperature, for example, using one or more waste heat streams or other suitable heating arrangement.

The feed mixture is heated to a high temperature in a convection section and material with a boiling point below a predetermined temperature is vaporized. The heated mixture (in certain embodiments along with additional steam) is passed to the pyrolysis section operating at a further elevated temperature for short residence times, such as 1-2 seconds or less, effectuating pyrolysis to produce a mixed product stream. In certain embodiments separate convection and radiant sections are used for different incoming feeds to the mixed feed steam cracking zone 230 with conditions in each optimized for the particular feed.

In certain embodiments, steam cracking in the mixed feed steam cracking zone 230 is carried out using the following conditions: a temperature (° C.) in the convection section in the range of about 400-600, 400-550, 450-600 or 500-600; a pressure (barg) in the convection section in the range of about 4.3-4.8, 4.3-4.45, 4.3-4.6, 4.45-4.8, 4.45-4.6 or 4.6-4.8; a temperature (° C.) in the pyrolysis section in the range of about 700-950, 700-900, 700-850, 750-950, 750-900 or 750-850; a pressure (barg) in the pyrolysis section in the range of about 1.0-1.4, 1.0-1.25, 1.25-1.4, 1.0-1.15, 1.15-1.4 or 1.15-1.25; a steam-to-hydrocarbon ratio in the in the convection section in the range of about 0.3:1-2:1, 0.3:1-1.5:1, 0.5:1-2:1, 0.5:1-1.5:1, 0.7:1-2:1, 0.7:1-1.5:1, 1:1-2:1 or 1:1-1.5:1; and a residence time (seconds) in the pyrolysis section in the range of about 0.05-1.2, 0.05-1, 0.1-1.2, 0.1-1, 0.2-1.2, 0.2-1, 0.5-1.2 or 0.5-1.

In operation of the mixed feed steam cracking zone 230, effluent from the cracking furnaces is quenched, for instance, using transfer line exchangers, and quenched in a quench tower. The light products, quenched cracked gas stream 220, are routed to the olefins recovery zone 270. Heavier products are separated in a hot distillation section. A raw pyrolysis gasoline stream is recovered in the quench system. Pyrolysis oil 218 is separated at a primary fractionator tower before the quench tower.

In operation of one embodiment of the mixed feed steam cracking zone 230, the feedstocks are mixed with dilution steam to reduce hydrocarbon partial pressure and then are preheated. The preheated feeds are fed to empty tubular reactors mounted in the radiant sections of the cracking furnaces. The hydrocarbons undergo free-radical pyrolysis reactions to form light olefins ethylene and propylene, and other by-products. In certain embodiments, dedicated cracking furnaces are provided with cracking tube geometries optimized for each of the main feedstock types, including ethane, propane, and butanes/naphtha. Less valuable hydrocarbons, such as ethane, propane, C4 raffinate, and aromatics raffinate, produced within the integrated system and process, are recycled to extinction in the mixed feed steam cracking zone 230.

In certain embodiments, cracked gas from the furnaces is cooled in transfer line exchangers (quench coolers), for example, producing 1800 psig steam suitable as dilution steam. Quenched cracked gas enters a primary fractionator associated with the mixed feed steam cracker 230 that removes pyrolysis fuel oil bottoms from lighter components. The primary fractionator enables efficient recovery of pyrolysis fuel oil. Pyrolysis fuel oil is stripped with steam in a fuel oil stripper to control product vapor pressure, and cooled. In addition, secondary quench is carried out by direct injection of pyrolysis fuel oil as quench oil into liquid furnace effluents. The stripped and cooled pyrolysis fuel oil can be sent to a fuel oil pool or product storage. The primary fractionator overhead is sent to a quench water tower; condensed dilution steam for process water treating, and raw pyrolysis gasoline, are recovered. Quench water tower overhead is sent to the olefins recovery zone 270, particularly the first compression stage. Raw pyrolysis gasoline is sent to a gasoline stabilizer to remove any light ends and to control vapor pressure in downstream pyrolysis gasoline processing. A closed-loop dilution steam/process water system is enabled, in which dilution steam is generated using heat recovery from the primary fractionator quench pumparound loops. The primary fractionator enables efficient recovery of pyrolysis fuel oil due to energy integration and pyrolysis fuel oil content in the light fraction stream.

The mixed product stream 220 effluent from the mixed feed steam cracking zone 230 is routed to an olefins recovery zone 270. For instance, light products from the quenching step, C4−, H2 and H2S, are contained in the mixed product stream 220 that is routed to the olefins recovery zone 270. Products include: hydrogen 210 that is used for recycle and/or passed to users; fuel gas 208 that is passed to a fuel gas system; ethane 272 that is recycled to the mixed feed steam cracking zone 230; ethylene 202 that is recovered as product; a mixed C3 stream 286 that is passed to a methyl acetylene/propadiene saturation and propylene recovery zone 280; and a mixed C4 stream 206 that is passed to a butadiene extraction zone 500.

The olefins recovery zone 270 operates to produce on-specification light olefin (ethylene and propylene) products from the mixed product stream 220. For instance, cooled gas intermediate products from the steam cracker is fed to a cracked gas compressor, caustic wash zone, and one or more separation trains for separating products by distillation. In certain embodiments two trains are provided. The distillation train includes a cold distillation section, wherein lighter products such as methane, hydrogen, ethylene, and ethane are separated in a cryogenic distillation/separation operation. The mixed C2 stream from the steam cracker contains acetylenes that are hydrogenated to produce ethylene in an acetylene selective hydrogenation unit. This system can also include ethylene, propane and/or propylene refrigeration facilities to enable cryogenic distillation.

In one embodiment, the mixed product stream 220 effluent from the mixed feed steam cracking zone 230 is passed through three to five stages of compression. Acid gases are removed with caustic in a caustic wash tower. After an additional stage of compression and drying, light cracked gases are chilled and routed to a depropanizer. In certain embodiments light cracked gases are chilled with a cascaded two-level refrigeration system (propylene, mixed binary refrigerant) for cryogenic separation. A front-end depropanizer optimizes the chilling train and demethanizer loading. The depropanizer separates C3 and lighter cracked gases as an overhead stream, with C4s and heavier hydrocarbons as the bottoms stream. The depropanizer bottoms are routed to the debutanizer, which recovers a crude C4s stream 206 and any trace pyrolysis gasoline, which can be routed to the py-gas hydrotreating zone 600 (not shown).

The depropanizer overhead passes through a series of acetylene conversion reactors, and is then fed to the demethanizer chilling train, which separates a hydrogen-rich product via a hydrogen purification system, such as pressure swing adsorption. Front-end acetylene hydrogenation is implemented to optimize temperature control, minimize green oil formation and simplify ethylene product recovery by eliminating a C2 splitter pasteurization section that is otherwise typically included in product recovery. In addition, hydrogen purification via pressure swing adsorption eliminates the need for a methanation reactor that is otherwise typically included in product recovery.

The demethanizer recovers methane in the overhead for fuel gas, and C2 and heavier gases in the demethanizer bottoms are routed to the deethanizer. The deethanizer separates ethane and ethylene overhead which feeds a C2 splitter. The C2 splitter recovers ethylene product 202, in certain embodiments polymer-grade ethylene product, in the overhead. Ethane 272 from the C2 splitter bottoms is recycled to the mixed feed steam cracking zone 230. Deethanizer bottoms contain C3s from which propylene product 204, in certain embodiments polymer-grade propylene product, is recovered as the overhead of a C3 splitter, with propane 282 from the C3 splitter bottoms recycled to the mixed feed steam cracking zone 230.

A methyl acetylene/propadiene (MAPD) saturation and propylene recovery zone 280 is provided for selective hydrogenation to convert methyl acetylene/propadiene, and to recover propylene from a mixed C3 stream 286 from the olefins recovery zone 270. The mixed C3 286 from the olefins recovery zone 270 contains a sizeable quantity of propadiene and propylene. The methyl acetylene/propadiene saturation and propylene recovery zone 280 enables production of propylene 204, which can be polymer-grade propylene in certain embodiments.

The methyl acetylene/propadiene saturation and propylene recovery zone 280 receives hydrogen 284 and mixed C3 286 from the olefins recovery zone 270. Products from the methyl acetylene/propadiene saturation and propylene recovery zone 280 are propylene 204 which is recovered, and the recycle C3 stream 282 that is routed to the steam cracking zone 230. In certain embodiments, hydrogen 284 to saturate methyl acetylene and propadiene is derived from hydrogen 210 obtained from the olefins recovery zone 270.

A stream 206 containing a mixture of C4s, known as crude C4s, from the olefins recovery zone 270, is routed to a butadiene extraction zone 500 to recover a high purity 1,3-butadiene product 502 from the mixed crude C4s. In certain embodiments (not shown), a step of hydrogenation of the mixed C4 before the butadiene extraction zone 500 can be integrated to remove acetylenic compounds, for instance, with a suitable catalytic hydrogenation process using a fixed bed reactor. 1,3-butadiene 502 is recovered from the hydrogenated mixed C4 stream by extractive distillation using, for instance, n-methyl-pyrrolidone (NMP) or dimethylformamide (DMF) as solvent. The butadiene extraction zone 500 also produces a raffinate stream 504 containing butane/butene, which is passed to a methyl tertiary butyl ether zone 510.

In one embodiment, in operation of the butadiene extraction zone 500, the stream 206 is preheated and vaporized into a first extractive distillation column, for instance having two sections. NMP or DMF solvent separates the 1,3-butadiene from the other C4 components contained in stream 504. Rich solvent is flashed with vapor to a second extractive distillation column that produces a high purity 1,3 butadiene stream as an overhead product. Liquid solvent from the flash and the second distillation column bottoms are routed to a primary solvent recovery column. Bottoms liquid is circulated back to the extractor and overhead liquid is passed to a secondary solvent recovery or solvent polishing column. Vapor overhead from the recovery columns combines with recycle butadiene product into the bottom of the extractor to increase concentration of 1,3-butadiene. The 1,3-butadiene product 502 can be water washed to remove any trace solvent. In certain embodiments, the product purity (wt %) is 97-99.8, 97.5-99.7 or 98-99.6 of 1,3-butadiene and 94-99, 94.5-98.5, or 95-98 of the 1,3-butadiene content (wt %) of the feed is recovered. In addition to the solvent such as DMF, additive chemicals are blended with the solvent to enhance butadiene recovery. In addition, the extractive distillation column and primary solvent recovery columns are reboiled using high pressure steam (for instance, 600 psig) and circulating hot oil from the aromatics extraction zone 620 as heat exchange fluid.

A methyl tertiary butyl ether zone 510 is integrated to produce methyl tertiary butyl ether 514 and a second C4 raffinate 516 from the first C4 raffinate stream 504. In certain embodiments C4 Raffinate 1 504 is subjected to selective hydrogenation to selectively hydrogenate any remaining dienes and prior to reacting isobutenes with methanol to produce methyl tertiary butyl ether.

Purity specifications for recovery of a 1-butene product stream 522 necessitate that the level of isobutylene in the second C4 raffinate 516 be reduced. In general, the first C4 raffinate stream 504 containing mixed butanes and butenes, and including isobutylene, is passed to the methyl tertiary butyl ether zone 510. Methanol 512 is also added, which reacts with isobutylene and produces methyl tertiary butyl ether 514. For instance, methyl tertiary butyl ether product and methanol are separated in a series of fractionators, and routed to a second reaction stage. Methanol is removed with water wash and a final fractionation stage. Recovered methanol is recycled to the fixed bed downflow dehydrogenation reactors. In certain embodiments described below with respect to FIG. 24, additional isobutylene can be introduced to the methyl tertiary butyl ether zone 510, for instance, derived from a metathesis conversion unit.

In operation of one embodiment of the methyl tertiary butyl ether zone 510, the raffinate stream 504, contains 35-45%, 37-42.5%, 38-41% or 39-40% isobutylene by weight. This component is removed from the C4 raffinate 516 to attain requisite purity specifications, for instance, greater than or equal to 98 wt % for the 1-butene product stream 522 from the C4 distillation unit 520. Methanol 512, in certain embodiments high purity methanol having a purity level of greater than or equal to 98 wt % from outside battery limits, and the isobutylene contained in the raffinate stream 504 and in certain embodiments isobutylene 544 from metathesis (shown in dashed lines as an optional feed), react in a primary reactor. In certain embodiments the primary reactor is a fixed bed downflow dehydrogenation reactor and operates for isobutylene conversion in the range of about 70-95%, 75-95%, 85-95% or 90-95% on a weight basis. Effluent from the primary reactor is routed to a reaction column where reactions are completed. In certain embodiments, exothermic heat of the reaction column and the primary reactor can optionally be used to supplement the column reboiler along with provided steam. The reaction column bottoms contains methyl tertiary butyl ether, trace amounts, for instance, less than 2%, of unreacted methanol, and heavy products produced in the primary reactor and reaction column. Reaction column overhead contains unreacted methanol and non-reactive C4 raffinate. This stream is water washed to remove unreacted methanol and is passed to the 1-butene recovery zone 520 as the C4 raffinate 516. Recovered methanol is removed from the wash water in a methanol recovery column and recycled to the primary reactor.

The C4 raffinate stream 516 from the methyl tertiary butyl ether zone 510 is passed to the C4 distillation unit 520 for butene-1 recovery. In certain embodiments, upstream of the methyl tertiary butyl ether zone 510, or between the methyl tertiary butyl ether zone 510 and separation zone 520 for butene-1 recovery, a selective hydrogenation zone can also be included (not shown). For instance, in certain embodiments, raffinate from the methyl tertiary butyl ether zone 510 is selectively hydrogenated in a selective hydrogenation unit to produce butene-1. Other co-monomers and paraffins are also co-produced. The selective hydrogenation zone operates in the presence of an effective amount of hydrogen obtained from recycle within the selective hydrogenation zone and make-up hydrogen; in certain embodiments, all or a portion of the make-up hydrogen for the selective hydrogenation zone is derived from the steam cracker hydrogen stream 210 from the olefins recovery train 270. For instance, a suitable selective hydrogenation zone can include, but is not limited to, systems based on technology commercially available from Axens, IFP Group Technologies, FR; Haldor Topsoe A/S, DK; Clariant International Ltd, CH; Chicago Bridge & Iron Company N.V. (CB&I), NL; Honeywell UOP, US; or Shell Global Solutions, US.

For selective recovery of a 1-butene product stream 522 and a recycle stream 524 that is routed to the mixed feed steam cracking zone 230, and/or in certain embodiments described herein routed to a metathesis zone, one or more separation steps are used. For example, 1-butene can be recovered using two separation columns, where the first column recovers olefins from the paraffins and the second column separates 1-butene from the mixture including 2-butene, which is blended with the paraffins from the first column and recycled to the steam cracker as a recycle stream 524.

In certain embodiments, the C4 raffinate stream 516 from the methyl tertiary butyl ether zone 510 is passed to a first splitter, from which from isobutane, 1-butene, and n-butane are separated from heavier C4 components. Isobutane, 1-butene, and n-butane are recovered as overhead, condensed in an air cooler and sent to a second splitter. Bottoms from the first splitter, which contains primarily cis- and trans-2-butene can be added to the recycle stream 524, or in certain embodiments described herein passed to a metathesis unit. In certain arrangements, the first splitter overhead enters the mid-point of the second splitter. Isobutane product 526 can optionally be recovered in the overhead (shown in dashed lines), 1-butene product 522 is recovered as a sidecut, and n-butane is recovered as the bottoms stream. Bottoms from both splitters is recovered as all or a portion of the recycle stream 524.

The raw pyrolysis gasoline stream 212 from the steam cracker is treated and separated into treated naphtha and other fractions. In certain embodiments, all, a substantial portion or a significant portion of the pyrolysis gasoline 212 from the steam cracking zone 230 is passed to the py-gas hydrotreating zone 600. The raw pyrolysis gasoline stream 212 is processed in a py-gas hydrotreating zone 600 in the presence of an effective amount of hydrogen obtained from recycle within the obtained from recycle within and make-up hydrogen 602. Effluent fuel gas is recovered and, for instance, passed to a fuel gas system. In certain embodiments, all or a portion of the make-up hydrogen 602 is derived from the steam cracker hydrogen stream 210 from the olefins recovery train 270. For instance, a suitable py-gas hydrotreating zone 600 can include, but is not limited to, systems based on technology commercially available from Honeywell UOP, US; Chevron Lummus Global LLC (CLG), US; Axens, IFP Group Technologies, FR; Haldor Topsoe A/S, DK; or Chicago Bridge & Iron Company N.V. (CB&I), NL.

The py-gas hydrotreating zone 600 is operated under conditions, and utilizes catalyst(s), that can be varied over a relatively wide range. These conditions and catalyst(s) are selected for effective hydrogenation for saturation of certain olefin and diolefin compounds, and if necessary for hydrotreating to remove sulfur and/or nitrogen containing compounds. In certain embodiments, this is carried out in at least two catalytic stages, although other reactor configurations can be utilized. Accordingly, py-gas hydrotreating zone 600 subjects the pyrolysis gasoline stream 212 to hydrogenation to produce hydrotreated pyrolysis gasoline 604 effective as feed to the aromatics extraction zone 620. Effluent off-gases are recovered from the py-gas hydrotreating zone 600 and are passed to the olefins recovery train, the saturated gas plant as part of the other gases stream 156, and/or directly to a fuel gas system. Liquefied petroleum gas can be recovered from the py-gas hydrotreating zone 600 and routed to the mixed feed steam cracking zone, the olefins recovery train and/or the saturated gas plant.

In the py-gas hydrotreating zone 600, diolefins in the feed and olefins in the C6+ portion of the feed are saturated to produce a naphtha stream 604, a C5+ feed to the aromatics extraction zone. In certain embodiments, a depentanizing step associated with the py-gas hydrotreating zone 600 separates all or a portion of the C5s, for instance, as additional feed 606 to the mixed feed steam cracking zone 230 and/or as feed to a metathesis unit 530 (as shown, for instance, in FIG. 6, 8 or 24). In other embodiments, a depentanizing step associated with the aromatics extraction zone 620 separates all or a portion of the C5s from the hydrotreated naphtha stream 604, for instance, as additional feed to the mixed feed steam cracking zone 230 and/or as feed to a metathesis unit 530.

In certain embodiments, pyrolysis gasoline is processed in a first reaction stage for hydrogenation and stabilization. Diolefins are saturated selectively in the first reaction stage, and remaining olefins are saturated in the second reaction stage along with converting feed sulfur into hydrogen sulfide. The pyrolysis gasoline can be treated in a cold hydrotreating unit, therefore reducing the level of aromatics saturation.

In an example of an effective py-gas hydrotreating zone 600, raw pyrolysis gasoline is passed through a coalescer before entering a feed surge drum. The first stage reactor operates in mixed phase and selectively hydrogenates diolefins to mono-olefins and unsaturated aromatics to side-chain saturated aromatics. Pd-based catalyst materials are effective. Two parallel first-stage reactors can be used in certain embodiments to allow for regeneration in a continuous process without shutdown. In certain embodiments, the first-stage reactor contains three catalyst beds with cooled first stage separator liquid recycled as quench material between each bed. First-stage effluent is stabilized and separated in a column operating under slight vacuum to reduce temperature. In certain embodiments C5 from the C6+ is drawn, followed by a deoctanizer to remove C9+ and produce a C6-C8 heart naphtha cut. The column operates under slight vacuum to limit temperature. The first stage product is stripped to remove hydrogen, $H_2S$, and other light ends. In certain embodiments, the stripped first stage product is depentanized to remove cracked C5, for instance, as feed to a metathesis unit. A second stage reactor operates in vapor phase and removes sulfur and saturates olefins. The second stage product is stripped to remove hydrogen, $H_2S$, and other light ends. In certain embodiments, both reactors are multi-bed and use product recycle to control reactor temperature rise.

In certain embodiments, the first reaction stage of the py-gas hydrotreating zone 600 operating conditions include:

a reactor inlet temperature (° C.) in the range of from about 80-135, 80-125, 80-115, 95-135, 95-125, 95-115, 100-135, 100-125, 100-115 or 107-111;

a reactor outlet temperature (° C.) in the range of from about 145-230, 145-206, 145-200, 165-230, 165-206, 165-200, 175-230, 175-206, 175-200 or 184-188;

a start of run (SOR) reaction temperature (° C.), as a weighted average bed temperature (WABT), in the range of from about 75-125, 75-115, 75-110, 90-125, 90-115, 90-110, 95-125, 95-115, 95-110 or 99-104;

an end of run (EOR) reaction temperature (° C.), as a WABT, in the range of from about 124-195, 124-180, 124-170, 140-195, 140-180, 140-170, 150-195, 150-180, 150-170 or 158-163;

a reaction inlet pressure (barg) in the range of from about 25-40, 25-35, 25-33, 28-40, 28-35, 28-33, 30-40, 30-35 or 30-33;

a reaction outlet pressure (barg) in the range of from about 23-35, 23-33, 23-31, 25-35, 25-33, 25-31, 28-35, 28-33 or –28-31;

a hydrogen partial pressure (barg) (outlet) in the range of from about 15-25, 15-22, 15-21, 18-25, 18-22, 18-21, 19-25 or 19-22;

a hydrogen treat gas feed rate (SLt/Lt) up to about 180, 165 or 156, in certain embodiments from about 120-180, 120-165, 120-156, 134-180, 134-165, 134-156, 140-180, 140-165 or 140-156;

a liquid quench feed ratio (Lt quench/Lt feed) up to about 0.8, 0.7, 0.6 or 0.5, and in certain embodiments in the range of from about 0.35-0.6, 0.35-0.55, 0.35-0.5, 0.4-0.6, 0.4-0.55, 0.4-0.5, 0.45-0.6, 0.45-0.55 or 0.45-0.5; and a make-up hydrogen feed rate (SLt/Lt) up to about 60, 55, 47 or 45, in certain embodiments from about 34-55, 34-47, 34-45, 40-55, 40-47, 40-45, 42-55, 42-47 or 42-45.

In certain embodiments, the second reaction stage of the py-gas hydrotreating zone 600 operating conditions include:

a reactor inlet temperature (° C.) in the range of from about 225-350, 225-318, 225-303, 255-350, 255-318, 255-303, 270-350, 270-318, 270-303 or 285-291;

a reactor outlet temperature (° C.) in the range of from about 289-445, 289-405, 289-386, 328-445, 328-405, 328-386, 345-445, 345-405, 345-386 or 364-370;

a start of run (SOR) reaction temperature (° C.), as a weighted average bed temperature (WABT), in the range of from about 217-336, 217-306, 217-291, 245-336, 245-306, 245-291, 260-336, 260-306, 260-291 or 274-280;

an end of run (EOR) reaction temperature (° C.), as a WABT, in the range of from about 325-416, 325-380, 325-362, 305-416, 305-380, 305-362, 325-416, 325-380, 325-362 or 340-346;

a reaction inlet pressure (barg) in the range of from about 25-37, 25-34, 25-32, 28-37, 28-34, 28-32, 29-37, 29-34 or 29-32;

a reaction outlet pressure (barg) in the range of from about 23-35, 23-32, 23-30, 26-35, 26-32, 26-30, 28-35, 28-32 or 28-30;

a hydrogen partial pressure (barg) (outlet) in the range of from about 6-10, 6-9, 7-10 or 7-9;

a hydrogen treat gas feed rate (SLt/Lt) up to about 135, 126, 116 or 110, in certain embodiments from about 84-126, 84-116, 84-110, 95-126, 95-116, 95-110, 100-126, 100-116 or 100-110; and a make-up hydrogen feed rate (SLt/Lt) up to about 30, 27 or 24, in certain embodiments from about 18-30, 18-27, 18-24, 21-30, 21-27, 21-24, 22-30, 22-27 or 22-24.

An effective quantity of catalyst possessing selective hydrogenation functionality is provided, which generally contain one or more active metal component of metals or metal compounds (oxides or sulfides) selected from Co, Mo, Pt, Pd, Fe, or Ni. The active metal component is typically deposited or otherwise incorporated on a support, such as amorphous alumina, amorphous silica alumina, zeolites, or combinations thereof. Exemplary selective hydrogenation catalyst predominantly use Pd as the active metal component on alumina support, including those commercially available under the trade name Olemax® 600 and Olemax® 601. Effective liquid hourly space velocity values ($h^{-1}$), on a fresh feed basis relative to the first stage pyrolysis gasoline reactor catalyst, are in the range of from about 0.1-10.0, 0.1-5.0, 0.1-2.0, 0.3-10.0, 0.3-5.0, 0.3-2.0, 0.5-10.0, 0.5-5.0, 0.5-2.0 or 0.9 to 1.44. Suitable catalysts used in the first stage pyrolysis gasoline reactor have an expected lifetime in the range of about 18-30, 22-30, 18-26 or 22-26 months.

An effective quantity of second stage pyrolysis gasoline reactor catalyst is provided, including those having hydrogenation functionality and which generally contain one or more active metal component of metals or metal compounds (oxides or sulfides) selected from the Periodic Table of the Elements IUPAC Groups 6-10. In certain embodiments, the active metal component is one or more of Co, Ni, W and Mo. The active metal component is typically deposited or otherwise incorporated on a support, such as amorphous alumina, amorphous silica alumina, zeolites, or combinations thereof. In certain embodiments, the catalyst used in the first stage pyrolysis gasoline reactor includes one or more catalyst selected from Co/Mo, Ni/Mo, Ni/W, and Co/Ni/Mo. Combinations of one or more of Co/Mo, Ni/Mo, Ni/W and Co/Ni/Mo, can also be used. For example, a combination of catalyst particles commercially available under the trade names Olemax® 806 and Olemax® 807 can be used, with active metal components of Co and Ni/Mo. The combinations can be composed of different particles containing a single active metal species, or particles containing multiple active species. Effective liquid hourly space velocity values ($h^{-1}$), on a fresh feed basis relative to the first stage pyrolysis gasoline reactor catalyst, are in the range of from about 0.1-10.0, 0.1-5.0, 0.1-2.0, 0.3-10.0, 0.3-5.0, 0.3-2.0, 0.5-10.0, 0.5-5.0, 0.5-2.0 or 0.8-1.2. Suitable catalysts used in the second stage pyrolysis gasoline reactor have an expected lifetime in the range of about 18-30, 22-30, 18-26 or 22-26 months.

Hydrotreated pyrolysis gasoline 604, hydrotreated fluid catalytic cracking naphtha 672, and all or a portion of the chemical rich reformate stream 426, are routed to the aromatics extraction zone 620. As noted above, the chemical rich reformate stream 426 can be used in varying quantities as feed to the aromatics extraction zone 620. In certain embodiments to maximize production of petrochemicals, all, a substantial portion or a significant portion of the hydrotreated pyrolysis gasoline 604 is passed to the aromatics extraction zone 620. In modes of operation in which production of gasoline is the objective some of the hydrotreated pyrolysis gasoline 604 is passed to a gasoline pool (not shown).

The aromatics extraction zone 620 includes, for instance, one or more extractive distillation units, and operates to separate the hydrotreated pyrolysis gasoline and fluid catalytic cracking naphtha into high-purity benzene, toluene, xylenes and C9 aromatics. As depicted in FIG. 21, a benzene stream 624, a mixed xylenes stream 626 and a raffinate stream 646 are recovered from the aromatics extraction zone 620, with the raffinate stream 646 routed to the mixed feed steam cracking zone 230 as additional feed. In addition, a toluene stream 636 is passed from the aromatics extraction zone 620 to a toluene and C9+ transalkylation zone 630 for production of additional benzene and xylenes, recycled as stream 640 to the aromatics extraction zone 620. In certain embodiments ethylbenzene can be recovered (not shown). Heavy aromatics 642 are also recovered from the aromatics extraction zone 620.

In certain embodiments of operation of the aromatics extraction zone 620, aromatics are separated from the feed by extractive distillation using, for instance, n-formylmorpholine (NFM), as an extractive solvent. Benzene, toluene, mixed xylenes and C9+ aromatics are separated via distillation. Benzene and mixed xylenes are recovered as product streams 624 and 626, and toluene 636 and C9+ aromatics 638 are sent to the toluene and C9+ transalkylation zone 630. The transalkylation zone product stream 640 containing benzene and mixed xylenes is returned to the recovery section of the aromatics extraction zone 620. A paraffinic raffinate stream 646 is recycled as feed to the mixed feed steam cracking zone 230. In certain embodiments, the paraffinic raffinate stream 646 is in direct fluid communication with the mixed feed steam cracking zone 230, that is, the stream is not subject to further catalytic processing prior to the steam cracking step.

Selection of solvent, operating conditions, and the mechanism of contacting the solvent and feed permit control over the level of aromatic extraction. For instance, suitable solvents include n-formylmorpholine, furfural, N-methyl-2-pyrrolidone, dimethylformamide, dimethylsulfoxide, phenol, nitrobenzene, sulfolanes, acetonitrile, or glycols, and can be provided in a solvent to oil ratio of up to about 20:1, in certain embodiments up to about 4:1, and in further embodiments up to about 2:1. Suitable glycols include diethylene glycol, ethylene glycol, triethylene glycol, tetraethylene glycol and dipropylene glycol. The extraction solvent can be a pure glycol or a glycol diluted with from about 2-10 wt % water. Suitable sulfolanes include hydrocarbon-substituted sulfolanes (e.g., 3-methyl sulfolane), hydroxy sulfolanes (e.g., 3-sulfolanol and 3-methyl-4-sulfolanol), sulfolanyl ethers (e.g., methyl-3-sulfolanyl ether), and sulfolanyl esters (e.g., 3-sulfolanyl acetate).

The aromatic separation apparatus can operate at a temperature in the range of from about 40-200, 40-150, 60-200, 60-150, 86-200 or 80-150° C. The operating pressure of the aromatic separation apparatus can be in the range of from about 1-20, 1-16, 3-20, 3-16, 5-20 or 5-16 barg. Types of apparatus useful as the aromatic separation apparatus in certain embodiments of the system and process described herein include extractive distillation columns.

In one embodiment of operation of the aromatics extraction zone 620, the feed contains primarily C6+ components, and is fractionated into a "heart cut" of C6-C8, a heavy C9+ fraction. The C6-C8 cut is routed to the extractive distillation system where aromatics are separated from non-aromatics (saturates) via solvent distillation. The raffinate (non-aromatics) from the C6-C8 is removed and recycled back to the cracking complex as a feedstock. The aromatics are soluble in the solvent and are carried from the bottom of the extractive distillation column to the solvent stripper where they are stripped from the solvent to produce aromatics extract and lean solvent which is recycled back to the extractive distillation column. The mixed aromatics extract is routed to a series of fractionation columns (a benzene column, a toluene column and a xylene column) where each aromatic species is successively removed, for instance, as benzene stream 624 and mixed xylenes stream 626. The heavy C9+ fraction is further separated into C9 and C10+ material. The toluene and C9 products are routed to the toluene and C9+ transalkylation zone 630 where they are reacted to form additional benzene and mixed xylenes. This stream is recycled back to the fractionation portion of the aromatics extraction zone 620 to recover the benzene and mixed xylenes as well as to recycle the unconverted toluene and C9 aromatics. The transalkylation effluent does not require re-extraction in the solvent distillation section and therefore is routed to the inlet of the benzene column. In certain embodiments toluene can be recycled to extinction, or approaching extinction. C10 and heavier aromatics are removed as product 642. In certain embodiments, ethylbenzene can be recovered.

The toluene and C9+ transalkylation zone 630 operates under conditions effective to disproportionate toluene and C9+ aromatics into a mixed stream 640 containing benzene, mixed xylenes and heavy aromatics. Product ratio of benzene and xylene can be adjusted by selection of catalyst, feedstock and operating conditions. The transalkylation zone 630 receives as feed the toluene stream 636 and the C9+ aromatics stream 638 from the aromatics extraction zone 620. A small quantity of hydrogen 632, in certain embodiments which is obtained all or in part from the hydrogen stream 210 derived from the olefins recovery zone 270, is supplied for transalkylation reactions. Side cracking reactions occur producing fuel gas stream, for instance, passed to the fuel gas system, and LPG stream 634 that is recycled to mixed feed steam cracking zone. A small amount, such as 0.5-3 wt % of the total feed to the aromatics extraction, of heavy aromatics are produced due to condensation reactions and are passed to the mixed stream 640 for recovery with other heavy aromatics.

In operation of one embodiment of the toluene and C9+ transalkylation zone 630, toluene and C9 aromatics are reacted with hydrogen under mild conditions to form a mixture of C6-C11 aromatics. The mixed aromatic product stream 640 is recycled back to the aromatics extraction zone 620 where the benzene and mixed xylenes are recovered as products. C7 and C9 aromatics are recycled back as feed to the transalkylation zone 630, and the C10+ fraction is removed from the aromatics extraction zone 620 as heavy aromatics stream 642. The disproportionation reactions occur in the presence of an effective quantity of hydrogen. Minimal amounts of hydrogen is consumed by cracking reactions under reactor conditions. Purge gas is recycled back to the cracking complex for component recovery.

In certain embodiments, pyrolysis oil streams 236 and 256 can be blended into the fuel oil pool as a low sulfur component, and/or used as carbon black feedstock. In additional embodiments, either or both of the pyrolysis oil streams 236 and 256 can be fractioned (not shown) into light pyrolysis oil and heavy pyrolysis oil. For instance, light pyrolysis oil can be blended with one or more of the middle distillate streams, so that 0-100% of light pyrolysis oil derived from either or both of the pyrolysis oil streams 236 and 256 is processed to produce diesel fuel product and/or additional feed to the mixed feed steam cracking zone 230. In another embodiment 0-100% of light pyrolysis oil derived from either or both of the pyrolysis oil streams 236, 256 can be processed in the vacuum gas oil hydroprocessing zone. In certain embodiments, all, a substantial portion, a significant portion or a major portion of light pyrolysis oil can be passed to one or both of the diesel hydrotreating zone 180 and/or the vacuum gas oil hydroprocessing zone; any remainder can be blended into the fuel oil pool. Heavy pyrolysis oil can be blended into the fuel oil pool as a low sulfur component, and/or used as a carbon black feedstock. In further embodiments, 0-100% of light pyrolysis oil and/or 0-100% of heavy pyrolysis oil derived from either or both of the pyrolysis oil streams 236, 256 can be processed in the optional residue treating zone 800. In certain embodiments, all, a substantial portion, a significant portion or a major portion of the pyrolysis oil streams 236, 256 (light and heavy) can be processed in the optional residue treating zone 800.

Figure 24:
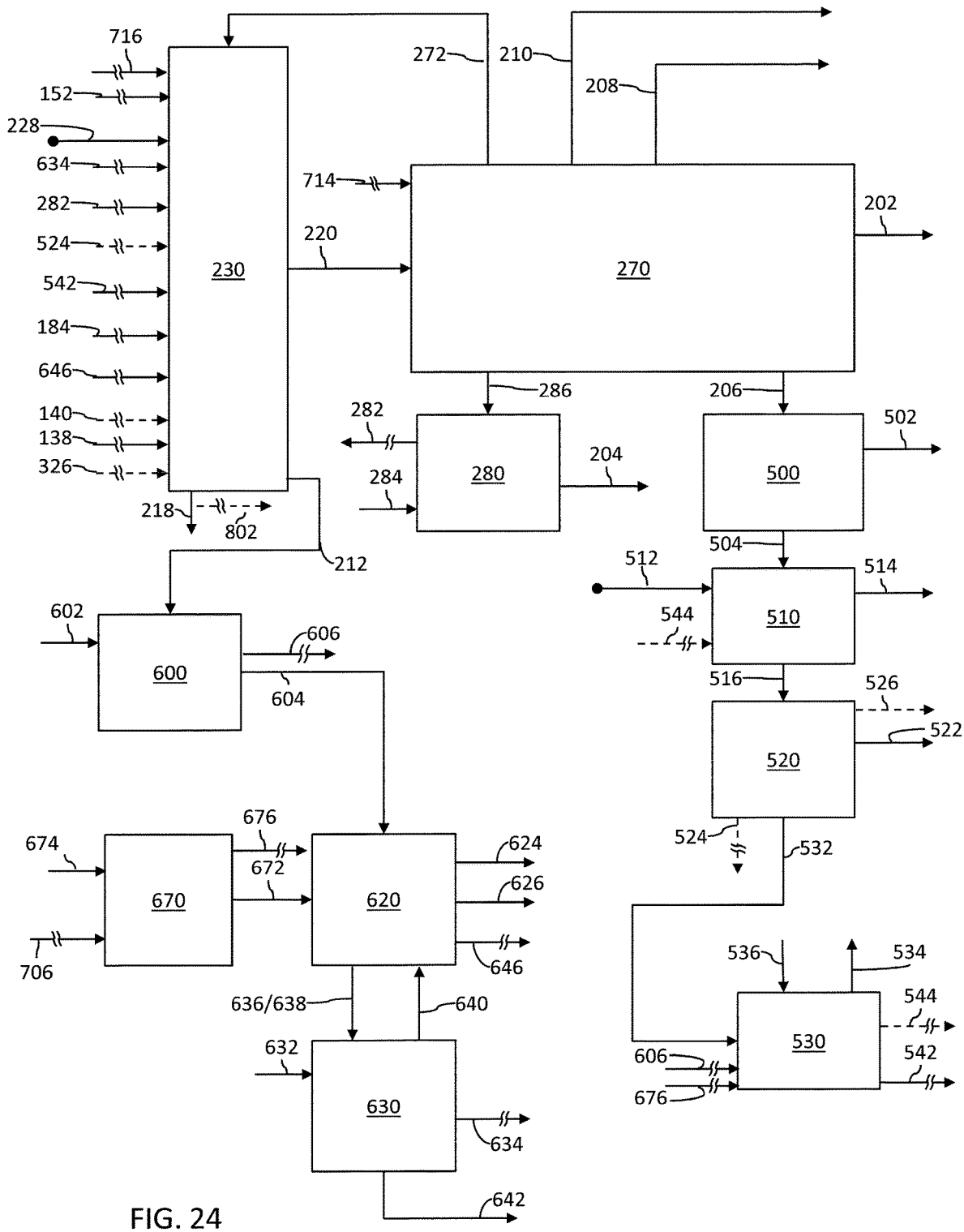
FIG. 24 schematically depicts operations downstream of and including a steam cracker complex in further embodiments of processes for producing petrochemicals and fuel products integrating fluid catalytic cracking, steam cracking and metathesis.

FIG. 24 depicts a variation to any of the above described processes, including integration of a metathesis unit 530. For instance, a suitable metathesis zone 530 can include, but is not limited to, systems based on technology commercially available from Chicago Bridge & Iron Company N.V. (CB&I), NL.

Feedstocks to the metathesis unit 530 include: a portion 536 of the ethylene mixed feed steam cracking product; a C4 raffinate 3 stream 532 from the C4 distillation unit 520, and an olefinic C5 cut 606 from the py-gas hydrotreating zone 600. The C4 Raffinate-3 stream 532 is 0-100% of the total C4 Raffinate-3 from the 1-butene recovery zone 520; any remaining portion 524 can be recycled to the mixed feed steam cracking zone 230. Products from the metathesis unit 530 include propylene 534 and a stream 542, having a mixture of mostly saturated C4/C5 from a metathesis unit that is recycled to the mixed feed steam cracking zone. In certain embodiments, isobutylene 544 can also be recovered (shown in dashed lines) and routed to the methyl tertiary butyl ether zone 510. In embodiments that operate without separation of isobutylene, it is included within stream 542.

Figure 25:
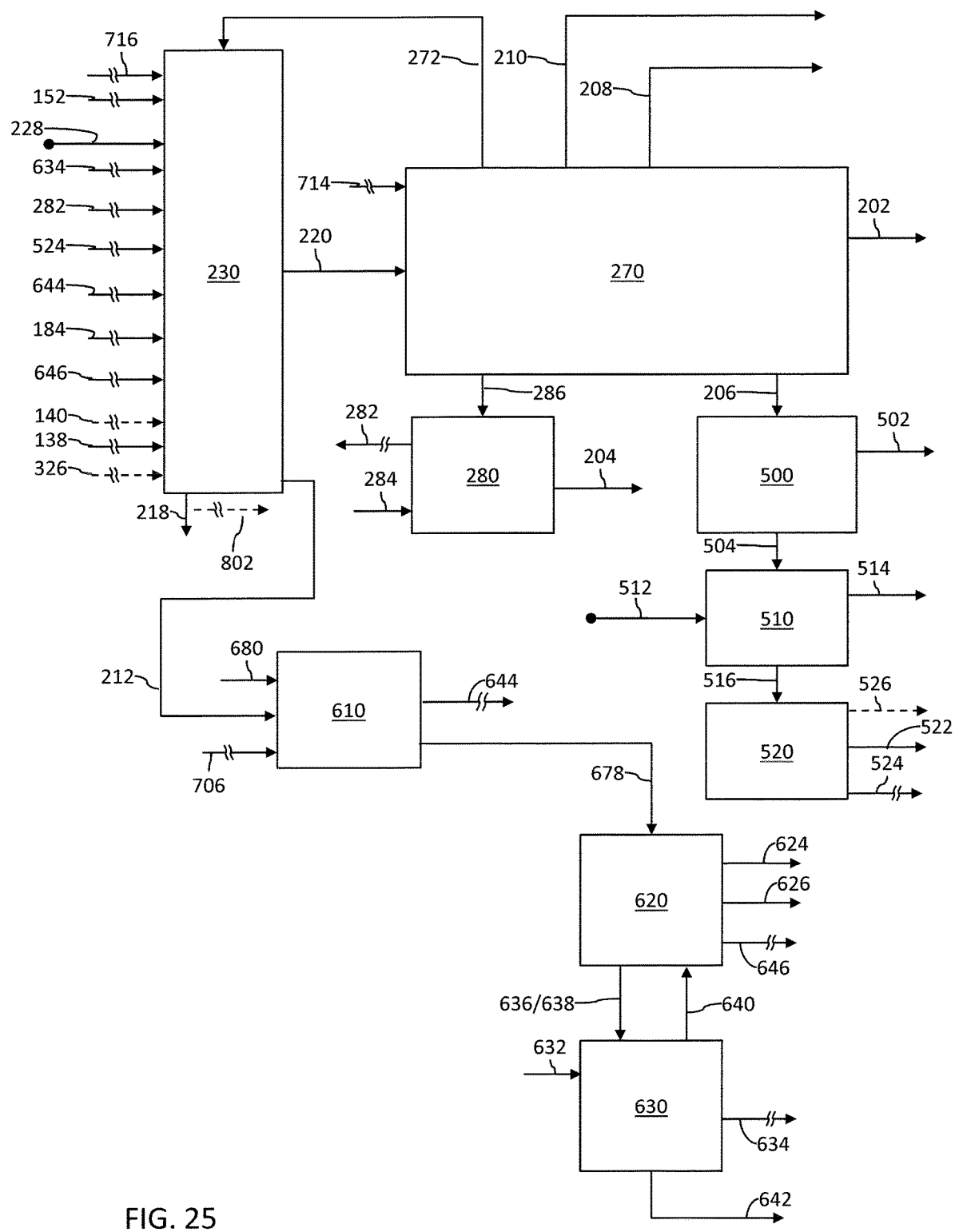
FIG. 25 schematically depicts operations downstream of and including a steam cracker complex in further embodiments of processes for producing petrochemicals and fuel products integrating fluid catalytic cracking and steam cracking.

FIG. 25 depicts an embodiment in which fluid catalytic cracking naphtha 706 and the raw pyrolysis gasoline stream 212 from the steam cracker are commingled and processed in a naphtha hydrotreating zone 610. The naphtha hydrotreating zone 610 operates in the presence of an effective amount of hydrogen obtained from recycle within the naphtha hydrotreating zone 610 and make-up hydrogen 680. In certain embodiments, all or a portion of the make-up hydrogen 680 is derived from the steam cracker hydrogen stream 210 from the olefins recovery train 270. Effluent fuel gas is recovered and, for instance, passed to a fuel gas system.

The effluent from the cracked naphtha hydrotreating reactor generally contain C5-C9+ hydrocarbons. In certain embodiments, C5-C9+ hydrocarbons are passed to the aromatics extraction zone 620, and the aromatics extraction zone 620 includes a depentanizing step to remove C5s. In other embodiments and as shown for instance in FIG. 25, naphtha hydrotreating zone 610 includes a depentanizing step to remove C5s, which are recycled as stream 644 to the mixed feed steam cracking zone 230. The hydrotreated mixed naphtha stream 678, generally containing C6-C9+ hydrocarbons, is passed to the aromatics extraction zone 620. The process of FIG. 25 operates according to the description with respect to FIGS. 12, 13 and 21, or any of the other embodiments herein, in all other aspects.

Figure 26:
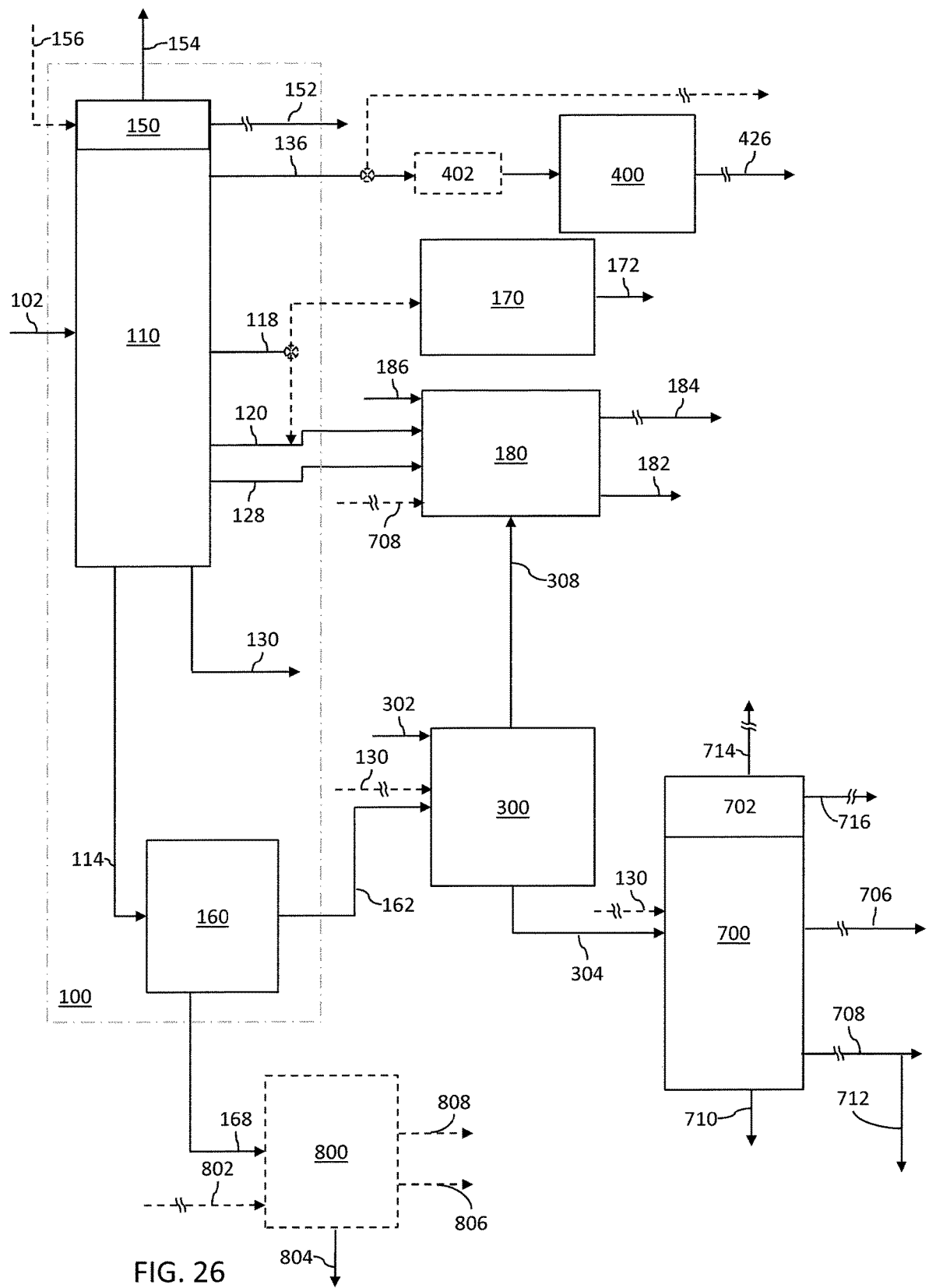
FIGS. 26 and 27 schematically depict operations upstream of a steam cracker complex in still further embodiments of processes for producing petrochemicals and fuel products integrating fluid catalytic cracking and steam cracking.

FIG. 26 depicts an embodiment in which kerosene sweetening is in an optional unit, that is, the first middle distillate fraction 118 can be routed either through the kerosene sweetening zone 170 or routed to the distillate hydrotreating zone 180. The process of FIG. 27 operates according to the description with respect to FIGS. 12, 13 and 21, or any of the other embodiments herein, in all other aspects.

During periods in which maximizing the kerosene fuel 172 is desired, the first middle distillate fraction 118 can be routed to the kerosene sweetening zone 170. During periods in which the feedstock to the mixed feed steam cracking zone 230 is to be maximized, the first middle distillate fraction 118 can be routed to the distillate hydrotreating zone 180, so as to produce additional hydrotreated naphtha 184. In additional alternative embodiments, the first middle distillate fraction 118 can be divided (on a volume or weight basis, for example, with a diverter) so that a portion is passed to the distillate hydrotreating zone 180 and the remaining portion is passed to the kerosene sweetening zone 170.

Figure 27:
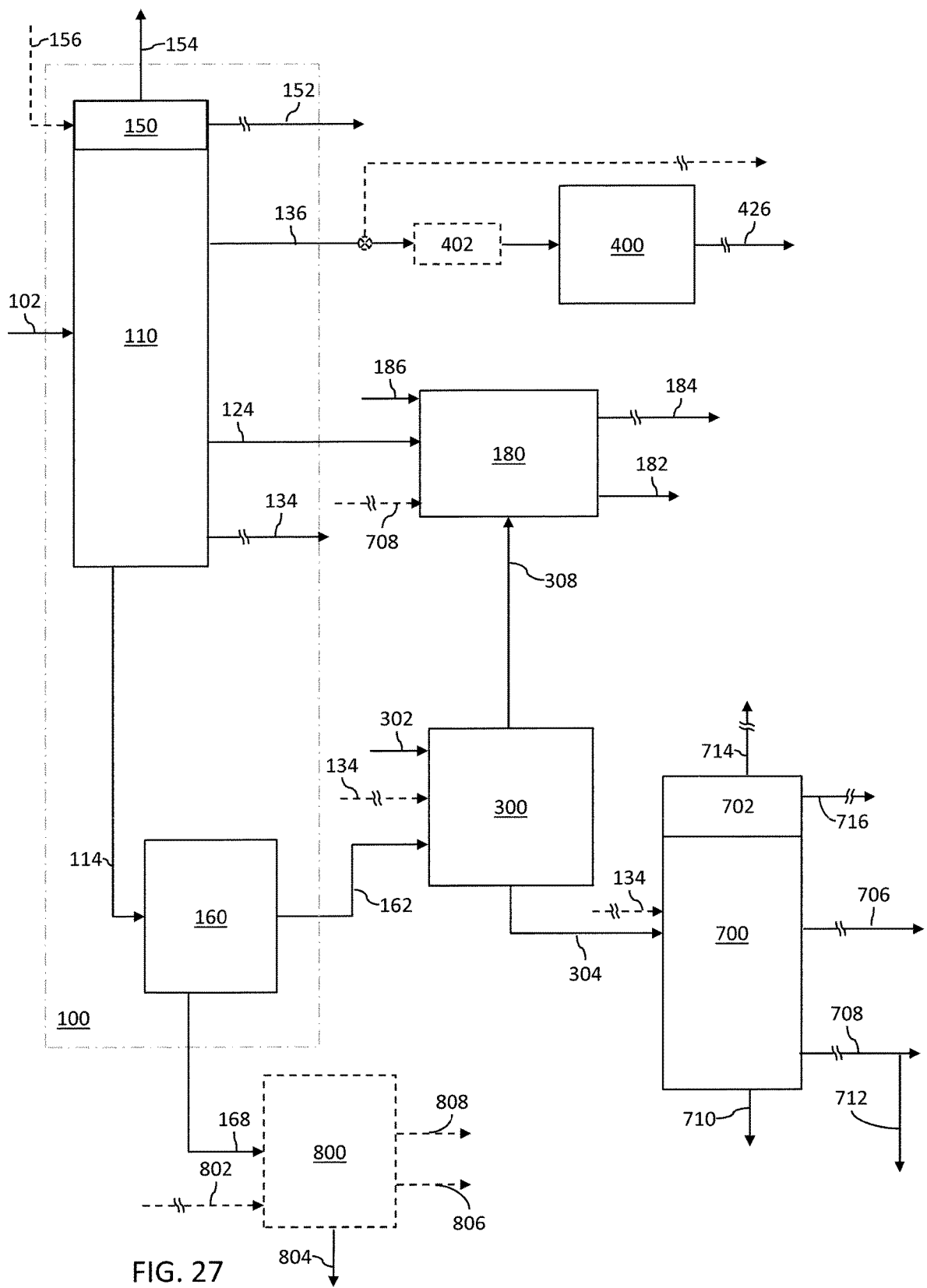

FIG. 27 depicts an embodiment in which kerosene sweetening is eliminated. Accordingly, in the embodiment of FIG. 27 two middle distillate fractions are used. In this embodiment, a first middle distillate fraction 124 is routed to the distillate hydrotreating zone 180, and a second middle distillate fraction 134 may be similar to the third middle distillate fraction 126 described in other embodiments herein. In one example using the arrangement shown in 27, the first middle distillate fraction 124 contains kerosene range hydrocarbons and medium AGO range hydrocarbons, and the second atmospheric distillation zone middle distillate fraction 134 contains heavy AGO range hydrocarbons. In another example using the arrangement shown in FIG. 27, the first middle distillate fraction 124 contains kerosene range hydrocarbons and a portion of medium AGO range hydrocarbons and the second middle distillate fraction 134 contains a portion of medium AGO range hydrocarbons and heavy AGO range hydrocarbons. The process of FIG. 27 operates according to the description with respect to FIGS. 9 and 11, or any of the other embodiments herein, in all other aspects.

Advantageously, process dynamics of the configurations and the integration of units and streams attain a very high level of integration of utility streams between the mixed feed steam cracking and other process units, result in increased efficiencies and reduced overall operating costs. For instance, the hydrogen can be tightly integrated so that the net hydrogen demand from outside of the battery limits is minimized or even eliminated. In certain embodiments, the overall hydrogen utilization from outside of the battery limits is less than about 40, 30, 15, 10 or 5 wt % hydrogen based on the total hydrogen required by the hydrogen users in the integrated process. Hydrogen is recovered from the olefins recovery train and the chemical reformer, and is supplied to the hydrogen users in the system, including the diesel hydrotreater, the gas oil hydrotreater or hydrocracker, the py-gas hydrotreater, the fluid catalytic cracking naphtha hydrotreater, and transalkylation, so as to derive most or all of the utility hydrogen from within the battery limits. In certain embodiments, there is zero external hydrogen use, in which make-up hydrogen is only required to initiate the operation, so that when the reactions reach equilibrium, the hydrogen derived from the mixed feed steam cracking products provides sufficient hydrogen to maintain the hydrogen requirements of the hydrogen users in the integrated process. In further embodiments, there is a net hydrogen gain, so that hydrogen can be added, for instance, to the fuel gas that is used to operate the various heating units within the integrated process.

Furthermore, the integrated process described herein offers useful outlets for the off-gases and light ends from the hydroprocessing units. For instance, the stream 156 that is passed to the saturated gas plant 150 of the crude complex 100 can contain off-gases and light ends from the hydroprocessing units, such as the diesel hydrotreating zone 180, the gas oil hydrotreating zone 300 and/or from the py-gas hydrotreating zone 600. In other embodiments, in combination with or as an alternative to the passing these off-gases and light ends to stream 156, all or a portion can be routed to the mixed feed steam cracking unit 230. For instance, C2s can be separated from the mixture of methane, hydrogen and C2s using a cold distillation section ("cold box") including cryogenic distillation/separation operations, which can be integrated with any or all of the mixed feed steam cracking unit 230, the saturated gas plant 150 and/or the olefins recovery zone 270. Methane and hydrogen can be passed to a fuel gas system or to an appropriate section of the olefins recovery zone 270, such as the hydrogen purification system. In still further embodiments, in combination with or as an alternative to the passing these off-gases and light ends to stream 156 and/or routing them to the mixed feed steam cracking unit 230, all or a portion can be routed to an appropriate section of the olefins recovery zone 270, such as the depropanizer, or combining the gases with the depropanizer overheads.

Embodiments described herein provide the ability to achieve a crude to chemical conversion ratio in the range of, for instance, up to 80, 50 or 45 wt %, and in certain embodiments in the range of about 39-45 wt %. In certain embodiments the chemical conversion ratio is at least about 39 wt %, and in certain embodiments in the range of about 39-80, 39-50 or, 39-45 wt %. It should be appreciated that this crude to chemicals conversion ratio can vary depending on criteria such as feed, selected technology, catalyst selection and operating conditions for the individual unit operations.

In some embodiments, individual unit operations can include a controller to monitor and adjust the product slate as desired. A controller can direct parameters within any of the individual unit operations the apparatus depending upon the desired operating conditions, which may, for example, be based on customer demand and/or market value. A controller can adjust or regulate valves, feeders or pumps associated with one or more unit operations based upon one or more signals generated by operator data input and/or automatically retrieved data.

Such controllers provide a versatile unit having multiple modes of operation, which can respond to multiple inputs to increase the flexibility of the recovered product. The controller can be implemented using one or more computer systems which can be, for example, a general-purpose computer. Alternatively, the computer system can include specially-programmed, special-purpose hardware, for example, an application-specific integrated circuit (ASIC) or controllers intended for a particular unit operation within a refinery.

The computer system can include one or more processors typically connected to one or more memory devices, which can comprise, for example, any one or more of a disk drive memory, a flash memory device, a RAM memory device, or other device for storing data. The memory is typically used for storing programs and data during operation of the system. For example, the memory can be used for storing historical data relating to the parameters over a period of time, as well as operating data. Software, including programming code that implements embodiments of the invention, can be stored on a computer readable and/or writeable nonvolatile recording medium, and then typically copied into memory wherein it can then be executed by one or more processors. Such programming code can be written in any of a plurality of programming languages or combinations thereof.

Components of the computer system can be coupled by one or more interconnection mechanisms, which can include one or more busses, for instance, between components that are integrated within a same device, and/or a network, for instance, between components that reside on separate discrete devices. The interconnection mechanism typically enables communications, for instance, data and instructions, to be exchanged between components of the system.

The computer system can also include one or more input devices, for example, a keyboard, mouse, trackball, microphone, touch screen, and other man-machine interface devices as well as one or more output devices, for example, a printing device, display screen, or speaker. In addition, the computer system can contain one or more interfaces that can connect the computer system to a communication network, in addition or as an alternative to the network that can be formed by one or more of the components of the system.

According to one or more embodiments of the processes described herein, the one or more input devices can include sensors and/or flow meters for measuring any one or more parameters of the apparatus and/or unit operations thereof. Alternatively, one or more of the sensors, flow meters, pumps, or other components of the apparatus can be connected to a communication network that is operatively coupled to the computer system. Any one or more of the above can be coupled to another computer system or component to communicate with the computer system over one or more communication networks. Such a configuration permits any sensor or signal-generating device to be located at a significant distance from the computer system and/or allow any sensor to be located at a significant distance from any subsystem and/or the controller, while still providing data therebetween. Such communication mechanisms can be affected by utilizing any suitable technique including but not limited to those utilizing wired networks and/or wireless networks and protocols.

Although the computer system is described above by way of example as one type of computer system upon which various aspects of the processes herein can be practiced, it should be appreciated that the invention is not limited to being implemented in software, or on the computer system as exemplarily described. Indeed, rather than implemented on, for example, a general purpose computer system, the controller, or components or subsections thereof, can alternatively be implemented as a dedicated system or as a dedicated programmable logic controller (PLC) or in a distributed control system. Further, it should be appreciated that one or more features or aspects of the processes can be implemented in software, hardware or firmware, or any combination thereof. For example, one or more segments of an algorithm executable by a controller can be performed in separate computers, which in turn, can be in communication through one or more networks.

In some embodiments, one or more sensors and/or flow meters can be included at locations throughout the process, which are in communication with a manual operator or an automated control system to implement a suitable process modification in a programmable logic controlled process. In one embodiment, a process includes a controller which can be any suitable programmed or dedicated computer system, PLC, or distributed control system. The flow rates of certain product streams can be measured, and flow can be redirected as necessary to meet the requisite product slate.

Factors that can result in various adjustments or controls include customer demand of the various hydrocarbon products, market value of the various hydrocarbon products, feedstock properties such as API gravity or heteroatom content, and product quality (for instance, gasoline and middle distillate indicative properties such as octane number for gasoline and cetane number for middle distillates).

The disclosed processes and systems create new outlets for direct conversion of crude oil, for instance, light crudes such as Arab Extra Light (AXL) or Arab Light (AL) crude oil. Additionally, the disclosed processes and systems offer novel configurations that, compared to known processes and systems, requires lower capital expenditure relative to conventional approaches of chemical production from fuels or refinery by-products and that utilize refining units and an integrated chemicals complex. The disclosed processes and systems substantially increase the proportion of crude oil that is converted to high purity chemicals that traditionally command high market prices. Complications resulting from advancing the threshold of commercially proven process capacities are minimized or eliminated using the processes and systems described herein.

The disclosed processes and systems utilize different commercially proven units arranged in novel configurations. These novel configurations enable production of refined products and petrochemical products including olefins, aromatics, MTBE, and butadiene. The disclosed processes and systems allow chemicals producers to de-couple from fuel markets and have more freedom to increase chemical yields as a fraction of crude rate, as compared to traditional chemical production using refinery intermediates or by-products as feedstock. Also, the disclosed processes and systems substantially increase the proportion of crude oil that is converted to high purity chemicals that traditionally command high market prices.

The disclosed processes and systems provide alternatives for chemicals production that have lower capital investment relative to conventional routes that utilize refining units and an integrated chemicals complex. Moreover, the disclosed processes and systems offer the flexibility of simultaneously producing fuel products and chemical products. The ratio of chemicals to residual fuels can be modulated by process operations to address changing fuels and chemical market opportunities. In certain embodiments, the process configurations are flexible to enable processing of crude oil, such as Arab Light or Arab Extra Light, to provide superior production of chemical products, while minimizing the production of refined fuel products. The configurations offer the flexibility to structure operations to adjust the ratio of petrochemicals to refined products in order to achieve optimum operations and allows shifting the production ratio of chemicals to fuels, thereby adjusting to market conditions.

For example, in vacuum gas oil hydroprocessing, as severity increases, the yield of UCO (or hydrotreated gas oil) decreases as the naphtha yield increases, although for the most part the distillate yield does change as much because wild naphtha product is the result of distillate cracking. The UCO product is chemically restructured through ring opening reactions to become much more paraffinic in nature, and remains a gas oil boiling range product. By modulating severity of vacuum gas oil hydroprocessing, the shift is between naphtha and UCO (or hydrotreated gas oil) relative product rates. The olefin yield of naphtha in the steam cracker is superior to UCO (or hydrotreated gas oil); while the heavy product yield (mixed C4s and pyrolysis gasoline) from UCO (or hydrotreated gas oil) is superior to naphtha. Therefore, a key advantage of modulating the vacuum gas oil hydroprocessing conversion is to economically and dynamically address changing market conditions for olefin and aromatic products, which may swing dramatically.

Each of the processing units are operated at conditions typical for such units, which conditions can be varied based on the type of feed to maximize, within the capability of the unit's design, the desired products. Desired products can include fractions suitable as feedstock to the mixed feed steam cracking zone 230, or fractions suitable for use as fuel products. Likewise, processing units employ appropriate catalyst(s) depending upon the feed characteristics and the desired products. Certain embodiments of these operating conditions and catalysts are described herein, although it shall be appreciated that variations are well known in the art and are within the capabilities of those skilled in the art.

For the purpose of the simplified schematic illustrations and descriptions herein, accompanying components that are conventional in crude centers, such as the numerous valves, temperature sensors, preheater(s), desalting operation(s), and the like are not shown.

Further, the numerous valves, temperature sensors, electronic controllers and the like that are conventional in fluid catalyst cracking are not included. Further, accompanying components that are in conventional in fluid catalyst cracking systems such as, for example, air supplies, catalyst hoppers, flue gas handling the like are also not shown.

In addition, accompanying components that are in conventional hydroprocessing units such as, for example, hydrogen recycle sub-systems, bleed streams, spent catalyst discharge sub-systems, and catalyst replacement sub-systems the like are not shown.

Further, accompanying components that are in conventional thermal cracking systems such as steam supplies, coke removal sub-systems, pyrolysis sections, convection sections and the like are not shown.

The method and system of the present invention have been described above and in the attached drawings; however, modifications will be apparent to those of ordinary skill in the art and the scope of protection for the invention is to be defined by the claims that follow.

The invention claimed is:

1. An integrated process for producing petrochemicals and fuel products from a crude oil feed comprising:
separating from the crude oil feed, in an atmospheric distillation unit (ADU), at least
a first ADU fraction comprising straight run naphtha,
a second ADU fraction comprising at least a portion of middle distillates from the crude oil feed, and
a third ADU fraction comprising atmospheric residue;
separating from the third ADU fraction, in a vacuum distillation unit (VDU), at least
a first VDU fraction comprising vacuum gas oil;
hydroprocessing in a distillate hydroprocessing (DHP) zone middle distillates from the second ADU fraction, and recovering at least a first DHP fraction and a second DHP fraction, wherein the first DHP fraction comprises naphtha and the second DHP fraction is used for diesel fuel production;
processing, in a catalytic reforming zone, naphtha from the first ADU fraction, and recovering chemical rich reformate;
processing in a fluid catalytic cracking zone the first VDU fraction to produce at least a first FCC fraction corresponding to light olefins that are recovered as petrochemicals, a second FCC fraction corresponding to FCC naphtha and a third FCC fraction corresponding to cycle oil;
steam cracking, in a mixed feed steam cracking (MFSC) zone, naphtha from the first ADU fraction and raffinate derived from an aromatics extraction zone, and, in a gas oil steam cracking (GOSC) zone, hydrotreated gas oil, wherein steam cracking operates under conditions effective to recover at least a mixed product stream H2, methane, ethane, ethylene, mixed C3s and mixed C4s; pyrolysis gas; and pyrolysis oil;
recovering, from the mixed product stream, H2, methane, non-olefinic C2-C4s, and petrochemicals ethylene, propylene and butylenes,
hydroprocessing pyrolysis gas from steam cracking in a naphtha hydroprocessing zone, and recovering hydrotreated pyrolysis gas; and
separating aromatics from hydrotreated pyrolysis gas and chemical rich reformate from the catalytic reforming zone in the aromatics extraction zone for recovery of petrochemical aromatic products, and aromatics extraction zone raffinate, wherein the raffinate derived from aromatics extraction is all or a portion of the aromatics extraction zone raffinate.

2. The process as in claim 1, wherein the chemical reforming zone includes a semi-regeneration, cyclic regeneration or continuous catalyst regeneration arrangement enabling contact of the naphtha feed with mono-functional or bi-functional reforming catalyst, to produce the chemical rich reformate.

3. The process in claim 1, wherein naphtha is hydrotreated prior to processing in the catalytic reforming zone.

4. The process in claim 1, wherein an n-paraffin rich stream is separated from the naphtha prior to reforming, and wherein at least a portion of the paraffin rich stream is passed to the MFSC.

5. The process as in claim 1, further comprising hydrotreating the second FCC fraction to produce hydrotreated FCC naphtha.

6. The process as in claim 5, further comprising processing the hydrotreated FCC naphtha in the aromatics extraction complex for recovery of additional aromatic products and additional aromatics extraction zone raffinate that is recycled to the MFSC zone.

7. The process as in claim 5, further comprising recovering C5s from the hydrotreated FCC naphtha and recycling the recovered C5s to the MFSC zone.

8. The process as in claim 7, further comprising processing the hydrotreated FCC naphtha in the aromatics extraction complex for recovery of additional aromatic products and additional aromatics extraction zone raffinate that is recycled to the MFSC zone.

9. The process as in claim 1, wherein at least a significant portion of the first DHP fraction is passed to the MFSC zone or to the ADU.

10. The process as in claim 1, further comprising hydroprocessing in a gas oil hydroprocessing (GOHP) zone vacuum gas oil from the first VDU fraction prior to processing in the fluid catalytic cracking zone, and recovering a first GOHP fraction containing components boiling at or below an atmospheric residue end boiling point and including LPG, naphtha and middle distillate range components, and a second GOHP fraction containing heavy oil, which passed to the fluid catalytic cracking zone.

11. The process as in claim 10, wherein at least a significant portion of naphtha from the first GOHP fraction is routed to the MFSC zone or to the atmospheric distillation zone.

12. The process as in claim 10, wherein at least a significant portion of the first GOHP fraction is routed to the distillate hydroprocessing zone.

13. The process as in claim 10, further wherein the middle distillates in the second ADU fraction comprise heavy atmospheric gas oil that is processed in the gas oil hydroprocessing zone.

14. The process as in claim 10, further wherein the middle distillates in the second ADU fraction comprise heavy atmospheric gas oil that is processed in the fluid catalytic cracking zone without hydroprocessing, and the first VDU fraction is hydroprocessed in the gas oil hydroprocessing zone.

15. The process as in claim 10, further comprising passing at least a portion of the third FCC fraction in the distillate hydroprocessing zone.

16. The process as in claim 10, wherein the GOHP zone operates under hydrocracking conditions and in the presence of hydrocracking catalyst to convert 27-99 wt % of feed to the GOHP zone into the first GOHP fraction, and wherein the second GOHP fraction comprises unconverted oil.

17. The process as in claim 10, wherein the GOHP zone operates under hydrotreating conditions and in the presence of hydrotreating catalyst to convert 2-30 wt % of feed to the GOHP zone into the first GOHP fraction, and wherein the second GOHP fraction comprises hydrotreated gas oil.

18. The process as in claim 10, further wherein the middle distillates in the second ADU fraction comprise heavy atmospheric gas oil that is routed to the GOHP zone.

19. The process as in claim 10, further wherein the middle distillates in the second ADU fraction comprise heavy atmospheric gas oil that is processed in the GOSC zone without hydroprocessing.

20. The process as in claim 10, wherein the middle distillates in the second ADU fraction comprise kerosene that is processed in a kerosene sweetening process to recover a kerosene fuel product, and a straight run diesel fraction that is the portion of the second ADU fraction that is processed in the distillate hydroprocessing zone.

21. The process as in claim 20, further wherein the middle distillates in the second ADU fraction comprise heavy atmospheric gas oil that is processed in the GOHP zone or the GOSC zone.

22. The process as in claim 1, wherein at least a significant portion of the first DHP fraction is passed to the MFSC zone or to the ADU.

23. The process claim 10, wherein at least a significant portion of naphtha from the first GOHP fraction is routed to the catalytic reforming zone.

24. The process as in claim 10, wherein at least a significant portion of the first GOHP fraction is routed to the distillate hydroprocessing zone.

25. The process as in claim 1, further comprising separating non-olefinic C4s recovered from the mixed product stream, wherein said non-olefinic C4s are recycled to the MFSC zone.

26. The process as in claim 1, further comprising separating non-olefinic C4s recovered from the mixed product stream, wherein said non-olefinic C4s are recycled to a separate processing zone for production of additional petrochemicals.

27. The process as in claim 26, wherein the separate processing zone converts mixture of butenes into mixed butanols.

28. The process as claim 26, further comprising
recovering C5s from the hydrotreated pyrolysis gas;
passing the recovered C5s to the separate processing zone for production of additional petrochemicals; and
passing a portion of the recovered ethylene to the separate processing zone;
wherein the separate processing zone is a metathesis reaction zone which produces petrochemical propylene and a C4/C5 raffinate stream that is recycled to the MFSC zone.

29. The process as in claim 1, further comprising recovering C5s from the hydrotreated pyrolysis gas and passing the recovered C5s to the MFSC zone, a separate processing zone for production of additional petrochemicals, or both to the MFSC zone and a separate processing zone for production of additional petrochemicals.

30. The process as in claim 29 wherein the recovered C5s are passed to the MFSC zone.

31. The process as in claim 29 wherein the recovered C5s are passed to the separate processing zone for production of additional petrochemicals, wherein the separate processing zone converts mixture of butenes into mixed butanols.

32. The process as in claim 1, wherein a crude to chemicals conversion ratio of at least about 39 wt % is achieved.

* * * * *